US008697645B2

(12) United States Patent
Acharya et al.

(10) Patent No.: US 8,697,645 B2
(45) Date of Patent: Apr. 15, 2014

(54) SECOND GENERATION LOW OXYGEN AFFINITY PEGYLATED HEMOGLOBINS AS OXYGEN-CARRYING PLASMA EXPANDERS

(75) Inventors: Seetharama A. Acharya, Cresskill, NJ (US); Belur N. Manjula, Cresskill, NJ (US)

(73) Assignee: Albert Einstein College of Medicine of Yeshiva University, Bronx, NY (US)

( * ) Notice: Subject to any disclaimer, the term of this patent is extended or adjusted under 35 U.S.C. 154(b) by 920 days.

(21) Appl. No.: 12/449,832

(22) PCT Filed: Mar. 12, 2008

(86) PCT No.: PCT/US2008/003303
§ 371 (c)(1),
(2), (4) Date: May 3, 2010

(87) PCT Pub. No.: WO2008/136888
PCT Pub. Date: Nov. 13, 2008

(65) Prior Publication Data
US 2010/0216695 A1    Aug. 26, 2010

Related U.S. Application Data

(60) Provisional application No. 60/906,736, filed on Mar. 13, 2007.

(51) Int. Cl.
*A61K 38/42* (2006.01)
*C07K 14/805* (2006.01)
*A61P 7/00* (2006.01)

(52) U.S. Cl.
USPC ............................................. 514/6; 530/385

(58) Field of Classification Search
None
See application file for complete search history.

(56) References Cited

U.S. PATENT DOCUMENTS

| | | | |
|---|---|---|---|
| 4,598,064 A * | 7/1986 | Walder | 514/13.4 |
| 5,585,484 A | 12/1996 | Acharya et al. | |
| 5,750,725 A | 5/1998 | Acharya et al. | |
| 6,017,943 A | 1/2000 | Acharya et al. | |
| 7,019,117 B2 | 3/2006 | Acharya et al. | |
| 7,144,989 B2 | 12/2006 | Acharya et al. | |
| 7,169,900 B2 | 1/2007 | Acharya et al. | |
| 7,501,499 B2 | 3/2009 | Acharya et al. | |
| 7,521,174 B2 | 4/2009 | Acharya et al. | |
| 2004/0002443 A1 * | 1/2004 | Acharya et al. | 514/6 |
| 2006/0135753 A1 | 6/2006 | Acharya et al. | |

OTHER PUBLICATIONS

Molecular Probes (2001)—Section 5.2 Chemical Crosslinking Reagents http://www.ebiotrade.com/buyf/productsf/molecular%20probes/sections/0502.htm.*

(Continued)

*Primary Examiner* — Scott Long
*Assistant Examiner* — Sarah Alawadi
(74) *Attorney, Agent, or Firm* — Amster, Rothstein & Ebenstein LLP

(57) ABSTRACT

Provided are hemoglobins having at least two chemical modifications that lower oxygen affinity, hemoglobins chemically modified by the addition of glyceraldehyde-3-phosphate, and hemoglobins having at least two specific chemical modifications. PEGylated versions of these hemoglobins are also provided, as are certain tetraPEGylated and diPEGylated hemoglobins. Methods of modifying a hemoglobin are additionally provided, as are methods of making a hemoglobin. Pharmaceutical compositions and blood substitutes using these hemoglobins are further provided, as are methods of treating a subject using these pharmaceutical compositions and blood substitutes.

19 Claims, 14 Drawing Sheets

(56) References Cited

OTHER PUBLICATIONS

Manjula et al. Conjugation of Multiple Copies of Polyethylene Glycol to Hemoglobin Facilitated Through Thiolation: Influence on Hemoglobin Structure and Function. The Protein Journal. vol. 24, No. 3 (Apr. 2005).*

Mita Sanghavi. Methemoglobinemia (Mar. 13, 2003).*

Acharya A S et al., Selectivity in the Modification of the alpha-Amino Groups of Hemoglobin on Reductive Alkylation with Aliphatic Carbonyl Compounds, The Journal of Biological Chemistry, vol. 260, No. 10, Issue of May 25, pp. 6039-6046, 1985.

Meunier L et al., The nuclear export signal-dependent localization of oligonucleopeptides enhances the inhibition of the protein expression from a gene transcribed in cytosol, Nucleic Acids Research, 1999, vol. 27, No. 13, 2730-2736.

Hu T et al., Influence of intramolecular cross-links on the molecular, structural and functional properties of PEGylated haemoglobin, Biochem J., 2007, 402, 143-151.

PCT Notification of Transmittal of The International Search Report and The Written Opinion of The International Searching Authority, or the Declaration dated Nov. 3, 2008 in connection with PCT International Patent Application No. PCT/US2008/003303, 11 pages.

PCT International Preliminary Report on Patentability and Written Opinion of the International Searching Authority dated Sep. 15, 2009 in connection with PCT International Patent Application No. PCT/US2008/003303, 5 pages.

* cited by examiner

# SECOND GENERATION LOW OXYGEN AFFINITY PEGYLATED HEMOGLOBINS AS OXYGEN-CARRYING PLASMA EXPANDERS

CROSS-REFERENCE TO RELATED APPLICATIONS

This application is a national stage entry under 35 U.S.C. §371 of PCT International Patent Application No. PCT/US2008/003303, filed Mar. 12, 2008, and claims priority to U.S. Provisional Patent Application No. 60/906,736, filed Mar. 13, 2007, the contents of which are incorporated herein by reference in their entirety.

STATEMENT OF GOVERNMENT SUPPORT

The invention disclosed herein was made with U.S. Government support under Grant Nos. HL58247 and HL71064 awarded by The National Institutes of Health, and Grant No. PR023085 awarded by The United States Army. Accordingly, the U.S. Government has certain rights in this invention.

FIELD OF THE INVENTION

The present invention generally relates to hemoglobin-based blood substitutes. More specifically, the invention is directed to chemically modified hemoglobin that has very low oxygen affinity, PEGylated hemoglobins produced by new protocols, and combinations thereof.

BACKGROUND OF THE INVENTION

Hemoglobin (Hb) based blood substitutes are being developed rapidly to overcome the shortage of blood supply (Chang, 1999; Klein, 2000). The most extensively studied and financed blood substitute was diaspirin cross-linked Hb (Winslow, 2000a). Although intramolecular crosslinking of Hb overcame the nephrotoxicity and high oxygen affinity of the acellular Hb (Chang, 1999), the product remained vasoactive (Kramer, 2003; Winslow, 2000b), which has been attributed to the scavenging of nitric oxide by the extravasated acellular Hb (Winslow, 2000a). Enhancing the molecular size of Hb by oligomerization and lowering the affinity of Hb to nitric oxide by site directed mutagenesis are two solutions to overcoming the vasoactivity of Hb. Animal studies have shown that both approaches reduce the pressor effect of Hb (Gulati et al., 1999).

Enzon PEGylated bovine Hb carries ten copies of polyethylene glycol 5000 (PEG-5K) chains, and was non-hypertensive (Conover et al., 1999). Its enhanced molecular volume, high viscosity and high colloidal osmotic pressure (COP) have been attributed as the molecular basis of neutralizing the vasoactivity of acellular Hb (Intaglietta, 1997). Accordingly, PEGylation of Hb has been considered as a new approach to generate non-hypertensive Hb (Rohlfs et al., 1998; Winslow et al., 1998). In an attempt to establish that the neutralization of the vasoactivity is a generalized consequence of PEGylation of Hb, a non-hypertensive hexaPEGylated Hb, (SP-PEG5K)$_6$-Hb was generated using extension arm facilitated PEGylation protocol (Acharya et al., 2005; Manjula et al., 2005). Compared with the Enzon decaPEGylated bovine Hb, (SP-PEG5K)$_6$-Hb has less number of PEG-5K chains conjugated, and the positive charge of Hb was not changed upon linking the extension arm or on conjugating the PEG-chains through the thiol groups at the distal end of the extension arms (conservative PEGylation) (Acharya et al., 2005; Manjula et al., 2005). Therefore, the results reflect the higher efficiency of conservative PEGylation to neutralize the vasoactivity of Hb.

The non-hypertensive PEGylated Hb (SP-PEG5K)$_6$-Hb exhibits a very high oxygen affinity, which was considered as a consequence of the PEGylation at Cys-93($\beta$) of Hb (Acharya et al., 2005). High oxygen affinity for an Hb-based oxygen carrier has been advocated as a desirable property to generate non-hypertensive Hb, as this will reduce the propensity of the acellular Hb to off load the oxygen on the arterial side of the circulation (Vandegriff et al., 2003).

Recently, a reductive alkylation chemistry mediated hexaPEGylated Hb, (Propyl-PEG5K)$_6$-Hb, was generated (Hu et al., 2005). The oxygen affinity of (Propyl-PEG5K)$_6$-Hb is comparable to that of (SP-PEG5K)$_6$-Hb, even though Cys-93($\beta$) was unmodified in (Propyl-PEG5K)$_6$-Hb. However, the COP of (Propyl-PEG5K)$_6$-Hb were considerably higher than that of (SP-PEG5K)$_6$-Hb. In general, the COP of the protein solution is a correlate of the number of particles (molecules) in the solution. Accordingly, the higher COP of (Propyl-PEG5K)$_6$-Hb could be a consequence of larger number of molecules in the solution than that in the solution of (SP-PEG5K)$_6$-Hb at the same protein concentration. Typically, Hb undergoes the tetramer-dimer dissociation, which involves cleavage of the non-covalent interactions along the symmetric interfaces $\alpha_1\beta_2$ and $\alpha_2\beta_1$ (Perutz, 1970; Baldwin and Chothia, 1979). Therefore, the different COP values between the two PEGylated proteins are possibly due to the fact that the tetramer-dimer dissociation of Hb is enhanced by the two PEGylation protocols at different levels. Besides, if (Propyl-PEG5K)$_6$-Hb is predominantly present in dimers, it can lead to the high oxygen affinity of (Propyl-PEG5K)$_6$-Hb.

Based on the above, it would be desirable to have a PEGylated hemoglobin with low oxygen affinity. The present invention addresses that need.

SUMMARY OF THE INVENTION

Accordingly, the inventors have developed several novel hemoglobins with useful chemical modifications.

The present invention is directed to a hemoglobin having at least two chemical modifications, where each chemical modification by itself results in a hemoglobin with lower oxygen affinity than the same hemoglobin that is unmodified.

The invention is also directed to a hemoglobin chemically modified by the addition of glyceraldehyde-3-phosphate.

Additionally, the invention is directed to a hemoglobin having at least two chemical modifications, where each chemical modification is independently an intramolecular crosslink, an affinity labeling of an effector binding domain, or an introduction of a negative charge at the amino terminal of a $\beta$-chain.

The invention is further directed to any of the above hemoglobins, PEGylated.

The invention is additionally directed to a hemoglobin tetraPEGylated by extension arm facilitated maleimide chemistry.

Also, the invention is directed to a hemoglobin diPEGylated by extension arm facilitated maleimide chemistry.

The present invention is also directed to methods of modifying a hemoglobin. The methods comprise introducing at least two chemical modifications to the hemoglobin, where each chemical modification by itself results in a hemoglobin with lower oxygen affinity than the same hemoglobin that is unmodified.

Further, the invention is directed to other methods of modifying a hemoglobin. The methods comprise adding glyceraldehyde-3-phosphate to the hemoglobin in the presence of sodium cyanoborohydride.

Additionally, the present invention is directed to additional methods of modifying a hemoglobin. The methods comprise introducing at least two chemical modifications to the hemoglobin, where each chemical modification is independently an intramolecular crosslink, an affinity labeling of an effector binding domain, or an introduction of a negative charge at the amino terminal of a β-chain.

The invention is further directed to methods of making a hemoglobin. The methods comprise tetraPEGylating the hemoglobin by extension arm facilitated maleimide chemistry.

The invention is additionally directed to other methods of making a hemoglobin. These methods comprise diPEGylating the hemoglobin by extension arm facilitated maleimide chemistry.

Further, the present invention is directed to compositions comprising any of the above-described hemoglobins in a pharmaceutically acceptable carrier.

Also, the invention is directed to blood substitutes comprising any of the above-described hemoglobins.

The invention is also directed to blood substitutes any of the above-described PEGylated hemoglobins.

The present invention is additionally directed to methods of treating a subject. The methods comprise administering to the subject the above-described composition.

Also, the present invention is directed to other methods of treating a subject. The methods comprise administering to the subject any of the above-described blood substitutes.

DETAILED DESCRIPTION OF THE INVENTION

Figure 1:
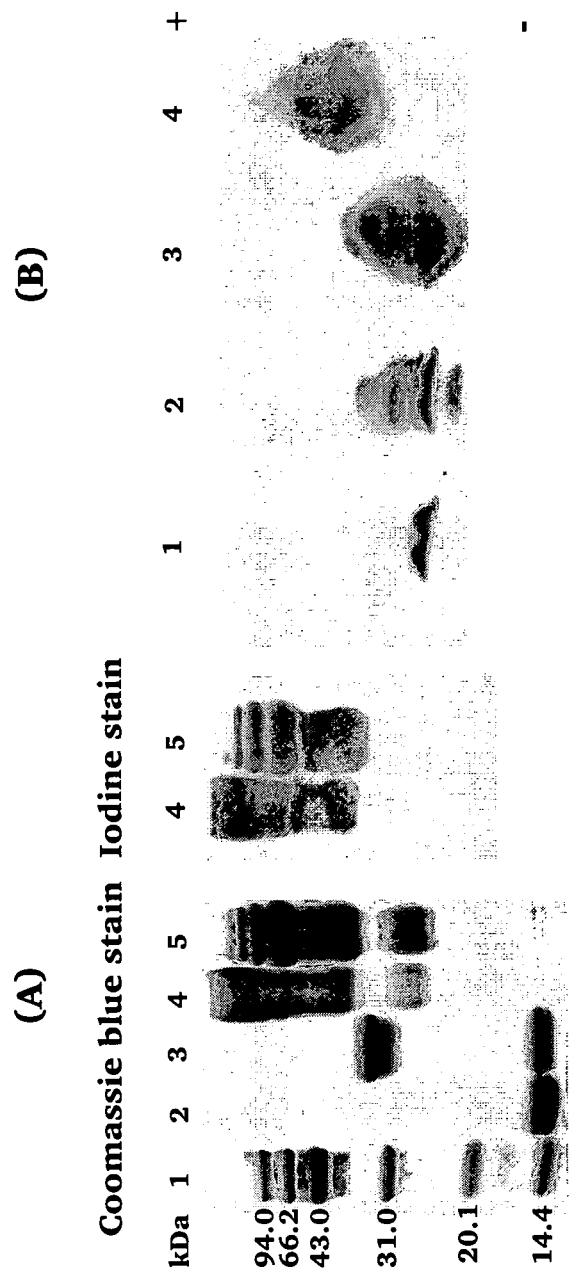
FIG. 1A-1B are photographs of SDS-PAGE (left) and isoelectric focusing (IEF) (right) blots characterizing PEGylated proteins. SDS-PAGE was carried out on a precast 14% trisglycine gel from the Invitrogen Corporation. (A) Lane 1, the molecular weight markers; Lane 2, HbA; Lane 3, αα-fumaryl Hb; Lane 4, (Propyl-PEG5K)$_6$-αα-Hb; and Lane 5, (Propyl-PEG5K)$_6$-Hb. Proteins were identified by Coomassie blue staining, and PEG was detected by iodine staining. (Propyl-PEG5K)$_6$-αα-Hb and (Propyl-PEG5K)$_6$-Hb were both loaded at the same amount of protein content (12 μg). IEF was operated using precast resolve gels from Isolab and a blend of pH 6-8 resolve ampholytes. (B) Lane 1, HbA; Lane 2, αα-fumaryl Hb; Lane 3, (Propyl-PEG5K)$_6$-Hb; and Lane 4, (Propyl-PEG5K)$_6$-αα-Hb.

Accordingly, the inventors have developed several novel hemoglobins with useful chemical modifications.

The present invention is directed to a hemoglobin having at least two chemical modifications, where each chemical modification by itself results in a hemoglobin with lower oxygen affinity than the same hemoglobin that is unmodified.

As used herein, "oxygen affinity" is the strength of binding of oxygen to a hemoglobin molecule. The $P_{50}$ (the oxygen pressure [e.g., measured in mm Hg] where the hemoglobin is 50% saturated) is a measure of oxygen affinity, and is measured by determination of the hemoglobin oxygen-dissociation curve. See examples.

These invention hemoglobins are not narrowly limited to the use of any particular chemical modification that results in lower oxygen affinity. A preferred such chemical modification is an intramolecular crosslink. Some of these intramolecular crosslinks are αα crosslinks. A preferred αα-crosslink is an αα-fumaryl crosslink at Lys-99(α). Others of the intramolecular crosslinks are ββcrosslinks. A preferred ββ crosslink is a ββ-succinimidophenyl crosslink at Cys-93 (β). Most preferably, the ββ crosslink is a ββ-succinimidophenyl PEG-2000 intramolecular crosslink at Cys-93(β).

Another preferred chemical modification that results in lower oxygen affinity is an affinity labeling of an effector binding domain. Preferably, the modification affinity labels the hemoglobin with 2-[4-(3,5-dichlorophenylureido)phenoxy]-2-methylpropionic acid (L35), 2,3-diphosphoglycerate (DPG) or inositol hexaphosphate (IHP).

An additional preferred chemical modification is the introduction of a negative charge at the amino terminal of a β-chain. Non-limiting preferred examples of such an introduction is by carboxymethylation, galacturonic acid modification, or pyridoxal phosphate modification. Another preferred introduction of a negative charge is by glyceraldehyde-3-phosphate modification of the hemoglobin. An additional preferred example of the introduction of a negative charge at the amino terminal of a β-chain is by 2-hydroxy, 3-phospho propylation (HPPr).

Most preferably, one chemical modification is by HPPr and the other chemical modification is an αα-fumaryl crosslink at Lys-99(α).

The inventors have also discovered that the addition of glyceraldehyde-3-phosphate to a hemoglobin results in reduced oxygen affinity. See Example 2. Thus, the invention is also directed to a hemoglobin chemically modified by the addition of glyceraldehyde-3-phosphate.

The hemoglobin in these embodiments can be any type of hemoglobin now known or later discovered. The skilled artisan could select an appropriate hemoglobin for any particular purpose without undue experimentation. For many purposes, including for use as a plasma extender or a blood substitutes, the hemoglobin is preferably hemoglobin A (HbA). Additionally, the hemoglobin can be from any species as deemed appropriate for the particular purpose contemplated. For use on humans, the hemoglobin is preferably human hemoglobin. Most preferably, the hemoglobin is human hemoglobin A.

The hemoglobin can additionally comprise a mutation (i.e., an alteration in the amino acid sequence from the wild-type sequence) that lowers the oxygen affinity of the hemoglobin. Non-limiting examples include $β^{D21G}$ ($β^{D21G}$ (a β chain where the wild-type Asp at residue 21 is substituted with a Gly) (the mutant β chain incorporated in Hb Connecticut-Moo-Penn et al., 1981), $β^{N108Q}$ (U.S. Pat. No. 6,486,123), $β^{L105W}$ (Id.), $α^{V96W}$ (U.S. Pat. No. 5,843,888), and $α^{D94N}$ (Hb Titusville-Schneider et al., 1975).

The invention hemoglobin here can also have advantageous mutations, now known or later discovered, that do not result in lower oxygen affinity, such as mutations that improve the stability or prevent a disease or other undesirable phenotype of the resulting hemoglobin. Non-limiting examples of such mutations include $β^{T87Q}$, which prevents polymerization of the abnormal sickle cell hemoglobin (HbS), and $α^{L29F}$, which improves stability (U.S. Pat. No. 6,486,123). The present invention also encompasses the use of hemoglobin having two or more mutations conferring lower oxygen affinity or other advantageous properties.

A preferred hemoglobin mutation that results in lower oxygen affinity is $β^{N108K}$ known as Hb-Presbyterian (Hb-P).

The hemoglobin that is chemically modified here can be isolated from animal or human blood, or can be synthesized, e.g., using recombinant DNA technology.

The hemoglobin can be from any species. For hemoglobins that are going to be administered to an animal, e.g., to a human as a plasma extender or blood substitute, the hemoglobin can be from a different species, or preferably the same species, as the species that is being treated. The hemoglobin can also be an interspecies hemoglobin hybrid. See, e.g., Rao et al., 2000.

The present invention is also directed to a hemoglobin having at least two chemical modifications, where each chemical modification is independently an intramolecular crosslink, an affinity labeling of an effector binding domain, or an introduction of a negative charge at the amino terminal of a β-chain.

Preferably, one chemical modification is by HPPr and the other chemical modification is an αα-fumaryl crosslink at Lys-99(α). It is also preferred that the hemoglobin is a hemoglobin A. Additionally, it is preferred that the hemoglobin is a human hemoglobin, particularly when the hemoglobin is going to be administered to a human. Most preferably, the hemoglobin is a human hemoglobin A.

Any of the hemoglobins above can be PEGylated, e.g., to eliminate vasoactivity of the hemoglobin. A preferred method of PEGylation, is by reductive alkylation (see examples). Another preferred method of PEGylation is by extension arm facilitated maleimide chemistry (see examples). More preferably, the hemoglobin is tetraPEGylated by extension arm facilitated maleimide chemistry. In other preferred embodiments, the hemoglobin is diPEGylated by extension arm facilitated maleimide chemistry. Most preferably, the tetraPEGylated and diPEGylated hemoglobin further comprises at least one thiol at a Cys-93(β). See Example 3.

The most preferred hemoglobin of those described above is a PEGylated human hemoglobin A, having one chemical modification that is HPPr and another chemical modification that is an αα-fumaryl crosslink at Lys-99(α).

The invention is additionally directed to a hemoglobin tetraPEGylated by extension arm facilitated maleimide chemistry. Further, the invention is directed to a hemoglobin diPEGylated by extension arm facilitated maleimide chemistry. With both of these hemoglobins PEGylated by extension arm facilitated maleimide chemistry, it is also preferred that they comprise at least one thiol at a Cys-93(β), for improved oxygen affinity. See Example 3. The most preferred hemoglobin here is tetraPEGylated by extension arm facilitated maleimide chemistry, and further comprising at least one thiol at a Cys-93(β).

The present invention is also directed to methods of modifying a hemoglobin. The methods comprise introducing at least two chemical modifications to the hemoglobin, where each chemical modification by itself results in a hemoglobin with lower oxygen affinity than the same hemoglobin that is unmodified.

A preferred chemical modification here is an intramolecular crosslink. Some of these intramolecular crosslinks are αα crosslinks. A preferred αα-crosslink is an αα-fumaryl crosslink at Lys-99(α). Others of the intramolecular crosslinks are ββ crosslinks. A preferred ββ crosslink is a ββ-succinimidophenyl crosslink at Cys-93(β). Most preferably, the ββ crosslink is a ββ-succinimidophenyl PEG-2000 intramolecular crosslink at Cys-93(β).

Another preferred chemical modification that results in lower oxygen affinity is an affinity labeling of an effector binding domain. Preferably, the modification affinity labels the hemoglobin with 2-[4-(3,5-dichlorophenylureido)phenoxy]-2-methylpropionic acid (L35), 2,3-diphosphoglycerate (DPG) or inositol hexaphosphate (IHP).

An additional preferred chemical modification is the introduction of a negative charge at the amino terminal of a β-chain. Non-limiting preferred examples of such an introduction is by carboxymethylation, galacturonic acid modification, or pyridoxal phosphate modification. Another preferred introduction of a negative charge is by glyceraldehyde-3-phosphate modification of the hemoglobin. Most preferably, the addition of glyerceraldehyde-3-phosphate is performed in the presence of sodium cyanoborohydride. An additional preferred example of the introduction of a negative charge at the amino terminal of a β-chain is by 2-hydroxy, 3-phospho propylation (HPPr).

Most preferably, one chemical modification is by HPPr and the other chemical modification is an αα-fumaryl crosslink at Lys-99(α). Here, it is preferred that the αα-fumaryl crosslink is introduced into an HPPr-Hb.

Further, the invention is directed to additional methods of modifying a hemoglobin. The methods comprise adding glyceraldehyde-3-phosphate to the hemoglobin in the presence of sodium cyanoborohydride.

Additionally, the present invention is directed to other methods of modifying a hemoglobin. The methods comprise introducing at least two chemical modifications to the hemoglobin, where each chemical modification is independently an intramolecular crosslink, an affinity labeling of an effector binding domain, or an introduction of a negative charge at the amino terminal of a β-chain. Preferably, one chemical modification is by HPPr and the other chemical modification is an αα-fumaryl crosslink at Lys-99(α). More preferably, the hemoglobin is a hemoglobin A. It is also preferred that the hemoglobin is a human hemoglobin. Most preferably, the hemoglobin is a human hemoglobin A.

With any of the above methods, the hemoglobin is preferably a hemoglobin A (HbA). Also with any of the above methods, the hemoglobin is preferably a human hemoglobin. In the most preferred embodiments, one chemical modification is by HPPr, the other chemical modification is an αα-fumaryl crosslink at Lys-99(α), and the hemoglobin is a human hemoglobin A.

With any of the methods above, the hemoglobins can be PEGylated, e.g., to eliminate vasoactivity of the hemoglobin. A preferred method of PEGylation, is by reductive alkylation. Another preferred method of PEGylation is by extension arm facilitated maleimide chemistry. More preferably, the hemoglobin is tetraPEGylated by extension arm facilitated maleimide chemistry. In other preferred embodiments, the hemoglobin is diPEGylated by extension arm facilitated maleimide chemistry. Most preferably, the tetraPEGylated and diPEGylated hemoglobin further comprises at least one thiol at a Cys-93(β). Preferred methods to retain the thiol at a Cys-93(β) comprise protecting the Cys before PEGylation, then deprotected after PEGylation. More preferably, the Cys-93(β) is protected with dithiopyridine and deprotected with Tris(2-carboxyethyl)phosphine (TCEP).

The preferred methods here result in a PEGylated human hemoglobin A, having one chemical modification that is HPPr and another chemical modification that is an αα-fumaryl crosslink at Lys-99(α). Most preferably, the hemoglobin is tetraPEGylated by extension arm facilitated maleimide chemistry, and further comprises at least one thiol at a Cys-93(β).

The invention is further directed to methods of making a hemoglobin. The methods comprise tetraPEGylating the hemoglobin by extension arm facilitated maleimide chemistry.

The invention is additionally directed to other methods of making a hemoglobin. These methods comprise diPEGylating the hemoglobin by extension arm facilitated maleimide chemistry.

With the methods resulting in tetraPEGylated or diPEGylated hemoglobin discussed immediately above, the hemoglobin preferably further comprises at least one thiol at a Cys-93(β). Here, the thiol at the Cys-93(β) is preferably retained by protecting the Cys-93(β) before PEGylation, then deprotecting the site after PEGylation. Most preferably, the Cys-93(β) is protected with dithiopyridine and deprotected with Tris(2-carboxyethyl)phosphine (TCEP).

The invention also provides a composition comprising any of the hemoglobins disclosed herein or prepared by any of the methods disclosed herein, in a pharmaceutically acceptable carrier. The invention further provides a blood substitute (plasma volume expander) comprising any of the hemoglobins or PEGylated hemoglobins disclosed herein or prepared by any of the methods disclosed herein. Pharmaceutically acceptable carriers include, but are not limited to, saline, phosphate buffered saline, Ringer's solution, lactated Ringer's solution, Locke-Ringer's solution, Kreb's Ringer's solution, Hartmann's balanced saline solution, and/or heparinized sodium citrate acid dextrose solution. The pharmaceutical compositions of the present invention may be administered by conventional means including but not limited to transfusion and injection. The invention provides methods of treating a subject which comprises administering to the subject any of the hemoglobins or PEGylated hemoglobins disclosed herein.

Preferred embodiments of the invention are described in the following examples. Other embodiments within the scope of the claims herein will be apparent to one skilled in the art from consideration of the specification or practice of the invention as disclosed herein. It is intended that the specification, together with the examples, be considered exemplary only, with the scope and spirit of the invention being indicated by the claims, which follow the examples.

Example 1

Influence of Intramolecular Cross-Links on the Molecular, Structural and Functional Properties of PEGylated Hemoglobin Example Summary This Example is published as Hu et al. (2007). The influence of intramolecular cross-links on the molecular, structural and functional properties of PEGylated hemoglobin (Hb) has been investigated. The sites and the extent of PEGylation of Hb by reductive alkylation are not influenced by the presence of an αα-fumaryl cross-link at Lys-99(α). The hexaPEGylated crosslinked Hb, (Propyl-PEG5K)$_6$-αα-Hb, exhibits larger molecular radius and lower colloidal osmotic pressure than hexaPEGylated uncrosslinked Hb, (Propyl-PEG5K)$_6$-Hb. Perturbation of the heme microenvironment and the β1β2 interface by PEGylation of Hb is reduced by intramolecular crosslinking. Sedimentation velocity analysis established that PEGylation destabilizes the tetrameric structure of Hb. (Propyl-PEG5K)$_6$-Hb and (Propyl-PEG5K)$_6$-αα-Hb sediment as stable dimeric and tetrameric molecules, respectively. ββ-succinimidophenyl PEG-2000 crosslink at Cys-93(β) outside the central cavity also influences the molecular properties of Hb, comparable to that by αα-fumaryl crosslink within the central cavity. However, the influence of the two crosslinks are very distinct on the oxygen affinity of PEGylated Hb, indicating that high oxygen affinity of PEGylated Hb is not a direct consequence of the dissociation of the Hb tetramers into dimers. αα-fumaryl crosslink is preferred to modulate both oxygen affinity and molecular properties of PEGylated Hb, and crosslink outside the central cavity could only modulate molecular properties of PEGylated Hb. It is suggested that PEGylation induces a hydrodynamic drag on Hb and this plays a role in the microcirculatory properties of PEGylated Hb.

Abbreviations. Hb, hemoglobin; αα-fumaryl Hb, αα-intramolecular crosslinked hemoglobin at Lys-99(α); ββ-Hb, ββ-intramolecular crosslinked hemoglobin at Cys-93(β); PEG, polyethylene glycol; PEGylation, conjugation with polyethylene glycol; PBS, phosphate buffered saline; COP, colloidal osmotic pressure; IEF, isoelectric focusing; SP, succinimidophenyl; (SP-PEG5K)$_6$-Hb, a hexaPEGylated hemoglobin generated by thiolation mediated maleimide chemistry based PEGylation of hemoglobin with PEG5K; (Propyl-PEG5K)$_6$-Hb, a hexaPEGylated hemoglobin generated by reductive alkylation of hemoglobin by PEG5K propionaldehyde; (Propyl-PEG5K)$_6$-αα-Hb, a hexaPEGylated hemoglobin generated by reductive alkylation of αα-intramolecular crosslinked hemoglobin by PEG5K propionaldehyde; (Propyl-PEG5K)$_6$-ββ-Hb, a hexaPEGylated hemoglobin generated by reductive alkylation of ββ-intramolecular crosslinked hemoglobin by PEG5K propionaldehyde; SEC, size exclusion chromatography; CD, circular dichroism; S, sedimentation coefficient.

Introduction

In the present study, the influence of the presence of intramolecular crosslinks in Hb on the molecular, structural and functional properties of PEG-Hb conjugates was investigated. The reductive alkylation chemistry-mediated PEGylation of Hb has been chosen as the method for PEGylation of Hb, as this approach shows a higher level of site selectivity than extension arm facilitated PEGylation. The intramolecularly crosslinked Hb at Lys-99(α), αα-fumaryl Hb, has been chosen as the model approach in view of the extensive structural and colligative information available. The molecular, structural and functional properties of PEGylated uncrosslinked and crosslinked Hb were compared. The new information generated here is expected to facilitate the design of novel Hb based blood substitutes.

EXPERIMENTAL

Reductive Alkylation of HbA with PEG5K-aldehyde. Human adult hemoglobin (HbA) was purified from human erythrocytes as previously described (Manjula and Acharia, 2003). αα-fumaryl Hb was prepared as previously described (Chatterjee et al., 1986). ββ-succinimidophenyl PEG-2000 crosslinked HbA (ββ-Hb) was prepared as described by Manjula et al., 2000). HbA, αα-fumaryl Hb and ββ-Hb (0.25 mM tetramer) in 50 mM BisTris-Ac buffer (pH 6.5) were reacted with 10 mM ω-methoxy PEG 5000 propionaldehyde (PEG-5K aldehyde, Shearwater Polymers, Huntsville, Ala.) in the presence of 50 mM sodium cyanoborohydride (Sigma Chemical Co., St. Louis, Mo.) at 4° C. overnight, respectively. The reaction mixture was subjected to diafiltration through a 70-kDa membrane vs. PBS (pH 7.4) using a Minim Tangential Flow Filtration instrument (Pall Corporation, Ann Arbor, Mich.) to remove unreacted PEG and other excess reagents. The final product in the retentate was concentrated and stored frozen at −80° C.

Dynamic Light Scattering. Dynamic light scattering for molecular radius measurement was performed using a DynaPro instrument (Protein Solutions, Lakewood, N.J.). Samples at the protein concentration of 1 mg/ml were centrifuged at 13,000 rpm for 4 min prior to analysis.

Analytical Methods. Size exclusion chromatography (SEC) of PEGylated proteins were carried out using Superose 12 columns (1×30 cm). RPHPLC analysis of globin chains on a Vydac C4 column (4.6×250 mm), and SDS-PAGE analysis were carried out as previously described (Manjula et al., 2003; Rao et al., 1994). Isoelectric focusing (IEF) analysis was operated using precast resolve gels from Isolab and a blend of pH 6-8 resolve ampholytes. Gels were electro-focused for 3 h to resolve the components in the sample completely. The colloidal osmotic pressure and viscosity of PEGylated proteins were measured as described by Hu et al., 2005. Oxygen-binding equilibrium measurements of PEGylated proteins were carried out using a Hem-o-scan analyzer at 37° C. as described by Manjula et al., 2003.

Tryptic Peptide Mapping. Tryptic peptide mapping of the PEGylated proteins was carried out by methods previously described (Lippincott et al., 1997; Doyle et al., 1999). The tryptic peptides were analyzed by RPHPLC on a Vydac C18 column (10×250 mm) (Hu et al., 2005). Percent modification of the peptides in the PEGylated proteins was calculated by the ratio of the peak area of each peptide of the PEGylated Hb and PEGylated αα-fumaryl Hb relative to the corresponding peak in the HbA and αα-fumaryl Hb peptide map, respectively. The recovery of peptide βT4 was used as an internal standard.

Analytical Ultracentrifugation. Sedimentation velocity measurements were conducted in a Beckman XL-I analytical ultracentrifuge in PBS buffer at pH 7.4, 25° C. and 55,000 rpm. Boundary movement was followed at 405 nm using the centrifuge's absorption optics. For each sample, data were collected at three nominal concentrations (A405=0.1, 0.5 and 1.0). The g(s*) distributions were determined using DCDT+ version 2.0.4 (http://www.jphilo.mailway.com) using values of $\bar{v}$ of 0.74 mL/g for HbA (Kellett, 1971) and 0.806 mL/g for the PEGylated proteins (Dhalluin et al., 2005) and normalized to standard conditions (S20, W and D20, W) by correcting for buffer density and viscosity.

Circular Dichroism Spectroscopy. Circular dichroism spectra of Hb samples were recorded on a JASCO-720 spectropolarimeter (JASCO, Tokyo, Japan) at 25° C. with a 0.2-cm light path cuvette (310 μl). For the spectra from 250 to 200 nm, the Hb concentration was 1.3 μM as tetramer. For the spectra from 480 to 250 nm, the Hb concentration was 26.0 μM as tetramer. All the Hb samples were in PBS, pH 7.4. The molar ellipticity, θ, is expressed in deg.cm$^2$/dmol on a heme basis.

Front-face Fluorescence Measurements. Intrinsic front-face fluorescence measurements of Hb samples were performed using Shimadzu RF-5301 spectrofluorimeter at room temperature. The emission spectra were recorded from 300 to 400 nm using an excitation wavelength of 280 nm. Excitation and emission slit widths were both 5 nm. All the samples used were at Hb concentration of 5.7 mg/ml in PBS, pH 7.4. A cuvette with 1 cm path-length was used.

Results

Influence of αα-fumaryl Intramolecular Crosslink on the Site Selectivity and Extent of PEGylation of Hb. The sites and the extent of PEGylation of αα-fumaryl Hb are presented in Table 1. As can be seen, Val-1(α) and Val-1(β) have been completely modified by PEGylation in αα-fumaryl Hb, same as that in HbA. Besides, four lysine residues also showed modification by PEGylation in αα-fumaryl Hb to some extent and are comparable to those in HbA. Thus, the presence of αα-fumaryl intramolecular crosslink in the central cavity of Hb has essentially little influence on the site selectivity of PEGylation. Accordingly, PEGylated αα-fumaryl Hb is referred to (Propyl-PEG5K)$_6$-αα-Hb, in conformity with the earlier nomenclature of hexaPEGylated Hb, (Propyl-PEG5K)$_6$-Hb (Hu et al., 2005).

Electrophoretic Analysis of PEGylated Proteins. As shown by SDS-PAGE analysis (FIG. 1A), the electrophoretic pattern for HbA is a doublet corresponding to α and β chain (Lane 2). The α chain of αα-fumaryl Hb showed a slower mobility as a consequence of cross-linking (Lane 3). (Propyl-PEG5K)$_6$-Hb displays two major and two minor protein bands with slower mobility than the unmodified globin chains (Lane 5). For (Propyl-PEG5K)$_6$-αα-Hb (Lane 4), the two major bands of (Propyl-PEG5K)$_6$-Hb became lighter with the concomitant appearance of two new bands with slower mobility upon αα-crosslinking. The detection of attached PEG chains to Hb by the iodine stain showed that stain intensity is comparable between the two PEGylated proteins. This suggests that the attached PEG chains are comparable between the two PEGylated proteins.

The influence of the intramolecular crosslinking on the IEF pattern of the PEGylated proteins is shown in FIG. 1B. The PEGylated proteins do not focus as compact bands, and are distinct from HbA and αα-fumaryl Hb. (Propyl-PEG5K)$_6$-Hb focused slightly beyond HbA, and (Propyl-PEG5K)$_6$-αα-Hb focused slightly beyond (Propyl-PEG5K)$_6$-Hb. Since the reductive alkylation chemistry based PEGylation of Hb could conserve the positive charge of Hb, the influence of PEGylation on the IEF pattern reflects the molecular shielding influence of the PEG-shell on the surface charges of Hb from the bulk solvent (Li et al., 2006). Since HbA and αα-fumaryl Hb exhibit similar isoelectric patterns, the molecular shielding influence of the PEG-shell on the surface charges of (Propyl-PEG5K)$_6$-Hb is enhanced as a result of αα-fumaryl intramolecular crosslinks.

Figure 2:
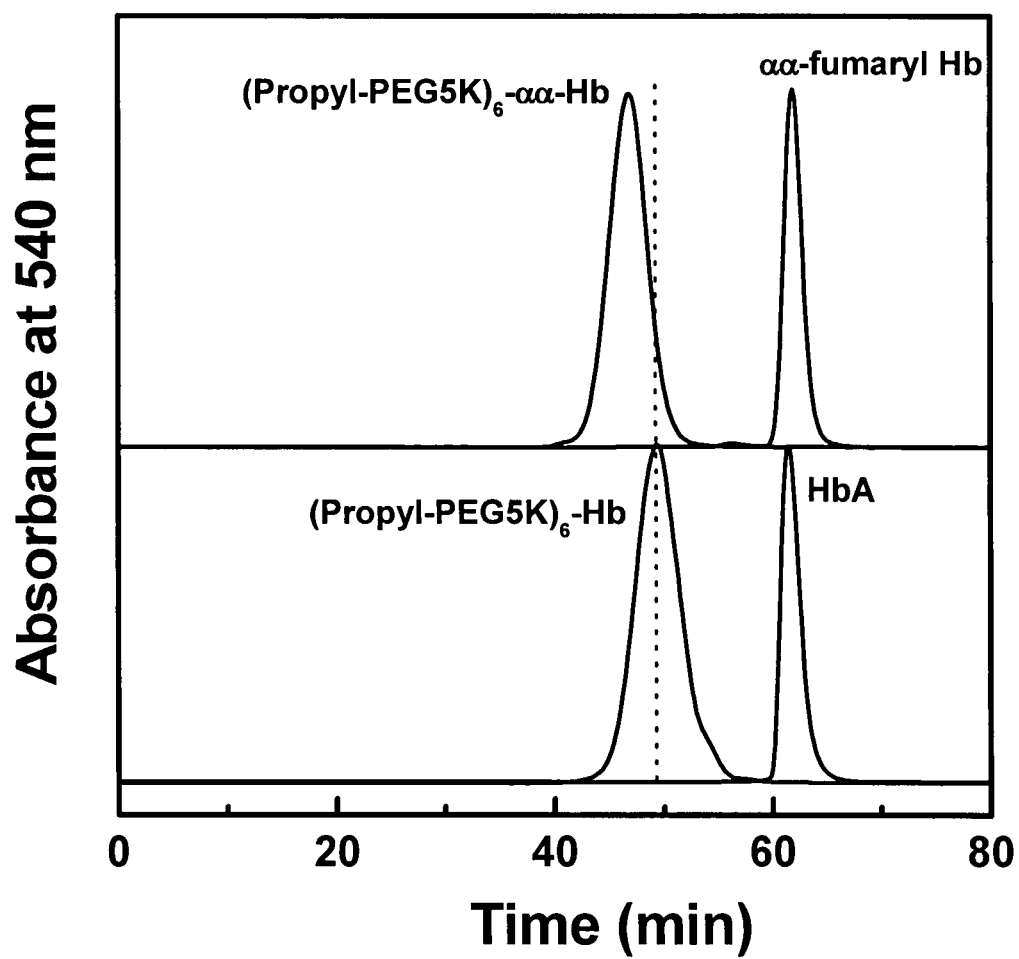
FIG. 2 are graphs of a size exclusion chromatographic analysis of PEGylated Hb samples. The analysis was carried out at room temperature on two HR 10/30 Superose 12 columns (Amersham-Pharmacia Biotech) connected in series. The columns were eluted with PBS, pH 7.4 at a flow rate of 0.5 ml/min, and the effluent was monitored at 540 nm.

Hydrodynamic Volume of PEGylated Proteins Determined by SEC. The hydrodynamic volume of PEGylated proteins was measured by SEC. As shown in FIG. 2, PEGylation of HbA results in an earlier elution of the protein, reflecting a significant increase in the hydrodynamic volume of Hb. The SEC pattern of HbA is not influenced by the presence of αα-fumaryl intramolecular crosslinks. PEGylation of αα-fumaryl Hb results in larger hydrodynamic volume than that of PEGylation of HbA, as reflected by the earlier elution. Based on the results of the tryptic peptide mapping (Table 1), the increase in the hydrodynamic volume of (Propyl-PEG5K)$_6$-αα-Hb is not related to the higher level or an altered site selectivity of PEGylation. Thus, αα-fumaryl intramolecular cross-link in Hb appears to increase the hydrodynamic volume of PEGylated Hb.

TABLE 1

Sites of PEGylation in αα-fumaryl Hb

| Residue modified | Percent modification | |
|---|---|---|
| | (Propyl-PEG5K)$_6$-Hb | (Propyl-PEG5K)$_6$-αα-Hb |
| Val-1(α) | 100 | 100 |
| Val-1(β) | 100 | 100 |
| Lys-8(β) | 23 | 23 |
| Lys-11(α) | 23 | 27 |
| Lys-40(α) | 12 | 11 |
| Lys-56(α) | 17 | 22 |

The sites of PEGylation in the PEGylated proteins are determined by tryptic peptide mapping of their globin chains as described in Experimental Procedures.

Molecular Volume of PEGylated Proteins Determined by Dynamic Light Scattering. The molecular radius of the PEGylated proteins, as determined by dynamic light scattering and their calculated molecular volume are summarized in Table 2. The molecular radius of αα-fumaryl Hb is comparable to that of HbA. (Propyl-PEG5K)$_6$-Hb showed a molecular radius of 5.40 nm, reflecting the enhanced molecular dimensions of HbA upon PEGylation. Interestingly, the molecular radius of (Propyl-PEG5K)$_6$-αα-Hb exhibits further increase as compared to (Propyl-PEG5K)$_6$-Hb, and its calculated molecular volume is nearly twice that of (Propyl-PEG5K)$_6$-Hb.

TABLE 2

Molecular Radius of Hexa PEGylated Hbs

| Sample | Radius (nm) | Molecular volume (nm$^3$) |
|---|---|---|
| HbA | 3.14 | 129.6 |
| αα-fumaryl Hb | 3.16 | 132.1 |
| (Propyl-PEG5K)$_6$-Hb | 5.40 | 659.2 |
| (Propyl-PEG5K)$_6$-αα-Hb | 6.56 | 1181.9 |

Molecular volume was calculated with an equation V = 4πR$^3$/3.
R is radius of the sample.

Figure 3:
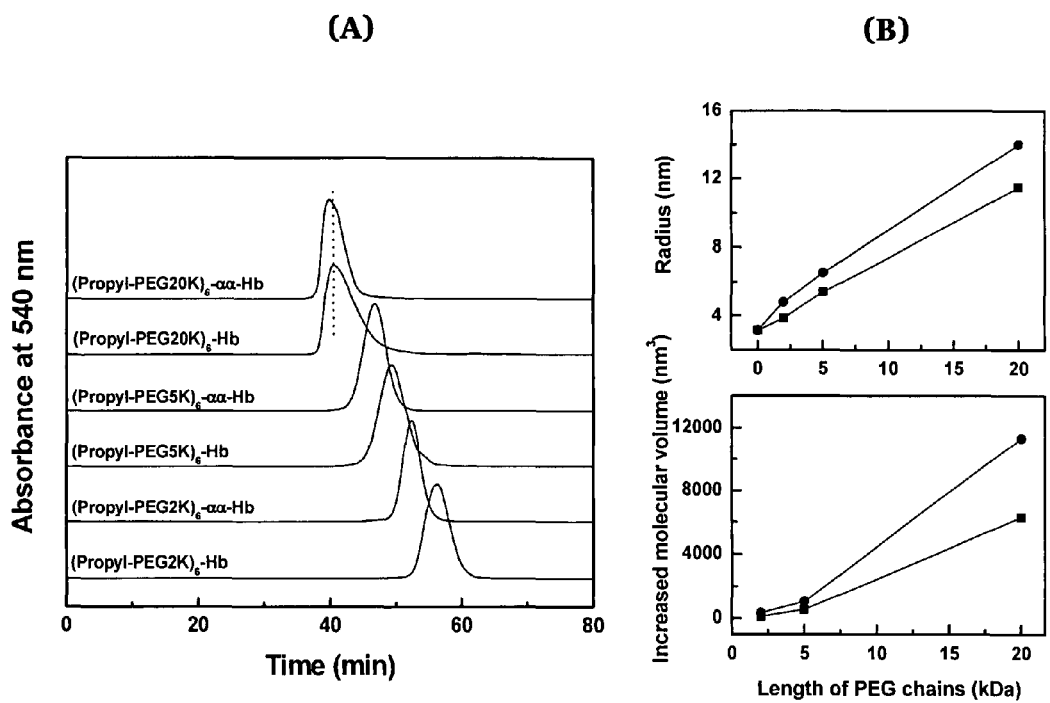
FIG. 3A-3B are graphs showing the influence of PEG-chain length on the molecular volume of PEGylated αα-fumaryl Hbs. Panel (A) shows a size exclusion chromatographic analysis of PEGylated protein. The analysis was carried out at room temperature on two HR 10/30 Superose 12 columns connected in series. The columns were eluted with PBS, pH 7.4 at a flow rate of 0.5 ml/min. Panel (B) shows the size enhancement of Hb (■) and αα-fumaryl Hb (●) as a function of the length of attached PEG chains. The curves were made by straight line placed between the points using the software Origin 6.0. Molecular radii were measured by dynamic light scattering at a protein concentration of 1 mg/ml. Increased molecular volume (ΔV) was calculated with an equation $\Delta V = 4\pi(R^3 - R_0^3)/3$. R and $R_0$ are radii of PEGylated Hbs and HbA, respectively.

Influence of PEG-chain Length on the Molecular Volume of PEGylated Proteins. PEG-2K and PEG-20K aldehyde are homologues of the PEG-5K aldehyde. To establish the effect of PEG-chain length on the hydrodynamic volume of PEGylated proteins, PEG-2K, PEG-5K and PEG-20K aldehyde were used for reductive alkylation of crosslinked and uncrosslinked Hb. The hydrodynamic volumes of PEGylated proteins were compared using SEC (FIG. 3A). PEGylation of crosslinked Hb using the three PEG reagents exhibited larger hydrodynamic volume than the respective PEGylated uncrosslinked Hbs.

FIG. 3B compares the increase in the molecular radius of Hb on PEGylation as a function of PEG-chain length. As the length of PEG chain is increased, the molecular radius of the PEGylated product is also increased. The molecular volumes of the three PEGylated αα-fumaryl Hb are nearly twice that of the corresponding PEGylated uncrosslinked Hb. Therefore, the influence of αα-fumaryl intramolecular crosslink on the propensity of PEGylation to enhance molecular volume of Hb is correlated with the PEG-chain length.

Figure 4:
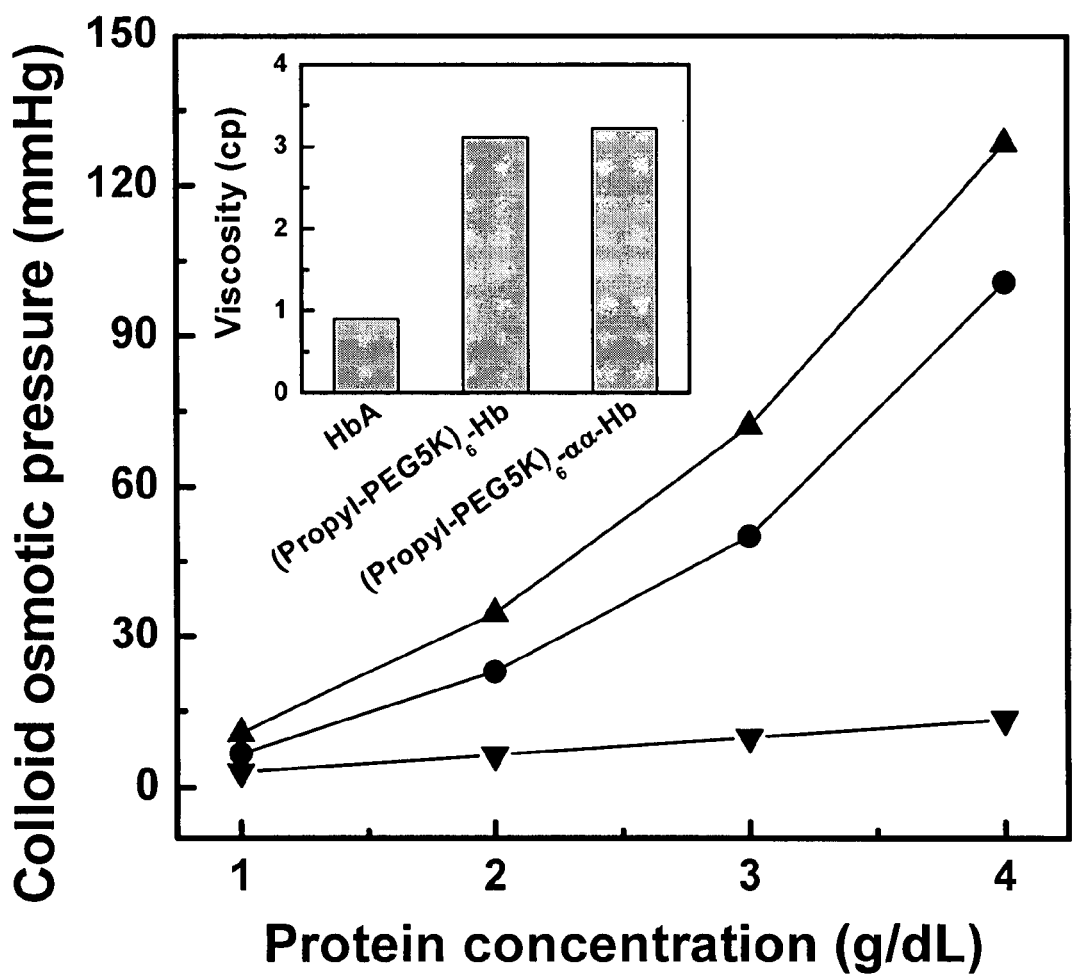
FIG. 4 is a graph showing colloidal osmotic pressures of HbA (■), (Propyl-PEG5K)$_6$-Hb (●), (Propyl-PEG5K)$_6$-αα-Hb (▲) as a function of protein concentration. A series of concentrations of HbA samples were measured by a Wescor 4420 Colloidal Osmometer in PBS (pH 7.4) at room temperature. The inset indicated the comparison of the viscosity of (Propyl-PEG5K)$_6$-αα-Hb with that of (Propyl-PEG5K)$_6$-Hb at 4 g/dL. The curves were made by straight line placed between the points using the software Origin 6.0.

Influence of αα-fumaryl Crossbridge on the Viscosity and COP of (Propyl-PEG5K)$_6$-Hb. The influence of αα-fumaryl intramolecular crosslinking on the viscosity and COP of PEGylated Hb is presented in FIG. 4. The COP of (Propyl-PEG5K)$_6$-αα-Hb exhibits a nonlinear dependence on the protein concentration. (Propyl-PEG5K)$_6$-αα-Hb exhibited lower COP value than (Propyl-PEG5K)$_6$-Hb for the entire range of the protein concentration, in spite of its larger molecular volume than (Propyl-PEG5K)$_6$-Hb. This result reflects that there are more colloidal particles in (Propyl-PEG5K)$_6$-Hb than that in (Propyl-PEG5K)$_6$-αα-Hb. The viscosity of (Propyl-PEG5K)$_6$-αα-Hb at a protein concentration of 4 g/dL has been compared with that of HbA and (Propyl-PEG5K)$_6$-Hb, and the results are presented in the inset (FIG. 4). The PEGylation induced increase in the viscosity of Hb is not essentially influenced by the αα-fumaryl intramolecular crossbridge. These influences as a consequence of intramolecular crosslinks could be due to dissociation of uncrosslinked Hb tetramers to dimers upon PEGylation.

Figure 5:
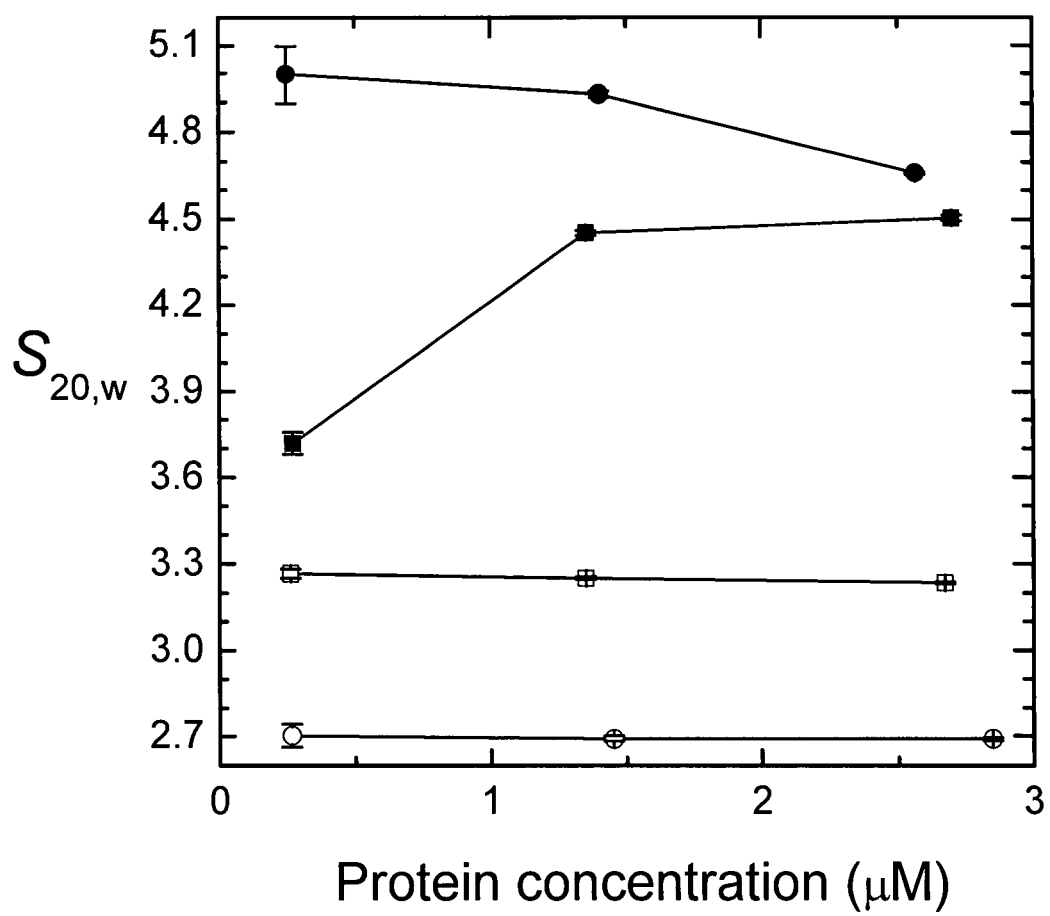
FIG. 5 shows measurements of S20, W of PEGylated proteins as a function of hemoglobin concentrations. Sedimentation velocity measurements of (Propyl-PEG5K)$_6$-Hb (□), (Propyl-PEG5K)$_6$-αα-fumaryl Hb (○), HbA (■) and αα-fumaryl Hb (●) were conducted in a Beckman XL-I analytical ultracentrifuge in PBS buffer at pH 7.4, 25° C. and 55,000 rpm. Boundary movement was followed at 405 nm using the centrifuge's absorption optics. The curves were made by straight line placed between the points using the software Origin 6.0.

Analytical Ultracentrifugation. Sedimentation velocity studies of crosslinked and uncrosslinked PEGylated Hb and crosslinked and uncrosslinked Hb were conducted to gain more insight into the effect of PEGylation on the dimer-tetramer association of Hb (FIG. 5). Three of the four molecules show the decrease in sedimentation coefficient (S) with increasing protein concentration characteristic of monodisperse particles (●, ○, □); only uncrosslinked Hb shows the increase in S with protein concentration characteristic of self-association (■). The molecular weight of (Propyl-PEG5K)$_6$-αα-Hb estimated from S° 20, w/D° 20, w is ~90 kDa, consistent with a hexaPEGylated tetramer (○). Crosslinked but otherwise unmodified HbA sediments as a monodisperse particle (●) whose estimated molecular weight of ~55 kDa is also consistent with a tetramer. The sedimentation rate of (Propyl-PEG5K)$_6$-Hb is slower; the molecular weight estimated for this particle is ~60 kDa, consistent with predominantly PEGylated Hb dimers (□). From these data we conclude that PEGylation destabilizes the Hb tetramer. The slow sedimentation of (Propyl-PEG5K)$_6$-Hb and (Propyl-PEG5K)$_6$-αα-Hb relative to the unmodified proteins indicates that PEGylation introduces hydrodynamic drag that can be envisaged as a 'parachute' impeding transport of the modified proteins (Dhalluin et al., 2005). This conclusion is consistent with the diffusion constants measured for the two crosslinked Hb molecules. D20, w values of 8.1±2.4 and 4.3±2.0 Ficks were measured for αα-fumaryl Hb and (Propyl-PEG5K)$_6$-αα-Hb, respectively, at the highest protein concentrations analyzed (FIG. 5).

Figure 6:
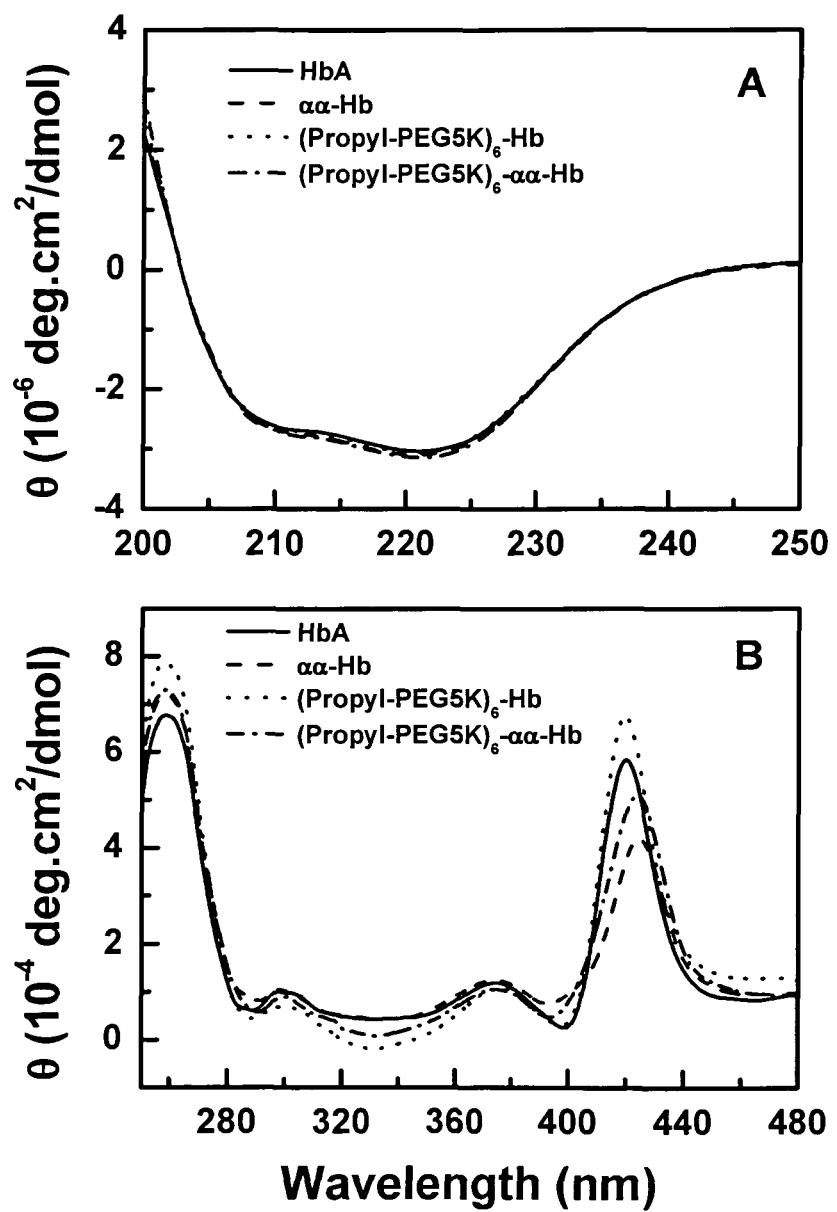
FIG. 6A-6B shows circular dichroism spectra of PEGylated proteins. Circular dichroism spectra of HbA (red line), αα-fumaryl Hb (green line), (Propyl-PEG5K)$_6$-Hb (blue line) and (Propyl-PEG5K)$_6$-αα-Hb (black line) were recorded at 25° C. with a 0.2-cm light path cuvette (310 μl) in the far-UV region (200-250 nm, A), near-UV and Soret region (250-480 nm, B). The molar ellipticity, θ, is expressed in deg.cm2/dmol on a heme basis.

Influence of αα-Fumaryl Intramolecular Crossbridge on Structural Features of (Propyl-PEG5K)$_6$-Hb. (i) CD Measurements. The structural features of (Propyl-PEG5K)$_6$-Hb and (Propyl-PEG5K)$_6$-αα-Hb have been investigated using circular dichroism (CD) spectroscopy. The far-UV (absorbance 200-250 nm) CD spectra for the PEGylated proteins are shown in FIG. 6A. As indicated by the ellipticity values at 222 nm, the α-helical content of HbA was not changed upon the introduction of αα-fumaryl crossbridge and/or PEGylation. Thus, the secondary structure of HbA was not influenced either by αα-fumaryl crossbridge or subsequent PEGylation.

In the near-UV CD region (FIG. 6B), the L-band (centered around 260 nm) is considered to be sensitive to the interactions between the heme and the surrounding globin, being influenced by the attached ligand (Zentz et al., 1994). PEGylation of HbA induced an increase in the intensity of L band, while PEGylation of αα-fumaryl Hb showed no change in the ellipticity of L band. This indicates that the increased intensity of the L band of HbA upon PEGylation was not related to PEGylation itself; but related to PEGylation induced structural changes of HbA, the dissociation of Hb tetramer. The region around 285 nm is considered as indicative of the R to T transition, and correlated to the environment of α42 and β37 aromatic residues in HbA (Perutz et al., 1974). PEGytation of HbA and αα-fumaryl Hb both induced a decrease in the ellipticity around 285 nm (Perutz et al., 1974), possibly due to the PEGylation induced conformational change around α42 and β37 that reflects the α1β32 subunit interface contact domain. Thus, the PEG shell of the PEGylated Hb appears to reduce the propensity of the molecule to transition from R to T state, consistent with the fact that PEGylation increases the oxygen affinity of Hb (Hu et al., 2005).

The Soret band of Hb is informative on the interactions of heme prosthetic group with the surrounding aromatic residues and to modifications in the spatial orientation of these amino acids with respect to heme, affecting porphyrin transitions and π-π* transitions in the surrounding aromatic residues (Hsu and Woody, 1971). The presence of the αα-fumaryl intramolecular crosslink reduces the intensity of the Soret band of HbA with a wavelength shift to the red. This represents the presence of deoxy-like features in the αα-fumaryl crosslinked Hb. PEGytation of Hb increases the intensity of the Soret band without noticeable changes in the wavelength. This reflects that the microenvironment of heme is perturbed upon PEGylation (Hu et al., 2005). The hexaPEGylation of αα-fumaryl Hb slightly decreases the intensity of the Soret band, but the intensity is significantly lower than that of (Propyl-PEG5K)$_6$-Hb. The red shift in the Soret band induced as a result of the αα-fumaryl crosslinking is conserved even on PEGylation, which is considered as the reflection of the lower affinity of heme to oxygen (Perutz et al., 1974).

Figure 7:
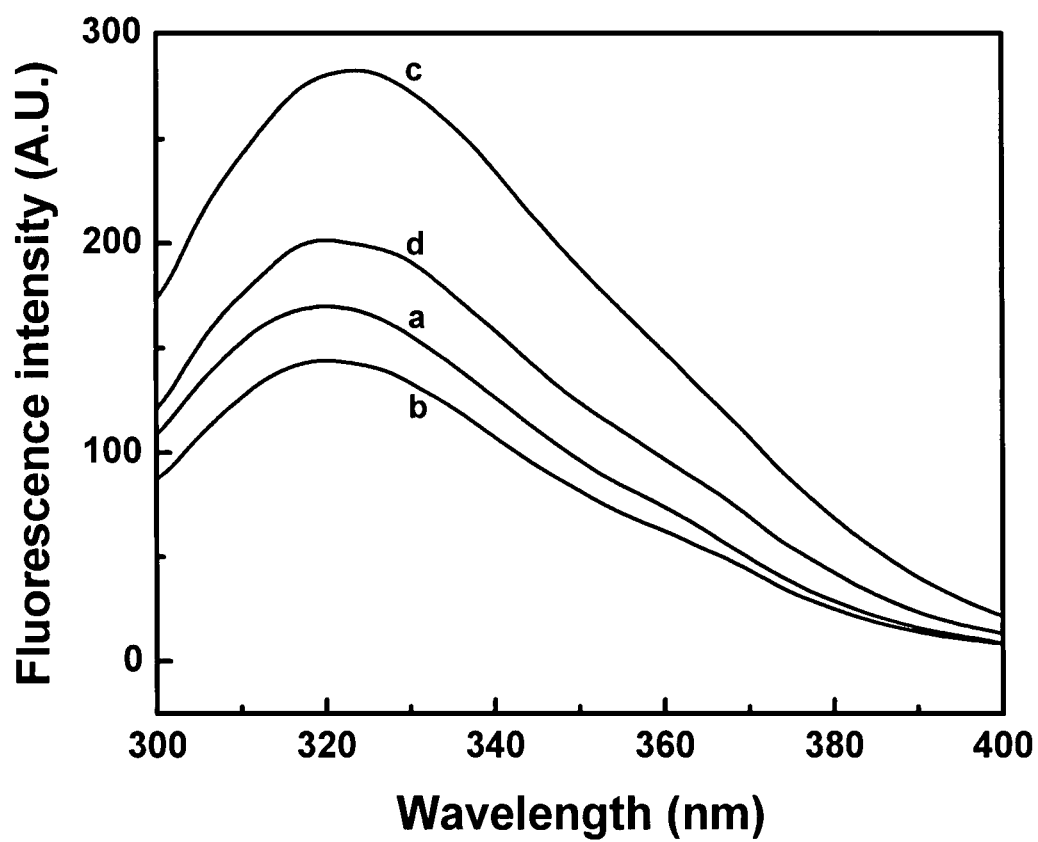
FIG. 7 shows intrinsic fluorescence emission spectra of HbA (α), αα-fumaryl Hb (b), (Propyl-PEG5K)$_6$-Hb (c) and (Propyl-PEG5K)$_6$-αα-Hb (d). The excitation wavelength was 280 nm. The measurements were performed using Shimadzu spectrofluorimeter at room temperature. All the samples used were at Hb concentration of 5.7 mg/ml in PBS, pH 7.4.

(ii) Front-face Fluorescence Measurements. Intrinsic fluorescence of Hb is primarily due to the fluorescence of Trp-37 (β) at the α1β2 interface, which reflects the stability of the quaternary structure of Hb (Hirsch, 2003). When excited at 280 nm, the fluorescence intensity of HbA decreased as a result of αα-fumaryl intramolecular crosslinking with a peak position at 320 nm (FIG. 7). However, the fluorescence intensity of HbA on PEGylation is significantly increased (66.3%) and exhibits a noticeable red-shifted peak position (3 nm), which reflects the perturbation of the quaternary structure of Hb. Compared with (Propyl-PEG5K)$_6$-Hb, the fluorescence intensity of (Propyl-PEG5K)$_6$-αα-Hb decreased (28.7%) with a blue shift to 320 nm, indicating that αα-fumaryl intramolecular crosslinking could reduce the perturbation of the quaternary structure of PEGylated uncrosslinked Hb. In conjunction with the sedimentation velocity studies, this may be considered as a reflection of the enhanced dissociation of the tetramers (reflection of the presence of dimers), and inhibition of such dissociation by αα-fumaryl intramolecular crosslink.

Influence of Engineering ββ-succunimidopehyl PEG-2000 Intramolecular Cross-bridge on the Molecular Properties of (Propyl-PEG5K)$_6$-Hb. The central cavity of Hb plays a dominant role in dictating the structural stability and functional properties of Hb. The influence of the αα-fumaryl crossbridge on the molecular properties of (Propyl-PEG5K)$_6$-Hb may be unique, as it is an αα-crosslink within the central cavity. In an attempt to establish the fact that the observed influence on the molecular properties of (Propyl-PEG5K)$_6$-Hb is a consequence of an intramolecular crosslink, we have asked the question whether a crosslink outside the central cavity of Hb still works. ββ-succinimidophenyl PEG-2000 intramolecular crosslink at Cys-93(β) was also engineered into (Propyl-PEG5K)$_6$-Hb to provide an answer to this question. As shown in Table 3, modulation of the molecular properties by the presence of ββ-crosslink in (Propyl-PEG5K)$_6$-Hb nearly parallels to that by αα-fumaryl intramolecular cross-linking. The molecular radius and the molecular volume were increased. Viscosity was limitedly influenced, but the COP of (Propyl-PEG5K)$_6$-Hb decreased upon ββ-crosslinking. Therefore, ββ-crosslinking of (Propyl-PEG5K)$_6$-Hb also achieves the same results as the αα-crosslinking, apparently by preventing the PEGylated Hb tetramers from dissociating into dimers.

TABLE 3

Comparison of the Solution properties of Hexa PEGylated Hbs

| | Radius (nm) | Molecular Volume (nm$^3$) | COP (mmHg) | Viscosity (cp) |
|---|---|---|---|---|
| (Propyl-PEG5K)$_6$-Hb | 5.40 | 659.2 | 128.5 | 3.11 |
| (Propyl-PEG5K)$_6$-αα-Hb | 6.56 | 1181.9 | 100.8 | 3.23 |
| (Propyl-PEG5K)$_6$-ββ-Hb | 6.70 | 1259.2 | 85.2 | 2.97 |

Samples for viscosity and COP measurements were at a Hb concentration of 4 g %. Samples for radius measurement were at a Hb concentration of 4 g %. Molecular volume was calculated with an equation V = 4πR$^3$/3.
R is radius of the sample.

It is surprising that the COP, the molecular radius and hydrodynamic volume of (Propyl-PEG5K)$_6$-ββ-Hb are slightly lower than those of (Propyl-PEG5K)$_6$-αα-Hb. This suggests that ββ-crosslinking used here is more efficient in reducing the number of dimers than αα-crosslinking. However, this is not the correct molecular explanation since ββ- and αα-crosslinked Hbs in the present study are essentially homogeneous. Accordingly, the number of PEGylated particles in the two PEGylated crosslinked Hbs should be same, and their COP, the molecular radius and hydrodynamic volume should be comparable to one another. However, it should be noted that the cross-linker in ββ-crosslinked Hb is long and flexible outside the central cavity of Hb, whereas that in αα-fumaryl Hb is short and rigid within the central cavity of Hb. The hexaPEGylated Hb tetramers with weakened interactions between the dimers can be held together loosely by the ββ-crosslinker, whereas those can be held tightly in αα-crosslinked Hb. Therefore, the long and flexible αβ-succinimidophenyl PEG-2000 linker can increase the molecular radius and hydrodynamic volume of (Propyl-PEG5K)$_6$-ββ-Hb, as compared with those of (Propyl-PEG5K)$_6$-αα-Hb. The lower COP of (Propyl-PEG5K)$_6$-ββ-Hb reflects that the PEG shell around (Propyl-PEG5K)$_6$-ββ-Hb is less compact than that around (Propyl-PEG5K)$_6$-αα-Hb, and its possible consequence on the packaging of the PEG in the PEG-shell. This molecular aspect of the two PEGylated crosslinked Hbs needs to be established by further comparative biophysical analysis.

Influence of Intramolecular Crosslinking on the Oxygen Affinity of PEGylated Hb. HexaPEGylation of Hb increases its oxygen affinity (lower the P50), and the P50 decreased from the control value of 11.8 to 6.3 mmHg (Table 4). The presence of mid central cavity αα-fumaryl crossbridge decreased the oxygen affinity of the PEGylated Hb. The P50 increased from 6.3 to 16.0 mmHg. Nonetheless, it should be noted that P50 value of αα-fumaryl Hb is considerably higher (lower oxygen affinity) than that of hexaPEGylated αα-fumaryl Hb. The intrinsic propensity of hexaPEGylation of Hb to increase the oxygen affinity of Hb is seen even with αα-fumaryl Hb. However, the P50 of HbA decreased to 6.3 mmHg from the control value of 11.8 mmHg as a result of the presence of outside the central cavity crosslink, ββ-crosslinking at Cys-93(β). HexaPEGylation of ββ-Hb decreased its P50 to 5.9 mmHg, indicating that the P50 of ββ-Hb was not significantly influenced upon PEGylation. On the other hand, the Hill coefficients of HbA, αα-fumaryl Hb and ββ-Hb are all decreased upon PEGylation, while that of PEGylated αα-fumaryl Hb is the lowest. Therefore, the consequence of the two different crosslinks on the oxygen affinity is very distinct, even though both influenced the PEGylation induced molecular properties at the same level.

TABLE 4

Oxygen binding properties of PEGylated proteins

| Sample | P$_{50}$[1] | n[2] |
|---|---|---|
| HbA | 11.8 | 2.8 |
| αα-fumaryl-Hb | 30.5 | 2.4 |
| ββ-Hb | 6.3 | 2.1 |
| (Propyl-PEG5K)$_6$-Hb | 6.3 | 1.9 |
| (Propyl-PEG5K)$_6$-αα-Hb | 16.0 | 1.5 |
| (Propyl-PEG5K)$_6$-ββ-Hb | 5.9 | 1.9 |

[1]Partial oxygen pressure at half saturation, in mmHg;
[2]Hill coefficient. Oxygen equilibrium curves of the samples were measured using Hem-o-scan at 37° C. in PBS, pH 7.4.

Discussion

PEGylation of Hb overcomes the vasoactivity of acellular Hb by making the vasoconstrictive Hb molecule into a vasodilator. PEG-Hb conjugate as a vasodilator is essentially a consequence of PEGylation induced molecular properties of the conjugate (Conover et al., 1999). The efficiency of albumin as a plasma volume expander is also significantly enhanced on PEGylation, which induces some new clinical properties to albumin (Cabrales et al., 2005). However, it was seen that PEGylated Hb has a higher COP than PEGylated albumin, even though their molecular masses were comparable (unpublished results). This observation prompted an investigation to determine whether the introduction of an intramolecular crosslink into Hb affected the molecular, structural and functional properties of PEGylated Hb.

The major finding of the present work is that PEGylated uncrosslinked Hb generated by reductive alkylation chemistry predominantly exits as dimers. When the dimers are held together as tetramers by intramolecular cross-links, the molecular, structural and functional properties of the PEGylated products are significantly changed.

The influence of the crosslinks on the molecular properties of the PEGylated Hb is reflected by the significantly enhanced molecular volume and the lower COP of (Propyl-PEG5K)$_6$-αα-Hb relative to (Propyl-PEG5K)$_6$-Hb, which makes the crosslinked Hb a better substrate in terms of new paradigms for the design of blood substitutes (Winslow, 2003). Due to the increase in the molecular volume, intramolecular cross-link in the PEGylated Hb will further reduce its extravasation rate. Besides, the lower COP makes it possible to use a higher concentration of Hb, without the possible dilution of the infused Hb by the increase in flow of fluids from the interstitial tissues to the vascular system. This has been the major limitation of the current versions of PEGylated Hbs in attempt to increase the level of tissue oxygenation. The absence of influence of intramolecular crosslinks on the viscosity of PEGylated Hb suggests that the viscosity of PEGylated Hb is a direct correlate of the PEG conjugated to protein (protein to PEG ratio).

The influence of the crosslinks on the structural properties of the PEGylated Hb is reflected by the CD spectra and fluorescence spectra of the products. The CD measurements reflect the perturbation of the heme environment of Hb upon PEGylation, and αα-fumaryl crosslink could decrease the perturbation. The fluorescence data suggest perturbation of the α1β2 interface of Hb by PEGylation, and a reduced effect of PEGylation on these structural aspects by the presence of αα-fumaryl crosslink. Thus, compared with the PEGylated Hb, the PEGylated crosslinked Hb is a better choice to develop as blood substitutes from the structural point of view.

The molecular basis for enhancing the dissociation of Hb tetramers into dimers upon PEGylation is also of interest from structural point of view. Typically, association of dimers into tetramers is driven primarily by formation of the α1β2 interface that involves more polar contacts between the C and N termini and the C-helices and FG corners of both subunits (Perutz, 1989). Since the complete modification of N-termini has taken place by the reductive alkylation chemistry, this can influence the interactions at both the αα-ends and the ββ-ends of central cavity. In addition, the association of αβ dimers to tetramers is facilitated by electrostatic attraction between positively charged α subunits and negatively charged β subunits (Perutz, 1989). The new hydrated PEG-shell around the protein core can also shield the charge of α and β subunits, which in turn can decrease the intersubunit electrostatic attractions. Further studies will be needed to delineate molecular basis of the increased dissociation of the PEGylated uncrosslinked Hb.

The influence of the crosslinks on the functional property of the PEGylated Hb has also been investigated here. The mid central cavity crosslink (αα-fumaryl crosslink) as well as crosslink outside the central cavity have similar influence on the molecular properties of PEGylated Hb. However, they exert very distinct influence on the oxygen affinity of PEGylated Hb. Preventing the dissociation of the PEGylated Hb into dimers does not significantly influence the oxygen affinity of the molecule, as reflected by the crosslink of PEGylated Hb outside the central cavity. On the other hand, αα-fumaryl cross-link that facilitates the retention of some deoxy like features of Hb in its oxy conformation helps to reduce the oxygen affinity of PEGylated Hb. Thus, if only the PEGylation induced molecular properties need to be modulated, one could use the crossbridge outside the central cavity of Hb, and if oxygen affinity of the PEGylated Hb also needs to be reduced besides the modulation of the molecular properties of the PEGylated Hb, αα-fumaryl crosslink will be the choice.

HexaPEGylated Hb generated by the extension arm facilitated PEGylation, (SP-PEG5K)$_6$-Hb exhibits a high oxygen affinity (Manjula et al., 2005; U.S. Pat. No. 5,585,484). The good flow properties of (SP-PEG5K)$_6$-Hb could be a consequence of the PEGylation induced molecular properties of Hb molecule (Tsai et al., 2004a) or the high oxygen affinity of the molecule (Winslow, 2003) or a synergy of both of these components. The high oxygen affinity of (SP-PEG5K)$_6$-Hb has been attributed to the PEGylation at Cys-93(β). (Propyl-PEG5K)$_6$-Hb has high oxygen affinity, even though Cys-93 (β) is not PEGylated (Hu et al., 2005), and reductive alkylation of HbA by glyceraldehyde, a low molecular weight analogue to PEG5K-aldehyde only slightly increase the oxygen affinity of Hb (Data not shown). This leads to the suggestion that the high oxygen affinity of PEGylated Hb is induced by PEG-shell surrounding Hb. In addition, PEGylation of recombinant Hb in which Cys-93(β) is mutated to Ala also results in the generation of PEGylated Hb with high oxygen affinity (Li et al., 2007). Thus, a common molecular mechanism involved in increasing the oxygen affinity of Hb may be through surface decoration of Hb with PEG-chains. The propensity of the αα-fumaryl crossbridge to lower the oxygen affinity of (Propyl-PEG5K)$_6$-Hb suggests that the high oxygen affinity of PEGylated Hb is a consequence of structural perturbations within the central cavity of Hb, and not a direct consequence of the enhanced dissociation of the PEGylated Hb tetramers into dimers.

The sedimentation velocity of Hb is reduced upon PEGylation even though the molecular mass of the conjugates is higher than that of the unmodified protein, due to the contribution of the PEG-shell around the protein core. As discussed previously, the conjugation of multiple copies of PEG-5K chains to Hb results in an enhancement in the molecular volume of the protein disproportionate to the mass of conjugated PEG; the PEG shell has a very low density of atoms relative to the protein core. The low density PEG shell behaves as a parachute, increasing the hydrodynamic drag and thus slowing down the conjugate's sedimentation velocity.

It is conceivable that PEG-chains exert a similar influence when the conjugated Hb is introduced into the circulatory system as blood substitute. In this situation the interaction of the PEG-chains with the endothelium at the blood tissue interface may provide an additional mechanical stimulus distinct from the shear stress developed on the endothelial surface that is a function of the local shear rate and the bulk viscosity of the medium. The potential role of PEGylation in providing an additional mechanism of interaction with the endothelium has important physiological/biological implications as it would lower the overall viscosity while maintaining the level of mechanical stimulation of the endothelium necessary for mechano transduction mediated homeostasis. A direct practical consequence of theses findings is helpful for the development of these PEGylated proteins as new and effective blood substitutes.

Example 2

Combining the Influence of Two Low O$_2$-Affinity Inducing Chemical Modifications of the Central Cavity of Hemoglobin Example Summary HexaPEGylated Hb, a non-hypertensive Hb, exhibits high O$_2$-affinity which makes it difficult to deliver desired levels of oxygen to tissue. PEGylation of very low O$_2$-affinity Hbs is now contemplated as the strategy to generate PEGylated Hbs with intermediate levels of O$_2$-affinity. Towards this goal, a doubly modified Hb with very low O$_2$-affinity has been generated. The amino terminal of β-chain of HbA is modified by 2-hydroxy, 3-phospho propylation first to generate a low oxygen affinity Hb, HPPr-HbA. The oxygen affinity of this Hb is insensitive to DPG and IHP. Molecular modeling studies indicated potential interactions between the covalently linked phosphate group and Lys-82 of the trans β-chain. To further modulate the oxygen affinity of Hb, the αα-fumaryl cross-bridge has been introduced into HPPr-HbA in the mid central cavity. The doubly modified HbA (αα-fumaryl-HPPr-HbA) exhibits an $O_2$-affinity lower than that of either of the singly modified Hbs, with a partial additivity of the two modifications. The geminate recombination and the visible resonance Raman spectra of the photoproduct of αα-fumaryl-HPPr-HbA also reflect a degree of additive influence of each of these modifications. The two modifications induced a synergistic influence on the chemical reactivity of Cys-93(β). It is suggested that the doubly modified Hb has accessed the low affinity T-state that is non-responsive to effectors. The doubly modified Hb is considered as a potential candidate for generating PEGylated Hbs with an $O_2$-affinity comparable to that of erythrocytes for developing blood substitutes.

Abbreviations: ACN, acetonitrile; DBBF, bis dibromosalicyl fumarate; DPG, 2,3-diphosphoglycerate; GY, geminate yield; Hb-P, Hb-Presbyterian; HFBA, heptafluorobutyric acid; HPPr, 2-hydroxy 3-phospho propyl; IEF, Isoelectric focusing; IHP, inositol hexaphosphate; L35, 2-[4-(3,5-dichlorophenylureido)phenoxy]-2-methylpropionic acid; 4-PDS, 4,4'-dithiodipyridine; PEG, polyethylene glycol; RPHPLC, reverse phase high performance liquid chromatography Introduction Developing low $O_2$-affinity Hb has been the subject of considerable interest both in terms of understanding the structure-function correlation of Hb and for the development of Hb based oxygen carriers. Central cavity modifications such as crosslinking and affinity labeling of the effector binding domains of Hb has been the prominent approaches to reduce the $O_2$-affinity of Hb (Walder et al., 1980; Benesch and Benesch, 1981; Chatterjee et al., 1982; DiDonato et al., 1983; Chatterjee et al., 1986; Fantl et al., 1987). However, interest in such molecules has subsided since most of these potential Hb based oxygen carriers turned out to be vasoactive (Hess et al., 1993; Saxena et al., 1999; Lieberthal et al., 2002). The vasoactivity was considered to be a consequence of the NO scavenging activity of acellular Hb (Kim and Greenburg, 1997; Doherty et al., 1998; Kim and Greenburg, 2005). Design of mutant Hbs with reduced NO binding activity has been one of the approaches advanced to generate non-hypertensive Hb based oxygen carriers (Doherty et al., 1998; Eigh et al., 1996; Olson et al., 1997; Dou et al., 2002).

An alternate approach to overcome the vasoactivity of Hb advocates the induction of unique molecular properties of plasma volume expanders such as colloid osmotic pressure and viscosity into Hb. Conjugation of polyethylene glycol (PEG) chains to Hb appears to achieve this goal (Conover et al., 1996; Conover et al., 1997; Vandegriff et al., 2003; Acharya et al., 2005). A recent observation that surface decoration of Hb with six copies of PEG-5000 chains nearly neutralizes the vasoactivity of Hb validates the concept that PEGylation of Hb can be used as a way of generating nonhypertensive Hb (Acharya et al., 2005). Accordingly, PEGylated Hb employing different chemistry, thiolation-mediated maleimide chemistry (Acharya et al., 2005; Manjula et al., 2005), reductive alkylation (Hu et al., 2005), acylation (Li et al., unpublished results) and thiocarbamoylation (U.S. Pat. No. 7,144,989 B2) has been generated. All these modifications were directed to amino groups of Hb. The resultant PEGylated Hbs had an average of six copies of PEG chains conjugated at different sites of Hb. All these PEGylated Hbs had an increased $O_2$-affinity, irrespective of the chemistry of modification and sites of PEG conjugation (Acharya et al., 2005; Manjula et al., 2005; Hu et al., 2005).

Though high $O_2$-affinity of the PEGylated Hbs is considered as an advantageous factor in achieving the neutralization of the vasoactivity of Hb by reducing the amount of oxygen delivered on the arterial side of the microcirculatory system (Vandegriff et al., 2003; Winslow et al., 1998; Tsai et al., 2003; Tsai et al., 2004b), the $O_2$-affinity of the present versions of PEGylated Hbs appears to be too high to deliver adequate levels of oxygen to tissues. Accordingly, the use of low $O_2$-affinity Hbs instead of using normal adult human Hb has been investigated as substrates for the generation of PEGylated Hbs using the same protocols discussed above (Acharya et al., 2005; Manjula et al., 2005; Hu et al., 2005; U.S. Pat. No. 7,144,989 B2).

Recent studies of hexaPEGylation of αα-fumaryl Hb has generated a PEGylated Hb with an oxygen affinity (P50~14 mm of Hg) lower than that of hexaPEGylated Hb (P50~7 mm of Hg) (Example 1). HexaPEGylation of modified Hbs, with an oxygen affinity still lower than that of αα-fumaryl Hb, may be expected to facilitate the generation of very low oxygen affinity that is comparable to that of erythrocytes (P50~28 mm of Hg). Preparation of doubly modified Hbs is an approach to generate very low oxygen affinity Hbs that could be used as substrates for PEGylation to generate low oxygen affinity PEGylated Hbs.

Introduction of negative charges at the amino terminal of β-chain induces low oxygen affinity to Hb (DiDonato et al., 1983; Acharya et al., 1994; Benesch et al., 1973). While carboxymethylation ((DiDonato et al., 1983) and galacturonic acid (Acharya et al., 1994) modification introduce a carboxyl group at Val-1(β), pyridoxal phosphate modification (Benesch et al., 1973) adds a phosphate group at the same site. The influence of pyridoxal phosphate in reducing the oxygen affinity of Hb seems to be higher than carboxymethylation or galacturonic acid modification at Val-1(β), presumably due to the presence of a phosphate group. Glyceraldehyde-3-phosphate is similar to DPG in structure and site specific modification of Val-1(β) of Hb by this reagent will introduce two phosphate groups in the DPG binding site of Hb. This can induce low oxygen affinity to Hb similar to DPG. Therefore, in the present study, the use of glyceraldehyde-3-phosphate in the presence of sodium cyanoborohydride was explored to modify the α-amino group of Val-1(β). This reaction is carried out under oxy conditions as compared to the deoxy conditions used for the modification of Hb by pyridoxal phosphate (Benech et al., 1973).

The αα-fumaryl crossbridging in the mid central cavity of HbA is another structural modification that reduces the $O_2$-affinity of HbA. The reagent, bis dibromosalicyl fumarate (DBBF), introduces a crosslink between the ε-amino groups of Lys-99(α) of the central cavity only in the deoxy conformation (Chatterjee et al., 1986). Under oxy conditions, the same reagent introduces a crosslink between the ε-amino groups of Lys-82(β) residues of ββ-cleft and induces a high $O_2$-affinity to HbA (Chatterjee et al., 1982). The high conformational selectivity of the reaction of DBBF with HbA and the resulting distinct influence of the crosslinking on the $O_2$-affinity has been interpreted as the consequence of freezing in the oxy or deoxy conformation of the protein through crosslinking (Chatterjee et al., 1986; Fernandez et al., 2000). These crosslinking reactions have been used to stabilize the α1β2 interface that is weakened by structural modifications of Hb (Example 1; Kwiatkowski et al., 1998).

Introduction of more than one low $O_2$-affinity inducing chemical modifications into Hb, generating a doubly modified Hb, is the approach evaluated here to develop a very low $O_2$-affinity Hb. These chemical modifications may act additively or synergistically to generate a very low $O_2$-affinity Hb. Recently, the αα-fumaryl crossbridge was engineered into Hb Presbyterian (Hb-P), a low $O_2$-affinity mid central cavity mutant Hb (Manjula et al., 2001). The αα-fumaryl Hb-P exhibited a very low $O_2$-affinity. The two structural modifications, i.e. the Presbyterian mutation (Asn-108(β)→Lys), and αα-fumaryl crossbridging, exhibited a synergy in reducing the $O_2$-affinity of the molecule. Since the two structural modifications in this case were in the mid central cavity, the proximity of the two structural perturbations might have facilitated the synergy of the two modifications of Hb structure.

In an attempt to generate a very low oxygen affinity Hb by chemical modifications, the mid central cavity low oxygen affinity was introduced and is described herein. This modification induced an αα-fumaryl crossbridge into HPPr-HbA. Characterization of the doubly modified HbA and correlation of its oxygen binding properties, geminate rebinding, conformation of heme pocket in the R-state, and Cys-93(β) reactivity are presented in this study. These results are discussed in the light that R-state conformation of Hb represents a dynamic equilibrium between multiple R-state conformations. The linkage of the low $O_2$-affinity inducing perturbation of the mid central cavity with that of ββ-cleft is only additive and is distinct from the linkage of two mid central cavity perturbations studied earlier (Manjula et al., 2001). The possible application of these very low $O_r$ affinity Hbs in the generation of non-hypertensive lower oxygen affinity PEGylated Hbs is also discussed.

Materials and Methods

Preparation of HPPr-HbA. Purified HbA (0.5 mM) was modified with 5 mM glyceraldehyde-3-phosphate in the presence of 10 mM NaCNBH3 in PBS, pH 7.4, at 37° C. for 30 min. The product, HPPr-HbA, was purified on CM-52 cellulose (2.5×50 cm) using a gradient of 10 mM phosphate, pH 6.0 to 15 mM phosphate, pH 8.0. The peak corresponding to HPPr-HbA, as characterized by the isoelectric focusing of the peak, was further purified on the same column, using a shallower gradient.

Cross-linking of HPPr-HbA by DBBF. HPPr-HbA was modified with DBBF as described previously (Chatterjee et al., 1986). Briefly, HPPr-HbA (1 mM) was incubated with 8 mM sodium tripolyphosphate overnight at 4° C. to prevent the modification of DPG pocket residues by DBBF. This sample was deoxygenated at 37° C. and incubated with 2 mM DBBF at the same temperature for 4 h. The reaction was stopped by adding 20 mM Gly-Gly.

Analysis of αα-fumaryl crosslinking of HPPr-HbA. This analysis was carried out by reverse phase high performance liquid chromatography (RPHPLC) using a Vydac C4 column (4.6×250 mm). The same amount of hemoglobin samples were loaded in 0.3% heptafluorobutyric acid (HFBA) on C4 column equilibrated with 35% acetonitrile (ACN) containing 0.1% HFBA. The globin chains were eluted with a gradient of 35-45% ACN in the first 10 min and then 45-50% ACN in 90 min at a flow rate of 1 ml/min. HFBA (0.1%) was present in the solvents throughout the gradient.

Purification of αα-fumaryl-HPPr-HbA. On introducing αα-fumaryl-crosslinking into HPPr-HbA, the derivative developed some met Hb. Therefore, the derivative was reduced with dithionite as described by Roy and Acharya (1994). The oxy form of αα-fumaryl-HPPr-HbA was purified on Q-Sepharose High Performance (0.9×30 cm). The column was equilibrated with 50 mM Tris acetate, pH 8.0 and eluted with a linear gradient consisting of 200 ml each of buffer A (50 mM Tris acetate, pH 7.7) and buffer B (50 mM Tris acetate, pH 6.8 containing 25 mM NaCl).

Isoelectric focusing (IEF) of modified hemoglobins. Hemoglobin samples were analyzed on precast IEF agarose gels (PerkinElmer) containing resolve ampholytes pH 6-8. The gel was electrofocused (Isolab) for 1 h.

Mass spectrometry. The isolated globins of the modified Hbs were analyzed by ESI-MS on a 9.4 Tesla Fourier Transform Ion Cyclotron Resonance Mass Spectrometer (Varian, Inc.). The tryptic peptides of the globin chains were analyzed by LC/ESI-MS (33) using a C8 or C18 column (Vydac 1×50 mm). A stepwise gradient using 5% ACN containing 0.1% TFA as solvent A and 95% ACN containing 0.1% TFA as solvent B was generated to separate the peptides.

$O_2$-affinity measurements. The oxygen equilibrium measurements of modified Hbs were made at an Hb concentration of 0.5 mM, 37° C. in 50 mM Bis-Tris/50 mM Tris acetate, pH 7.4, using Hem-O-Scan (AMINCO). The measurements were made in the absence and presence of allosteric effectors at the concentrations indicated in Table 5.

TABLE 5

Oxygen affinity of αα-fumaryl-HPPr-HbA and its modulation by allosteric effectors

| Effector | HbA | HPPr-HbA | αα-fumaryl-HbA | αα-fumaryl-HPPr-HbA |
|---|---|---|---|---|
| None | 7.7 (2.6) | 24.5 (2.1) | 24.0 (2.5) | 48.5 (1.8) |
| 2.5 mM DPG | 19.5 (2.1) | 26.0 (1.8) | 45.0 (2.0) | 49.0 (1.7) |
| 2.5 mM IHP | 70.8 (1.4) | 28.5 (1.9) | 92.0 (1.0) | 48.5 (1.7) |
| 2.5 mM L35 | 63.0 (1.3) | 78.0 (1.4) | 48.5 (1.9) | 77.0 (1.1) |
| 1.0 M NaCl | 24.0 (2.3) | 36.0 (2.0) | 39.5 (2.0) | 51.5 (1.8) |
| 0.1 M NaCl | 13.0 (2.4) | 30.0 (2.0) | 29.5 (2.1) | 50.0 (1.6) |

Hill coefficient is given in parenthesis. In the measurements with P50 higher than 60 mmHg, Hb samples were not 100% oxygenated. These are some of the samples with IHP and L-35. In these cases cooperativity is also low. Therefore, the oxygenation values of Hbs at the maximum $pO_2$ (178 mmHg) were considered as 100% saturation in these experiments to determine the P50 values. These approximations underestimate the P50 values calculated.

Reactivity of Cys-93(β) of modified Hbs. The reactivity of Cys-93(β) of modified Hbs was determined by the reaction of Hb with 4,4'-dithiodipyridine (4-PDS) as described by Ampulski et al. (1969). Typically, the carbonmonoxy form of Hb (5 uM) was added to 50 μM 4-PDS in 50 mM Bis-Tris/Tris acetate, pH 7.4, at 30° C. The reaction kinetics was followed by monitoring the formation of the reaction product of 4-PDS, 4-thiopyridone, at 324 nm. The number of titrable thiol groups of Hb was determined from the initial concentration of Hb and the concentration of 4-thiopyridone formed at the end of the reaction.

Geminate Binding Studies. Geminate recombination of carbonmonoxide to 10 μs photoproducts of the carbonmonoxy forms of HbA and modified Hbs was determined as described by Khan et al (2001). All the samples used for the kinetic measurements were at 0.5 mM in heme in 50 mM Bis-Tris acetate, pH 6.5, at 3.5° C.

Visible Resonance Raman Studies. Visible RR spectra were generated for the 8 ns photoproducts of the CO derivatives of HbA and modified Hbs at 0.5 mM in heme in 50 mM Bis-Tris acetate, pH 6.5, at 3.5° C. (Khan et al., 2001).

Molecular Modeling. The high resolution crystal structure of hemoglobin, protein data bank code 4HHB (Fermi et al., 1984) was chosen for the initial model. The molecular model of αα-fumaryl cross-linked Hb was built as described by Chatterjee et al. (1986). The fumaryl chain was modeled using the builder module of Insight II® computer graphics (Accelrys Software Inc). The dihedrals of the side chains of both Lys-99 (α) were modified without affecting the main chain configuration such that a covalent fumaryl linkage is feasible between the two side chains. The backbone was kept intact and the lysine side chains were extended to accommodate the fumaryl linkage (Chatterjee et al., 1986). The modeling was done to have symmetric linkage with out Van der Waals overlap between the atoms of new group with the existing atoms of hemoglobin. The modified dihedral angles were also within reasonable limits.

The low resolution crystal structure protein data bank code 1B86 (Richard et al., 1993) was chosen for HPPr-HbA modeling. This deoxy structure contains the DPG. This would enable us to position the phosphates of HPPr group close to the DPG phosphate groups. The HPPr group linkage was modeled using both the builder module and biopolymer module. Efforts were made to bring the two phosphate groups close to the position of the phosphate groups of DPG bound within the ββ-cleft with no Van der Waals overlap. The dihedral angles were also within reasonable limits.

Results

Figure 8:
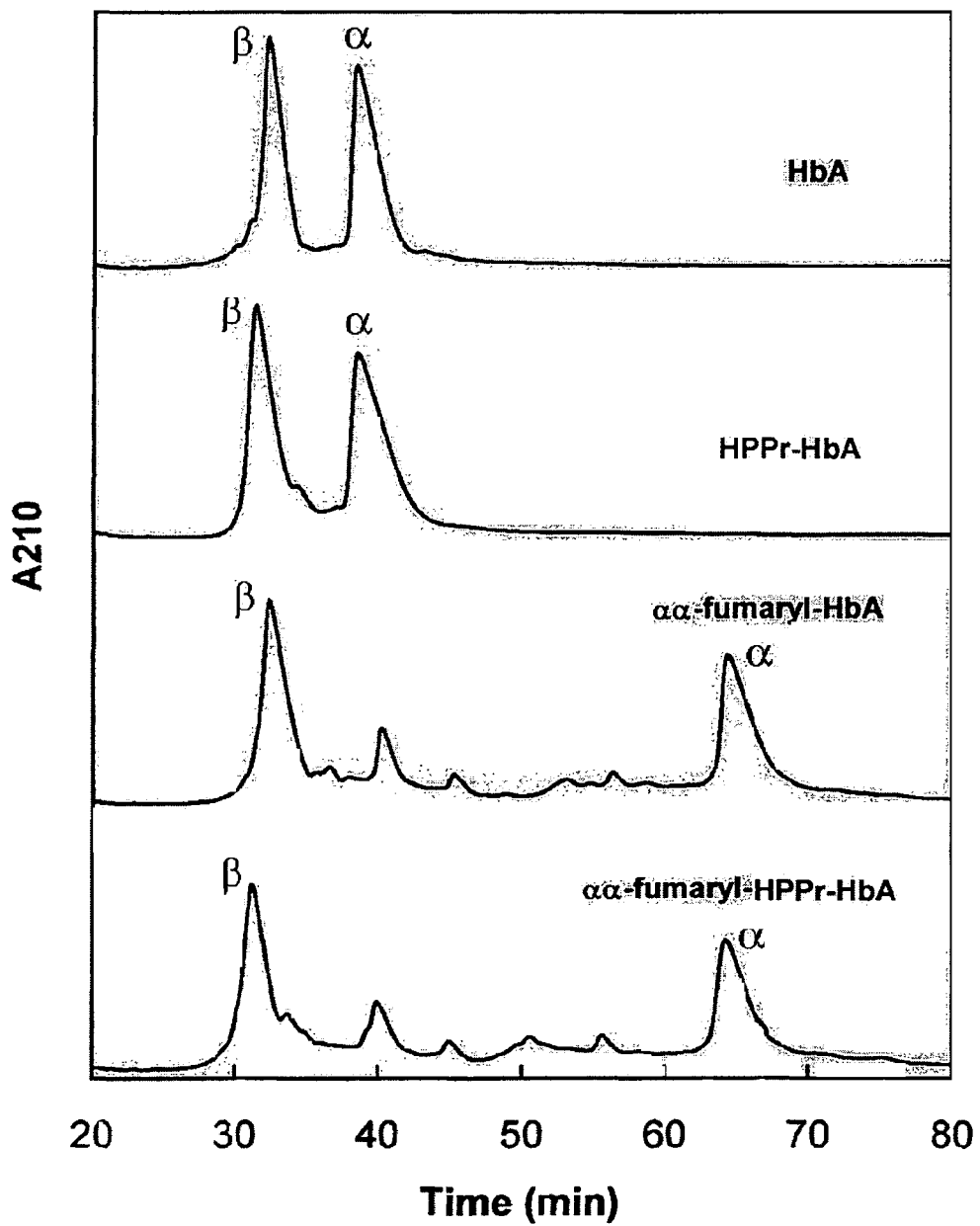
FIG. 8 is graphs of the RPHPLC of modified hemoglobins. The same amount of hemoglobin samples were loaded in 0.3% heptafluorobutyric acid (HFBA) on Vydac C4 column (4.6×250 mm) equilibrated with 35% acetonitrile (ACN) containing 0.1% HFBA. The globin chains were eluted with a gradient of 35-45% ACN in the first 10 min and then 45-50% ACN in 90 min at a flow rate of 1 ml/min. HFBA (0.1%) was present in the solvents throughout the gradient.
Figure 9:
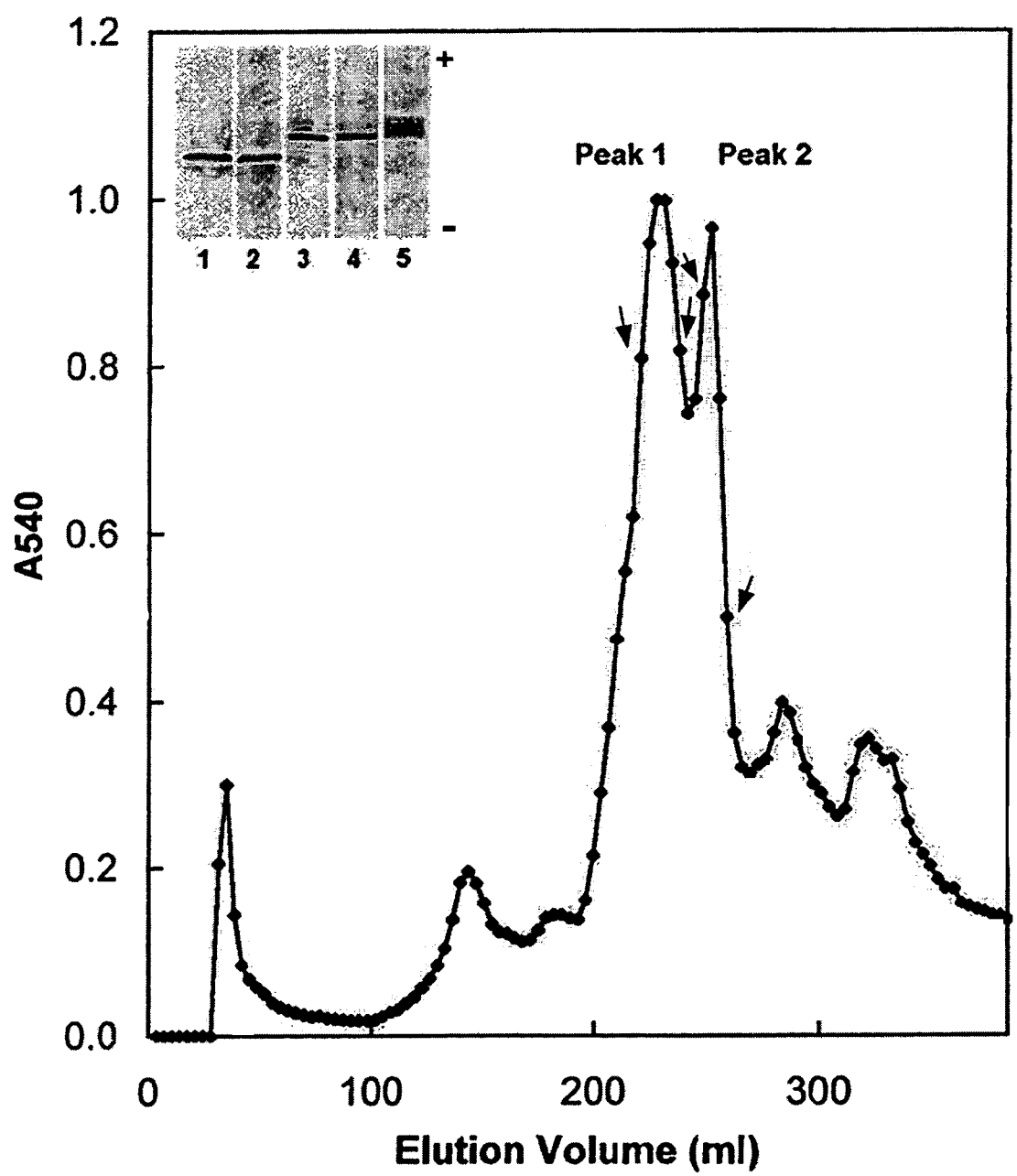
FIG. 9 is a graph and a photograph of an IEF gel showing the purification of αα-fumaryl-HPPr-HbA on a Q-sepharose High Performance column (0.9×30 cm). The column was equilibrated with 50 mM Tris acetate, pH 8.0 and eluted with a linear gradient consisting of 200 ml each of buffer A (50 mM Tris acetate, pH 7.7) and buffer B (50 mM Tris acetate, pH 6.8 containing 25 mM NaCl). The arrows indicate the fractions pooled from the peaks 1 and 2. Inset: IEF of modified hemoglobins: Lane 1, HbA; Lane 2, αα-fumaryl-HbA; Lane 3, HPPr-HbA; Lane 4 and 5, Peaks 1 and 2 from Q-sepharose chromatography of αα-fumaryl-HPPr-HbA, respectively. The + and − signs indicate the positions of the anode and cathode during electrofocusing.

Preparation and Characterization of αα-fumaryl-HPPr-HbA. The reactivity of HPPr-HbA to undergo αα-fumaryl cross-linking with DBBF under the conditions used for HbA was established by globin chain analysis of the reaction products by RPHPLC. As can be seen in FIG. 8, the RPHPLC profiles of the two reaction products are quite comparable and consist of uncross-linked β-globin and cross-linked α-globin as the two major products. These results indicated that the extent of cross-linking of HPPr-HbA by DBBF was comparable to that of HbA as reflected by the formation of αα-fumaryl globin (FIG. 8). The HPPr modification of Hb did not alter the reactivity of Lys-99(α) to form αα-fumaryl cross-linking.

αα-fumaryl-HPPr-HbA was purified by chromatography on Q-Sepharose High Performance. There were two major peaks in the chromatogram, labeled as Peak-1 and Peak-2 (FIG. 9). The IEF analysis of the peaks is shown in FIG. 9 inset. Peak-1 is homogeneous (Inset in FIG. 9, Lane 4) whereas Peak-2 is heterogeneous containing products that are more acidic than the Peak-1 component (Lane 5). Presumably, these are the products modified by DBBF at multiple sites. The fainter bands in Peak 1, corresponding to minor products, accounted for less than 5%. Therefore, Peak 1 was selected for all the further studies without further purification.

The IEF profile of αα-fumaryl-HPPr-HbA was compared with those of HbA, αα-fumaryl-HbA, and HPPr-HbA (FIG. 9, inset). As can be seen, HPPr-HbA (Lane 3) exhibited a lower isoelectric point than HbA (Lane 1). This is primarily due to the introduction of the negatively charged phosphate group at Val-1(β) and also due to the lowered pKa of the α-amino group of Val-1(β) as a result of its conversion into a secondary amine. In contrast, the isoelectric point of αα-fumaryl-HPPr-HbA (Lane 4) is comparable to that of HPPr-HbA (Lane 3), despite the loss of the positive charges of two of its α-amino groups due to the introduction of the αα-fumaryl crosslinking. This phenomenon is similar to that observed with the αα-fumaryl crosslinking of HbA (Lanes 1 and 2), a result consistent with the earlier reports (Chatterjee et al., 1986).

The two globin chains of αα-fumaryl-HPPr-HbA were analyzed by ESI mass spectrometry (Table 6). The mass of β-chain indicated that each β-chain is conjugated to only one HPPr moiety and no DBBF modification of the β-chain has taken place. On the other hand, the mass of the α-component established the crosslinking of two α-chains by only one fumaryl group and no signs of HPPr conjugation.

TABLE 6

The mass of globin chains of Hbs determined by ESI mass spectrometry

| | Molecular mass (Da) | | | |
|---|---|---|---|---|
| | α-component | | β-component | |
| Sample | Calculated | Measured | Calculated | Measured |
| HbA | 15126.4 | 15129.0 | 15867.2 | 15866.0 |
| HPPr-HbA | 15126.4 | 15129.0 | 16021.3 | 16020.0 |
| αα-fumaryl-HbA | 30332.8 | 30330.0 | 15867.2 | 15868.0 |
| αα-fumaryl-HPPr-HbA | 30332.8 | 30330.0 | 16021.3 | 16020.0 |

Figure 10A:
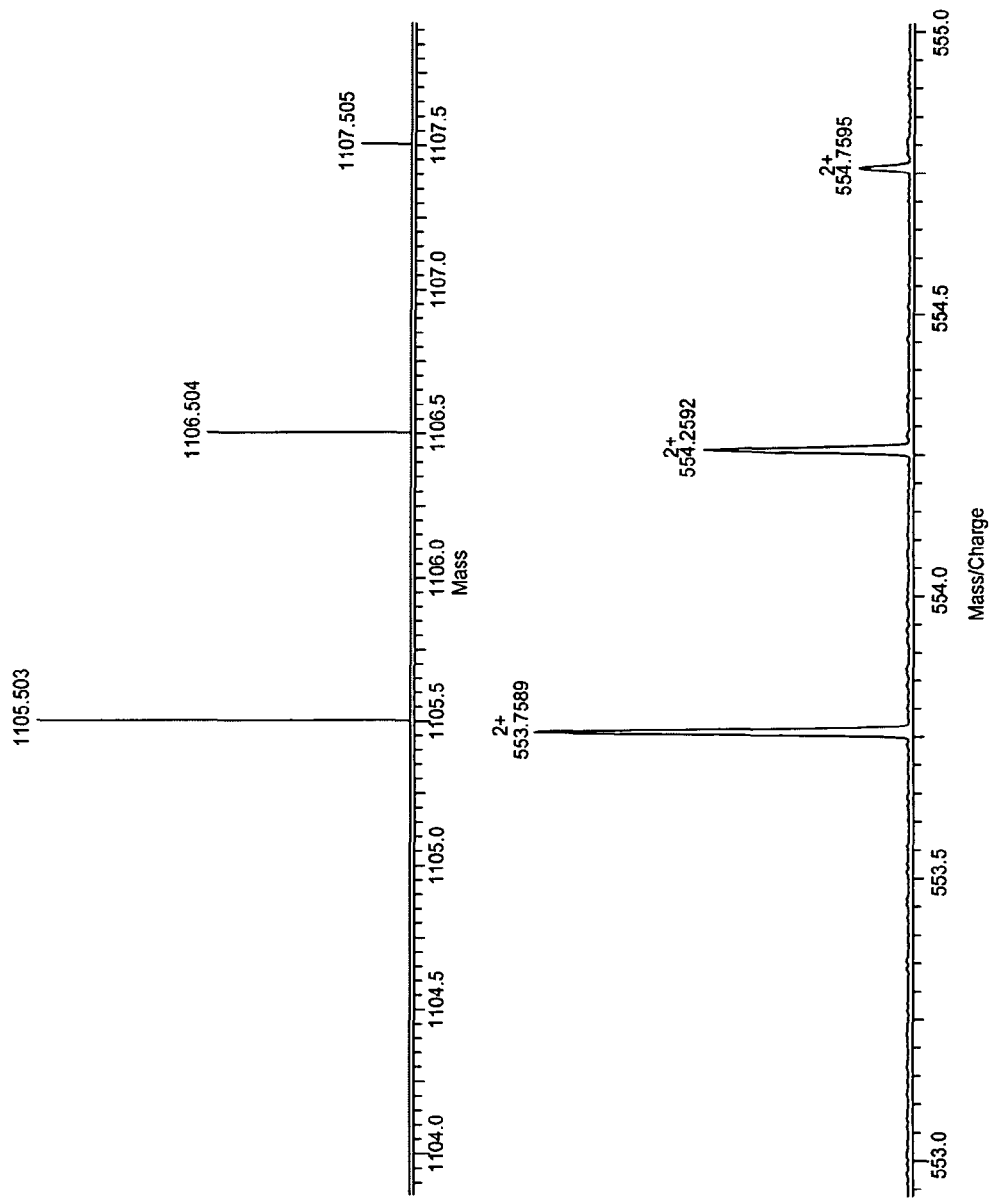
FIG. 10A-10B shows mass spectra of experimental hemoglobins. Panel A shows a mass spectrum of the G3P modified peptide of β-globin from αα-fumaryl-HPPr-HbA. The mass of this peptide corresponds to HPPr conjugated to the peptide comprising residues 1-8 of β-globin. Panel B shows a mass spectrum of the fumaryl cross-linked peptide of the crosslinked α-globin from αα-fumaryl-HPPr-HbA. The mass of this peptide corresponds to two copies of peptide spanning the residues 93-127 of α-globin cross-linked by a fumaryl group. The absence of cleavage at Lys-99(α) by trypsin is a consequence is apparently a consequence of the covalent attachment of the ε-amino group of this moiety to fumaryl moiety.

To further characterize the sites of modification in the doubly modified Hb, the modified α and β globins were digested with trypsin and the tryptic peptides were analyzed by LC/MS. The masses of all the peptides of the modified β-globin matched with that of the control β-globin, except for one peptide that corresponded to the residues 1 to 8 of β-chain. The peptide 1-8 carried an excess mass of 154 Da than the control peptide (FIG. 10A). This mass corresponds to the mass of HPPr moiety that has been conjugated to the β-globin. This establishes that G3P has modified the amino terminal of β-chain, site specifically in the doubly modified Hb.

Figure 10B:
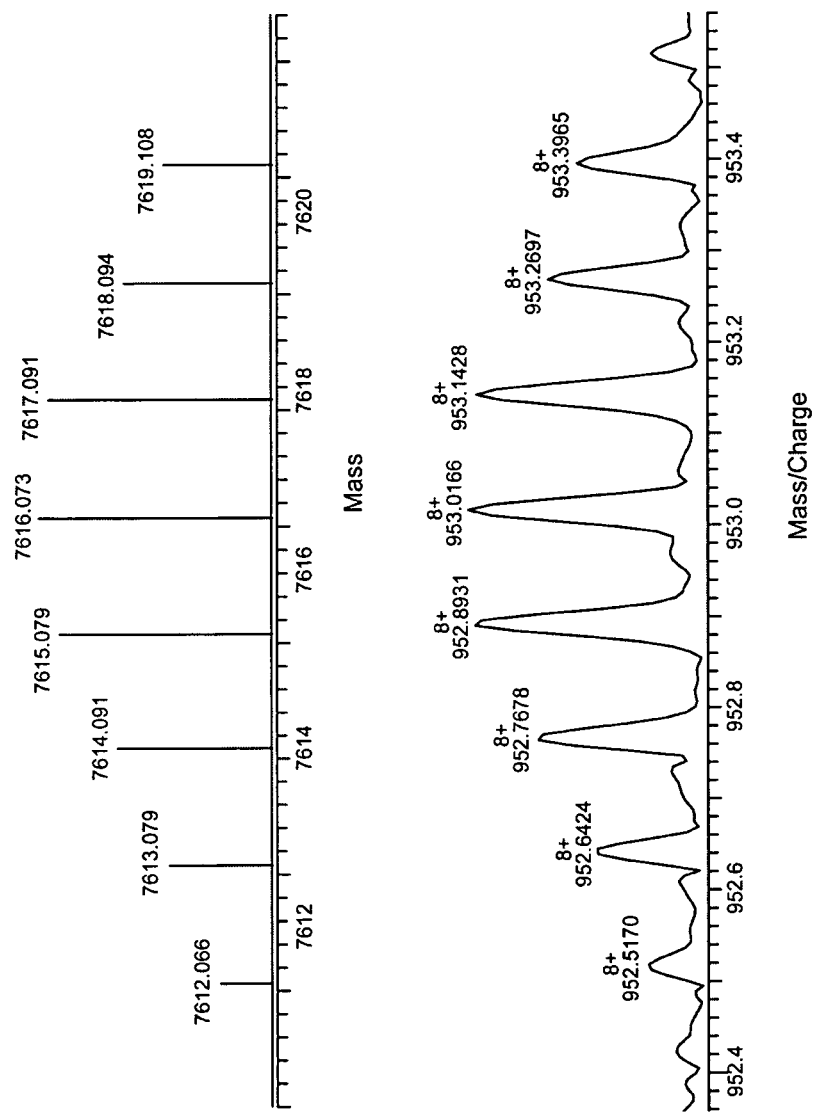

A comparison of the masses of the tryptic peptides of the modified α-globin with that of the control revealed the appearance of a new peptide carrying a mass of 7612.056 Da (FIG. 10B). This mass matched with the contiguous segment 93-127 of α-globin cross-linked by a fumaryl group. Thus, αα-fumaryl-HPPr-HbA carries an HPPr moiety at the amino terminal of β-chain and a fumaryl crosslink at Lys-99 of the α-chains.

Functional studies of αα-fumaryl-HPPr-HbA. The $O_2$-affinity of HbA was lowered nearly to the same degree by both of the modifications studied. The $O_2$-affinity of HPPr-HbA and αα-fumaryl-HbA were about three times lower than that of HbA. The $O_2$-affinity of the doubly modified HbA, αα-fumaryl-HPPr-HbA, was about six fold lower than that of HbA (Table 5). Thus, αα-fumaryl crosslinking reduced the $O_2$-affinity of HbA 3-fold and that of HPPr-HbA only 2-fold. Therefore, the influence of HPPr modification and of αα-fumaryl crosslinking of HbA on its $O_2$-affinity appears to be partially additive. The lowering of the $O_2$-affinity was accompanied by a small reduction in the Hill coefficient.

Modulation of the $O_2$-affinity of αα-fumaryl-HPPr-HbA by Allosteric Effectors. The $O_2$-affinity of the Hb derivatives has been studied in the presence of 0.1 M and 1.0 M NaCl. The derivatives with a single modification, HPPr-HbA and αα-fumaryl-HbA, have retained some sensitivity to the presence of chloride, nearly to the same extent (Table 5). On the other hand, the $O_2$-affinity of αα-fumaryl-HPPr-HbA was insensitive to the presence of chloride, reflecting the additivity of chloride mediated reduction in the $O_2$-affinity of the two modifications. It may also be noted that the $O_2$-affinity of both HPPr-HbA and αα-fumaryl-HbA in the absence of chloride was comparable to that of HbA in the presence of 1.0 M chloride. The $O_2$-affinity of the two modified Hbs could be reduced further by 1.0 M chloride. The electrostatic modification of either of ββ-cleft or of the mid central cavity increases the propensity of Hb to access lower $O_2$-affinity conformation in the presence of chloride. The insensitivity of the doubly modified Hb to chloride suggests that the modulation of the $O_2$-affinity by the positive charge density of the central cavity has been completely neutralized by the presence of the two modifications.

The $O_2$-affinity of αα-fumaryl-HPPr-HbA was not influenced by the presence of 2,3-diphosphoglycerate (DPG) (Table 5). The $O_2$-affinity of HPPr-HbA was also insensitive to the presence of DPG. HPPr modification of Hb makes the molecule insensitive to the presence of DPG. The intrinsic $O_2$-affinity of HPPr-HbA was lower than that of HbA in the presence of DPG. Similarly, the intrinsic $O_2$-affinity of αα-fumaryl-HPPr-HbA was lower than the DPG modulated $O_2$-affinity of αα-fumaryl-HbA. The covalent attachment of phosphate group at the DPG pocket seems to stabilize the T-structure of tetramer better than the physiological modulator, DPG.

Although inositol hexaphosphate (IHP) is a stronger modulator of the $O_2$-affinity of HbA, like DPG, it had negligible effect on the $O_2$-affinity of HPPr-HbA and αα-fumaryl-HPPr-HbA. In contrast, IHP reduced the $O_2$-affinity of αα-fumaryl-HbA to a level greater than that observed with HbA. Thus, HPPr modification essentially desensitizes the influence of IHP to modulate the $O_2$-affinity of HbA as well as of αα-fumaryl-HbA.

The effect of the allosteric effector 2-[4-(3,5-dichlorophenylureido)phenoxy]-2-methylpropionic acid (L35) that binds at the αα-end of the central cavity (Lalezari et al., 1990) is quite opposite to that of DPG and IHP that bind at the ββ-cleft. L35 reduced the $O_2$-affinity of αα-fumaryl-HPPr-HbA to a level lower than that of HbA (Table 5). The intrinsic P50 of αα-fumaryl-HPPr-HbA was comparable to that of HPPr-HbA in the presence of L35. The $O_2$-affinity reducing potential of HPPr modification and that of L35 appears to act additively on HbA and on αα-fumaryl-HbA. This additivity is consistent with the report that the $O_2$-affinity reducing potential of DPG and/or IHP and that of L-35 are additive (Lalezari et al., 1990). On the other hand, αα-fumaryl crosslinking of HbA reduced the propensity of L35 to lower the $O_2$-affinity of HbA. The HPPr modification of αα-fumaryl-HbA overcomes the inhibitory activity of αα-fumaryl crossbridging on the L35 mediated reduction in the $O_2$-affinity of HbA.

Geminate recombination studies. The geminate recombination of CO to photodissociated products of modified Hbs was determined to understand the structure of the initial population of the derivatives in R state (Friedman, 1985; Friedman et al., 1985; Marden et al., 1987; Murphy et al., 1988; Friedman, 1994; Huang et al., 1999). The geminate yield of HPPr-HbA and αα-fumaryl-HbA was about 12 and 8% lower than of HbA (Table 7). The geminate yield of αα-fumaryl-HPPr-HbA was 20% lower than that of HbA, indicating that the two modifications made an additive impact on the structure of αα-fumaryl-HPPr-HbA. The geminate yield of HPPr-HbA was insensitive to IHP and lowered by L35. In contrast, the geminate yield of αα-fumaryl-HbA responded to IHP but was not influenced by L35. HPPr modification of αα-fumaryl-HbA neutralized the inhibitory influence of αα-crosslinking on L35 modulation, as was seen with the $O_2$-affinity.

TABLE 7

Percentage of geminate yield of modified Hbs

| Hb | No effectors | +IHP | +L35 | +IHP+L35 |
|---|---|---|---|---|
| HbA | 65 | 45 | 60 | 40 |
| HPPr-HbA | 57 | 57 | 52 | 52 |
| αα-fumaryl-HbA | 60 | 53 | 60 | 53 |
| αα-fumaryl-HPPr-HbA | 52 | 50 | 50 | 50 |

Hb concentration was 0.5 mM in heme.

TABLE 7-continued

Percentage of geminate yield of modified Hbs

| Hb | No effectors | +IHP | +L35 | +IHP+L35 |
|---|---|---|---|---|

IHP was added in 6 folds excess over tetramer concentration.
L35 was added in 4 folds excess over tetramer concentration.

Visible resonance Raman spectroscopy. Table 8 shows the influence of the chemical modification on the Fe-His stretching frequency of Hb, ν(Fe-His). It is clear that the correlation between the reduction in the frequency of ν(Fe-His) and that in GY is not operative across the board with respect to all the listed derivatives of Hb. Most notably, the decrease in frequency was less for the HPPr modification than it was for the αα-fumaryl modification and yet the GY was lower for the former. The absence of an absolute one to one correspondence between the two parameters is likely to arise from either one or two factors. The frequency of ν(Fe-His) has been correlated with the contribution to the kinetic barrier at the heme due to proximal strain (Friedman, 1985; Friedman et al., 1985; Friedman et al., 1983; Peterson and Friedman, 1998). Proximal effects are claimed to be a bigger factor for the α subunits whereas distal effects are supposed to dominate the rebinding for the β subunits (Mathews et al., 1989). Different modifications may impact the α and β subunits differently or have disparate effects on factors contributing to the GY, e.g. conformational mobility that facilitates ligand escape. Alternatively, as noted above, the relaxation of structure subsequent to photodissociation can influence the GY, whereas the given Raman frequency is reflective of the unrelaxed or minimally relaxed conformation. Differences in the GY could arise from differences in the conformational relaxation rates subsequent to photodissociation.

TABLE 8

Iron-proximal histidine stretching frequency of modified Hbs

| Hb | No effectors | +IHP | +L35 | +IHP+L35 |
|---|---|---|---|---|
| HbA | 230.0 | 228.0 | 228.5 | 225.0 |
| HPPr-HbA | 229.0 | 229.0 | 227.0 | 228.0 |
| αα-fumaryl-HbA | 227.0 | 225.5 | 226.0 | 224.0 |
| αα-fumaryl-HPPr-HbA | 226.0 | 226.0 | 225.3 | 226.0 |

All the values were given in wavenumber.
Hb concentration was 0.5 mM in heme.
IHP was added in 6 fold excess over tetramer concentration.
L35 was added in 4 fold excess over tetramer concentration.

Figure 11:
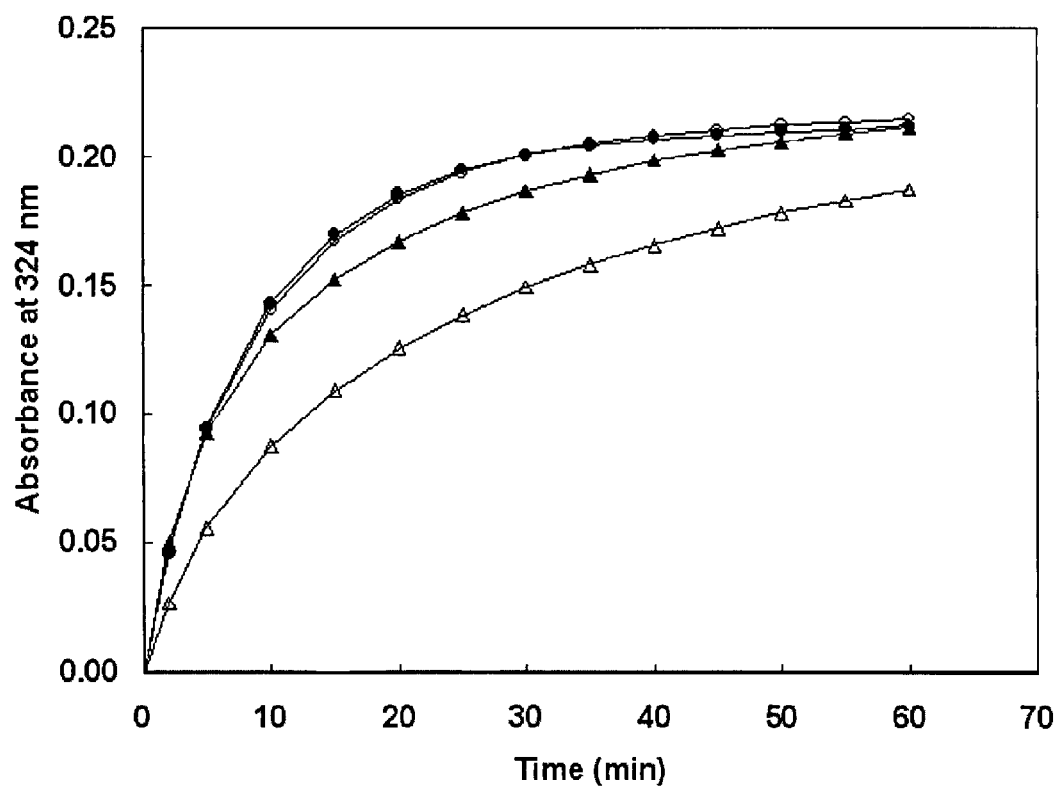
FIG. 11 is a graph showing kinetics of the reaction of modified hemoglobins with 4-PDS. Carbonmonoxy form of Hb (5 μM) was reacted with 50 μM 4-PDS in 50 mM Bis-Tris/Tris acetate, pH 7.4, at 30° C. The reaction kinetics was followed by monitoring the formation of the reaction product of 4-PDS, 4-thiopyridone, at 324 nm. ● HbA, ○ HPPr-HbA, and ▲ αα-fumaryl-HbA, Δ αα-fumaryl-HPPr-HbA.

Correlation between the $O_2$-affinity of modified/mutant Hbs and the reactivity of their Cys-93(β) in the oxy conformation to form mixed disulfide with dithiodipyridine. Alterations in the $O_2$-affinity of Hb has been suggested to correlate with changes in the reactivity of Cys-93(β) (Imai et al., 1972; Kilmartin et al., 1975; Taketa et al., 1975; Imai et al., 1989; Bonaventura et al., 1998; Mawjood et al., 2000). In order to determine whether deoxy like conformational features of the modified Hbs are translated to the reactivity of Cys-93(β), thiol-disulfide exchange reaction of the modified Hbs has been studied. The number of titrable thiol groups of the derivatives is listed in Table 9. The kinetics of the reaction of Cys-93(β) of these Hbs in their carbonmonoxy form with 4-PDS is shown in FIG. 11. The rate of modification of Cys-93(β) of αα-fumaryl-HbA was considerably lower compared to that of HbA. On the other hand, the HPPr modification of HbA did not influence the reactivity Cys-93(β) significantly. However, the reactivity of Cys-93(β) of αα-fumaryl-HPPr-HbA was even lower than that of αα-fumaryl-HbA. Thus both the modifications together induced a synergistic influence on the reactivity of Cys-93(β).

TABLE 9

Number of titrable thiol groups of modified Hbs

| Hb | Titrable thiol groups |
| --- | --- |
| HbA | 2.1 |
| HPPr-HbA | 2.2 |
| αα-fumaryl-HbA | 2.2 |
| αα-fumaryl-HPPr-HbA | 1.9 |

Figure 12A:
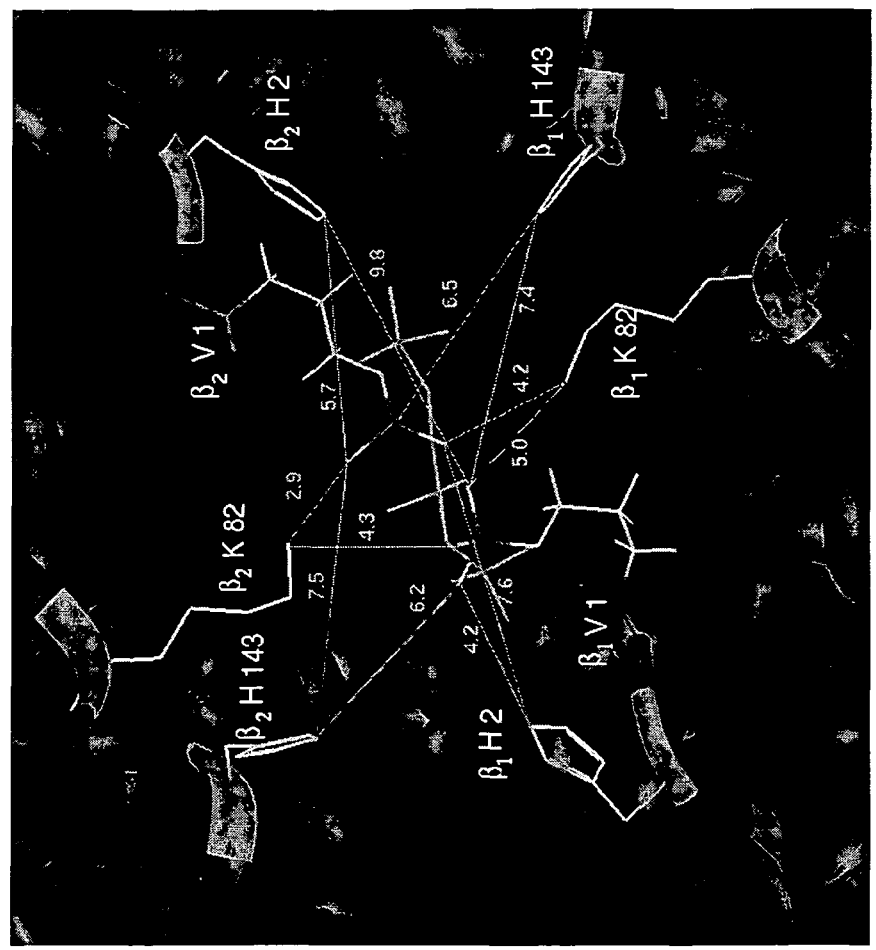
FIG. 12A-12B shows a molecular model of αα-fumaryl-HPPr-HbA. Panel A shows the location of the two covalent modifications in the central cavity viewed from the ββ-end of the central cavity. In the color version, the α-chains are shown in red, the β-chains in blue and heme in green. Val-1(β) side chains are shown in orange and the HPPr groups are in cyan with their phosphates in red. Lys-99(α) side chains are in magenta and the fumaryl group is in green. Panel B shows an exploded view of the DPG binding pocket of αα-fumaryl HPPr-HbA. In the color version, the α-chains are shown in red and the β-chains in blue. The positively charged centers of DPG pockets are shown in yellow with the side chains projecting out of the peptide back bone (ribbon), except that Val-1(β) is shown in purple for clarity. The carbon chain of HPPr moiety is in cyan and its phosphate is shown in red. DPG is shown in the background in magenta to provide a feeling for the location of the phosphates of the covalently linked HPPr moiety relative to the phosphates of DPG. Internuclear distances from the closest negative charge centers of the phosphates to the positively charged centers of the HPPr covalently bound onto Val-1(β) is provided.

Molecular Models of αα-fumaryl-HPPr-HbA. FIG. 12A depicts the molecular model of doubly modified Hb. In the figure, the central cavity of the doubly modified Hb is viewed from the ββ-end of the central cavity to provide a comprehension of the positioning of the two central cavity modifications engineered into Hb to generate very low oxygen affinity molecule. In the color version of the model the α-chains are shown in red ribbons, and the β-chains in blue ribbons. The hemes are depicted in green color. The αα-fumaryl crossbridge is shown in magenta and the HPPr groups within the ββ-cleft are shown in cyan with the phosphate groups in red. The molecular models of singly modified Hbs have also been generated (data not shown), and these models have established that the presence of one modification has very limited influence on the structural changes induced into Hb by the other.

Figure 12B:
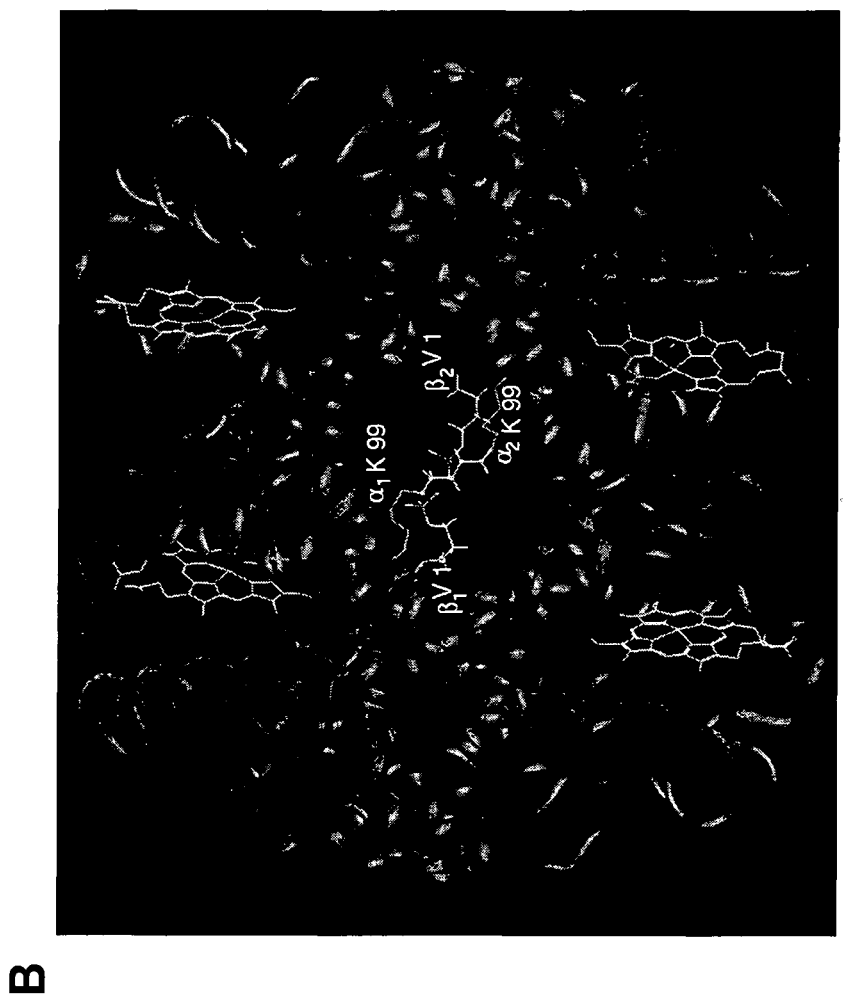

The exploded view of the ββ-cleft of doubly modified Hb is shown in FIG. 12B. The color version of the model has incorporated the DPG in background in magenta to depict the location of the phosphate groups of DPG within positive charge dense DPG binding pocket of the molecule. The carbon chain of HPPr moiety is shown in cyan with the phosphate group being depicted in red. Val-1(β) is shown in purple. The phosphate group of HPPr covalently linked to the amino group of Val-1(β) occupies a position within the ββ-cleft that is very close to the position occupied by phosphate of DPG that is bound at the ββ cleft. The location of the peptide backbone of six positively charged residues of the DPG binding pocket that interact with DPG [His-2(β), Lys-82(β) and His-143(β)] are identified in the ribbon diagram by green color and the side chains of these residues are also depicted. Internuclear distances between the negatively charged centers of phosphate and the positively charged centers of the protein in the DPG pocket of Hb that have been implicated to interact with the phosphate groups of DPG have been measured. The closest distances measured are shown in the figure (FIG. 12B) and also summarized in Table 10. It is interesting to note that the negatively charged centers of phosphate of HPPr moiety linked to Val-1(β) could interact not only with the positive charge centers of cis-dimers, but also with those of the trans dimers. Therefore, the HPPr moieties covalently linked to Val-1(β) may be expected to function as the pseudo crosslinks to stabilize the interdimeric interactions of the molecule. Thus, the doubly modified Hb is an intramolecular crosslinked Hb, with a covalent cross-link between the α-chains and a psuedo crosslink between the β-chains.

TABLE 10

Internuclear distances with in the ββ-cleft of αα-fumaryl-HPPr-HbA

| Residues of beta chain | Internuclear distance (Å) | |
| --- | --- | --- |
| | Phosphate 1 | Phosphate 2 |
| H2 | 4.2 (5.7) | 9.8 (7.6) |
| K82 | 5.0 (2.9) | 4.3 (4.2) |
| H143 | 7.4 (7.5) | 6.2 (6.5) |

Only the closest distance between the negatively charged centers of the phosphate and the positively charged groups of the DP binding pocket (ββ-cleft) are given. Internuclear distances for the opposite beta chain (trans-chain) are the ones given in parentheses.

Discussion

The modification of HbA with G3P generated a low oxygen affinity Hb (HPPr-HbA) that is insensitive to DPG and IHP. The modulation of the oxygen affinity of Hb by the covalently attached HPPr group is comparable to that of pyridoxal phosphate in $\alpha_2(\beta^{PLP})_2$ (Benesch et al., 1973) and to a higher level than that by carboxymethyl group (DiDonato et al., 1983) or galacturonic acid (Acharya, 1994) conjugated at Val-1(β). Thus, introduction of a phosphate group at this site seems to stabilize the low oxygen affinity conformation better than a carboxyl group. However, addition of a phosphate at Val-1(β) does not seem to be enough to exhibit such impact on the oxygen affinity of Hb. Affinity labeling of Val-1(β) with glucose-6-phosphate does not reduce the oxygen affinity of Hb (Haney and Bunn, 1976) to the extent that is seen with G3P or pyridoxal phosphate. The structural features of these added groups seem to make major contribution towards this effect. In $\alpha_2(\beta^{PLP})_2$ the two phosphates of the PLP groups take positions very close to the positions of the phosphates of DPG in deoxy Hb (Arnone et al., 1977). Thus, these phosphates can mimic the influence of DPG in stabilizing the deoxy state of Hb. G3P with similarities in structure with DPG, seems to exhibit similar impact on the oxygen affinity of Hb.

In order to understand the interactions of HPPr group with DPG binding site, molecular modeling studies of deoxy HPPr-HbA were carried out (FIG. 12). These studies indicated that the negative charges of the phosphate of the HPPr group can interact with the positive charge of Lys-82 of the cis as well as the trans β-chain of the modified Hbs (Table 10). In addition, interactions between His-2 of the cis β-chain and His-143 of the trans β-chain may also be possible. These interactions are comparable to the ones reported for pyridoxal phosphate-modified Hb (Haney and Bunn, 1976). Although, such interactions are likely to exist in carboxymethylated Hb and galacturonic acid modified Hb (Acharya et al., 1994), phosphate mediated interactions in HPPr-HbA and $\alpha_2(\beta^{PLP})_2$ seem to be more intense. These interactions that operate across the ββ-cleft stabilizing a deoxy-like state conformation are considered to serve as the 'pseudo crosslinks' within the DPG pocket (Arnone et al., 1977; Fronticelli et al., 1990).

HPPr-HbA reacts with DBBF under deoxy conditions in much the same way as the unmodified HbA in terms of the reactivity of Lys-99(α) to form cross-bridge. Thus, the electrostatic modification of Val-1(β) of ββ-cleft does not seem to perturb the orientation or reactivity of the e-amino groups of Lys-99(α) in the deoxy state. Besides, αα-fumaryl-HPPr-HbA exhibited an isoelectric point comparable to that of HPPr-HbA. The loss of positive charge resulting from the αα-fumaryl crosslinking is not apparent from the isoelectric focusing pattern. This behavior is consistent with the earlier observation that the isoelectric focusing pattern of αα-fumaryl-HbA under oxy conditions is nearly identical to the isoelectric focusing pattern of HbA (Chatterjee et al., 1986). This compensation in the charge of HbA has been suggested to be a result of an increased pKa of a neighboring residue, Glu-101($\alpha$). This phenomenon seems to be conserved in the doubly modified derivative, $\alpha\alpha$-fumaryl-HPPr-HbA. This behavior is distinct as compared to that seen on the generation of $\alpha\alpha$-fumaryl-Hb-P (Manjula et al., 2001). The electrostatic modifications in $\alpha\alpha$-fumaryl-Hb-P are both from the mid central cavity whereas $\alpha\alpha$-fumaryl-HPPr-HbA has one modification in the mid central cavity and the other in the $\beta\beta$-cleft. Combining the electrostatic modification of Val-1($\beta$) with $\alpha\alpha$-fumaryl crosslinking results in a partial additive influence in terms of reducing the $O_2$-affinity of HbA. From the mutant hemoglobin analysis, it has been hypothesized that the number of positive charges in the central cavity determines the $O_2$-affinity of the molecule (Perutz et al., 1994). It is suggested that the stability of the T-structure is inversely proportional to the overall positive charge in the central cavity. Accordingly, lowered $O_2$-affinity of $\alpha\alpha$-fumaryl-HPPr-HbA is consistent with the hypothesis that the reduction of the positive charge in the central cavity of Hb generates a more stable T-structure.

$\alpha\alpha$-fumaryl-HPPr-HbA lacks sensitivity towards the allosteric effectors, chloride, DPG and IHP. The molecular modeling studies of $\alpha\alpha$-fumaryl-HPPr-HbA indicated that the fumaryl crosslink can be introduced into the mid central cavity of HPPr-HbA with out altering the positions of the HPPr groups at Val-1($\beta$) (FIG. 12). Therefore, the electrostatic interactions between phosphates of the HPPr group and positive charges of DPG residues that are possible in HPPr-HbA can also operate in $\alpha\alpha$-fumaryl-HPPr-HbA. The presence of an $\alpha\alpha$-fumaryl crossbridge in the mid central cavity coupled with the 'pseudo crosslink' in the $\beta\beta$-cleft can therefore be expected to drastically reduce the plasticity of the molecule in these two domains of the central cavity. It may be noted that HbA carboxymethylated at all its four $\alpha$-amino groups is also insensitive to the presence of these effectors (DiDonato et al., 1983). Thus desensitization of Hb to the presence of chloride, DPG and IHP can be achieved by either electrostatic modification of the $\alpha\alpha$-end and the $\beta\beta$-cleft of the central cavity, or by combining the electrostatic modification of the $\beta\beta$-cleft with the $\alpha\alpha$-fumaryl crosslinking in the mid central cavity of HbA.

$\alpha\alpha$-fumaryl-HbA exhibited reduced sensitivity to L35 as compared to HbA. This is expected since L35 binds at the $\alpha\alpha$-end with its distal end projecting into the cavity closer to Lys-99 of $\alpha$-chain (Lalezari et al., 1990). Similarly, $\alpha\alpha$-fumaryl-HPPr-HbA also exhibited reduced sensitivity to L35. However, although the extent of modulation of the $O_2$-affinity of $\alpha\alpha$-fumaryl-HPPr-HbA by L35 was less than that of HbA, the $O_2$-affinity of this derivative in the presence of L35 was lower than that of HbA and was comparable to that of HPPr-HbA in the presence of the same effector. The electrostatic modification of the $\beta\beta$-cleft of $\alpha\alpha$-fumaryl-HbA compensates for the structural consequences of the presence of the cross-bridge in the mid-central cavity that reduces the modulation of the $O_2$-affinity of HbA by L35.

Geminate recombination of CO is highly responsive to the conformational properties of HbA (Lalezari et al., 1990; Friedman et al., 1985; Marden et al., 1987; Murray et al., 1988; Huang et al., 1999). The geminate binding of CO to photodissociated COHb occurs within a few hundred nanoseconds. Therefore, the geminate yield indicates the ligand binding affinity of the foremost structure of Hb in R to T transition. Apparently, this initial structure is expected to have the highest geminate yield since other structures in R to T transition attain lower ligand affinity conformation. The present geminate binding studies of modified Hbs indicated that HPPr modification reduces the ligand binding affinity of the initial population of photodissociated HbA more than $\alpha\alpha$-fumaryl-crosslinking. However, the P50 values of HPPr-HbA and $\alpha\alpha$-fumaryl-HbA were comparable. This may implicate that the subsequent structures in R to T transition of $\alpha\alpha$-fumaryl-HbA exhibit a larger variation in ligand binding affinity as compared to those of HPPr-HbA. In $\alpha\alpha$-fumaryl-HPPr-HbA, both modifications exerted combined influence on geminate binding as well as on overall $O_2$-affinity. The influence of IHP was less on geminate yield and more on P50 of $\alpha\alpha$-fumaryl-HbA as compared to that of HbA. Low ligand affinity structures of $\alpha\alpha$-fumaryl-HbA seem to respond more to IHP than the initial population. Similarly, the effect of L35 was less on geminate yield of HPPr-HbA and more on its P50 than of HbA, indicating the enhanced influence of L35 on intermediate structures of HPPr-HbA in R to T transition.

The frequency of $\nu$(Fe-His) indicates the conformation of Hb at the heme surroundings (Friedman, 1985; Friedman et al., 1985; Marden et al., 1987; Murray et al., 1988; Friedman, 1994; Huang et al., 1999; Friedman et al., 1983; Peterson and Friedman, 1998). This frequency is highest for a fully liganded R structure and lowest for an unliganded T structure. Modified hemoglobins with low $O_2$-affinity have been shown to have reduced $\nu$(Fe-His) frequency in the liganded state. Since the frequency of $\nu$(Fe-His) reflects the structure of liganded R state and geminate yield determines the structure of the initial population for recombination, the comparison of these two parameters of modified Hb may indicate the ease with which one molecule undergoes changes in the tertiary structure at the heme after photodissociation. $\alpha\alpha$-fumaryl-HbA and HPPr-HbA exhibited reduced frequency than HbA, indicating conformational changes at the heme. Interestingly, $\alpha\alpha$-crosslinking reduced the frequency more than HPPr modification, whereas the later modification reduced the geminate binding more than the former. This may be interpreted that HPPr modification did not alter the R state structure of HbA in the heme environment as much as $\alpha\alpha$-crosslinking. However, HPPr-HbA undergoes structural changes at the heme more rapidly than $\alpha\alpha$-fumaryl-HbA, upon photodissociation.

The change in the reactivity of Cys-93($\beta$) in oxy state can be considered as an indicator of a change at the $\alpha1\beta2$ interface in a given mutant or chemically modified Hb (Imai et al., 1972; Kilmartin et al., 1975; Taketa et al., 1975; Imai et al., 1989; Bonaventura et al., 1998; Mawjood et al., 2000). The electrostatic modification at the $\beta\beta$-cleft had no influence on the reactivity of Cys-93($\beta$), even though its $O_2$-affinity was lower than that of HbA. On the other hand, the $\alpha\alpha$-fumaryl crossbridge that lowers the $O_2$-affinity of HbA also lowered the reactivity of Cys-93($\beta$). The doubly modified Hb, $\alpha\alpha$-fumaryl-HPPr-HbA, exhibited a Cys-93($\beta$) reactivity even lower than that of $\alpha\alpha$-fumaryl-HbA, a synergistic influence of the two modifications.

The fumarate mediated cross-linking of Lys-99($\alpha$) of hemoglobin reduces the $O_2$-affinity of the tetramer without apparent alterations in its deoxy conformation (Chatterjee et al., 1986). The reduction in $O_2$-affinity is primarily due to the reduction in KR (Vandegriff et al., 1989). Accordingly, the R-structure of $\alpha\alpha$-fumaryl-HbA has been predicted to be different as compared to that of HbA. The environment of Cys-93($\beta$) of $\alpha\alpha$-fumaryl-HbA appears to be perturbed from the one in the R-structure of HbA, reducing the reactivity of its thiol group. The reduced reactivity of Cys-93($\beta$) on deoxygenation of HbA has been attributed to the conformational changes as well as to the salt bridge formed between His-146($\beta$) and Asp-94($\beta$) (Kilmartin et al., 1975). Des-His-146($\beta$)

HbA exhibited an increased reactivity of Cys-93(β) in oxy conformation, indicating that His-146(β) influences the reactivity of Cys-93(β) even in oxy structure. The FT-IR studies of oxy and met hemoglobins suggested a correlation between the reactivity of Cys-93(β) and the probability of this residue being external to the $F_7H$ pocket (Moh et al., 1987). An interaction between Cys-93(β) and Tyr-145(β) that can influence the reactivity of Cys-93(β) has also been suggested. The αα-fumaryl cross-linking of HbA has altered one or more of these interactions resulting in a reduction in the reactivity of Cys-93(β) in the oxy conformation.

The results of the present study along with the earlier results of αα-fumaryl-Hb-P, and the tetra carboxymethylated Hb demonstrated that electrostatic modification of the ββ-end, αα-end and mid central cavity that lower the $O_2$-affinity can be combined in pairs to generate species of Hb that exhibit $O_2$-affinity lower than that with either of the modifications. An interesting aspect of the two very low $O_2$-affinity forms of Hb generated by combining the two chemical perturbations of central cavity of Hb, namely αα-fumaryl-Hb-P and αα-fumaryl-HPPr-Hb is that the $O_2$-affinity of both species are insensitive to the presence of allosteric effectors. Presumably, these represent the conformational state of Hb wherein the protein has accessed the very low affinity T-state. In contrast, PEGylation of Hb particularly hexaPEGylation of Hb with PEG-5000 induces a degree of rigidity to the oxy conformational state of Hb which is apparently a high $O_2$-affinity R-state, again non responsive to allosteric effectors. If the very low $O_2$-affinity Hbs are subjected to hexaPEGylation protocol that we have used to generate the current versions of non-hypertensive Hbs, it is conceivable that PEGylated Hbs with very low oxygen affinity are generated.

HexaPEGylation of αα-fumaryl cross-linked Hb generated a product that has an $O_2$-affinity comparable to that of unmodified Hb (Example 1). The presence of αα-fumaryl cross-link in the PEGylated-Hb has compensated partially the high oxygen affinity inducing propensity of PEGylation reaction. The oxygen affinity of the PEGylated αα-fumaryl Hb is intermediate to that of PEGylated Hb and αα-fumaryl Hb. The G3P modification in HPPr-αα-fumaryl-HbA is expected to further neutralize the influence of PEGylation to generate a PEGylated Hb with an oxygen affinity intermediate to that of PEGylated αα-fumaryl Hb and HPPr-αα-fumaryl-HbA. Availability of a series of PEGylated Hbs with varying oxygen affinities can facilitate the production of non-hypertensive PEGylated Hbs as blood substitutes for customized clinical applications.

Example 3

Reversible Modification of Cys-93(β) of Hemoglobin During Extension Arm Facilitation-Mediated Maleimide Chemistry-Based PEGylation The treatment of blood losses requires achieving two important functions; (i) plasma expansion and (ii) restitution of oxygen carrying capacity. Therefore the development of an optimal fluid for resuscitation from blood losses requires an integrative process that includes volume expansion and oxygen transport. This concept of treating blood loss using a transfusion fluid other than donor blood, blood substitute, is very distinct from the earlier strategies of designing blood substitutes. The development of polyethylene glycol (PEG) conjugated proteins (hexaPEGylated Hb and hexaPEGylated PEG-albumin) and their use in animal experimental models has demonstrated that these materials posses near ideal plasma expansion properties. They provide prolonged volume recovery via lasting intravascular retention, and in addition they have the unique property of restoring/preserving microvascular function, particularly venular blood flow and functional capillary density as shown with the development of PEG-albumin. PEGylation of hemoglobin (PEG-Hb) should in principle yield the second component required in the treatment of blood losses, namely oxygen transport capacity.

For PEG-Hb strategy to succeed as a oxygen carrying plasma volume expander, this material must fulfill two critical conditions, namely: 1) It must be void of the vasoactivity usually encountered when molecular hemoglobin (Hb) is introduced into the circulation; and, 2) It must deliver oxygen in a physiologically useful process.

The neutralization of the vasoactivity of acellular Hb on PEGylation has been shown when used in top loads, hemodilution, and hemorrhagic shock resuscitation. The neutralization of vasoactivity has been demonstrated in in vivo experiments at the level of the microcirculation, in systemic studies in small and large animals, and in clinical trials. A new emerging concept is that in fact the PEGylated proteins present vasodilatory properties. This effect removes one of the major obstacles in the use of molecular Hb as an oxygen carrier for blood substitutes.

However, the remaining area of development of oxygen carrying plasma volume expander is the optimization of the oxygen transport characteristics of PEG-Hb and the colligative properties induced to Hb as a consequence of PEGylation. The PEGylation of Hb results in generation of species with very high affinity for oxygen and increase the colloidal osmotic pressure (COP) and also viscosity. The oxygen affinity of the current versions of PEGylated Hb is inadequate for insuring safety in resuscitation and if reproduced in patients would invariably cause the transfusion of blood much before this Hb level is reached.

In summary, regarding oxygen delivery presently available PEG-Hbs are not suitable for delivering oxygen in clinical settings because blood transfusions will be used much before the patient oxygenation is lowered to the level at which PEG-Hb releases therapeutically adequate quantities of oxygen. Secondly, due to the high COP of PEG-Hb the concentration of PEG-Hb in blood is limited by autotransfusion since the oncotic effect rapidly dilutes the protein. This effect further limits the ability of PEG-Hb solutions to carry and deliver oxygen, since the effective total increase of oxygen carrying capacity achievable with present formulations is a maximum of 2 g/dl of Hb. Lowering the oxygen affinity of PEGylated Hb and/or increasing the concentration of the PEG-Hb that can be transfused into the system are the possible approaches to ensure adequate supply of oxygen to tissue when PEGylated Hb is used as oxygen carrying plasma volume expanders. The optimal p50 of a oxygen carrying plasma volume expander appears to be about 15 mmHg, as compared to the p50 of blood in most mammalian species ~28 mmHg. Design of PEGylated Hb with this level of oxygen affinity is addressed here.

To simplify the PEGylation of Hb (or proteins) with multiple copies of PEG-chain a new PEGylation protocol was developed. This protocol involves the thiolation-mediated maleimide chemistry based PEGylation of HbA. In this new platform, the surface ε-$NH_2$ groups of HbA are activated as maleimide reactive thiols using 2-iminothiolane. The reactive intrinsic thiols of Hb [Cys-93(β)] and the newly generated extrinsic thiol groups are then modified by the desired PEG-maleimide. The two steps of the reaction, i.e., thiolation of Hb and PEG-modification of the thiolated Hb can be carried out either by incubating the Hb simultaneously with the two reagents as a one step process or as a two step process, the thiolation is done first and PEGylation afterwards. The relative merits and disadvantages have been discussed in Acharya and Manjula (2006) and Manjula et al. (2005). The resulting PEGylated Hb exhibits a hydrodynamic volume that is significantly higher than the value based on its molecular mass of Hb and the number of PEG-5K chains attached to it. The PEGylation reaction is versatile in that a desired level of size enhancement of Hb can be achieved by optimizing the number of amino groups activated by iminothiolane and selecting the appropriate molecular size of the PEG-reagent.

The extension arms introduced onto the Hb are δ-mercapto butyrimidyl chains on the ε-amino groups; the chemical linkage between the extension arm and the Lys side chain of Hb is an amidine linkage, which is positively charged at physiological pH values just as the ε-amino groups of the protein. Accordingly this is a conservative PEGylation platform; i.e., the PEGylation does not change the net charge on the surface of Hb. This PEGylation reaction has been optimized to generate multiple size-enhanced PEGylated Hbs with high oxygen-affinity. One of the products, [(SP-PEG5K)$_6$-HbA] that carries, on an average, six copies of PEG-5000 chains per Hb tetramer, is vasoinactive when analyzed in top load (10%) as well as in exchange transfusion (50%) hamster models. (SP-PEG5K)$_6$-HbA is homogeneous in terms of net charge and hydrodynamic volume. Its hydrodynamic volume corresponds to that of a globular protein of a molecular mass of ~256,000, even though the actual mass is only ~94,000 Da. It is concluded that one or more of the multiple new molecular properties of (SP-PEG5K)$_6$-Hb, namely, enhanced molecular volume, viscosity, colloidal oncotic pressure and/or the high oxygen affinity, has endowed the molecule with the propensity to neutralize its vasoactivity. Thus surface decoration of Hb with PEG-5K using the new PEGylation platform generates a non-hypertensive Hb when conjugated with six copies of PEG-5K chains, whereas the earlier PEGylation product (Enzon) PEGylated bovine Hb carries ten copies of PEG-5K chains conjugated to it by non-conservative chemistry. Thus the conservative protocol developed here is more efficient in inducing the non-hypertensive properties to Hb on PEGylation. The simplicity and the high efficiency of this new PEGylation protocol makes the production of (SP-PEG5K)$_6$-HbA a cost-efficient process (Acharya et. al. 2005, Manjula et al. 2005).

Molecular basis of the O$_2$ affinity of hexaPEGylated Hbs. HexaPEGylated Hbs were generated by four approaches: (1) thiolation mediated maleimide chemistry based PEGylation, (2) acylation chemistry, (3) reductive alkylation chemistry and (4) thiocarbamoylation chemistry. Surprisingly, the oxygen affinity of all hexaPEGylated molecules, (SP-PEG5K)$_6$-Hb, (Propyl-PEG5K)$_6$-Hb, (Propionyl-PEG5K)$_6$-Hb, (PTC-PEG5K)$_6$-Hb and (CAM-PEG5K)$_6$-Hb was very high and was comparable to one another. This unanticipated result has made it almost impossible to generate PEG-Hb conjugates with lower oxygen affinity than the current material generated by thiolation mediated maleimide chemistry based PEGylation. Accordingly, new strategies have to be developed to generate lower oxygen affinity PEGylated Hbs which could be considered as second generation PEGylated Hbs.

In (SP-PEG5K)$_6$-Hb and (CAM-PEG5K)$_6$-Hb, (CAM=carboxamido methyl) the —SH groups of Cys-93(β) has been PEGylated, and accordingly it could be speculated that the high oxygen affinity of these two hexaPEGylated products is a consequence of PEGylation of Cys-93(β). The development of the reductive alkylation platform, the acylation chemistry platform and the phenyl isothiocyanato chemistry platform has been to address this issue, namely avoid PEGylating Cys-93(β) during the PEGylation reaction. If the increase in the O$_2$ affinity is a consequence of PEGylation of Cys-93(β), the O$_2$ affinity of the hexaPEGylated Hb generated by these alternate chemical approaches would be expected to be comparable to that of unmodified Hb. As reflected by the O$_2$ affinity of (Propyl-PEG5K)$_6$-Hb, (Propionyl-PEG5K)$_6$-Hb, and (PTC-PEG5K)$_6$-Hb (PTC=Phenyl thiocarbamoyl) all of which have the Cys-93(β) free (i.e. unmodified), it is clear that the O$_2$ affinity increase is not a direct consequence of Cys-93(β) modification. Accordingly it is concluded that the increased O$_2$ affinity of PEGylated Hb is a general consequence of the surface decoration of Hb with PEG-chains, and that site selectivity PEGylation and the chemistry of the linkage between the PEG-chains and the side chains of Hb has limited influence on the O$_2$ affinity of the final product.

Influence of PEGylation of r-Hb[Cys-93(β)→Ala] using thiolation mediated maleimide chemistry based PEGylation platform on its O$_2$ affinity. The development of hexaPEGylated Hb, (SP-PEG5K)$_6$-Hb, using thiolation-mediated maleimide chemistry-based PEGylation has validated the concept that engineering 'plasma volume expander'-like properties to Hb neutralizes its vasoactivity. The high O$_2$ affinity of hexaPEGylated Hb has been attributed to the two PEG5K chains on its two Cys-93(β) residues. In an attempt to map the influence of the additional four PEG-5K chains of HexaPEGylated Hb on the O$_2$ affinity, the influence of PEGylation of the surface amino groups alone on the subunit interface interactions and O$_2$ affinity of Hb using r-Hb(βC93A) was investigated. The molecular radius of PEGylated r-Hb(βC93A) was only slightly smaller than that of (SP-PEG5K)$_6$-Hb, and the overall site-selectivity of PEGylation in the PEGylated r-Hb (βC93A) at Lys-residues was comparable to that of (SP-PEG5K)$_6$-Hb. Proton NMR studies have shown that the conjugation of the protein with PEG-5K does not have any significant influence on its subunit interface interactions. Surprisingly, the influence of PEGylation on the O$_2$ affinity and Bohr Effect of HbA and the mutant Hb is also nearly the same. Apparently, conjugation of PEG-chains to Lys residues of Hb by the thiolation mediated PEGylation induces unique changes in the structure of the hydration shell of Hb (layer of tightly bound water molecules), which, in turn, induces constraints in its R to T conformational transition to favor the more hydrated R-state (Li et al., 2006).

Strategies to design Low Oxygen Affinity PEGylated Hbs. Though high O$_2$-affinity of the PEGylated Fibs is considered as an advantageous factor in achieving the neutralization of the vasoactivity of Hb by reducing the amount of oxygen delivered on the arterial side of the microcirculatory system (Vandegriff et al., 2003; Winslow et al., 1998; Tsai et al., 2003; Tsai et al., 2004), the O$_2$-affinity of the present versions of PEGylated Hbs appears to be too high to deliver adequate levels of oxygen to tissues. Accordingly, the use of low O$_2$-affinity Hbs instead of using normal adult human Hb as substrates has been considered for the generation of PEGylated Hbs using the same protocols discussed above (Acharya et al., 2005; Manjula et al., 2005; Hu et al., 2005; U.S. Pat. No. 7,144,989 B2).

Recent studies of hexaPEGylation of αα-fumaryl Hb has generated a PEGylated Hb (Example 1) with an oxygen affinity (P50~14 mm of Hg) lower than that of hexaPEGylated Hb (P50~7 mm of Hg). HexaPEGylation of modified Hbs, with an oxygen affinity still lower than that of αα-fumaryl Hb, may be expected to facilitate the generation of very low oxygen affinity that is comparable to that of erythrocytes (P50~28 mm of Hg) (Example 2). Preparation of doubly modified Hbs is an approach to generate very low oxygen affinity Hbs that could be used as substrates for PEGylation to generate low oxygen affinity PEGylated Hbs.

The Prototype of PEGylated Hb for Engineering the Desired Oxygen Affinity for developing Second Generation PEGylated Hbs. HexaPEGylated Hb prepared by the extension arm facilitated maleimide chemistry based PEGylation is nonhypertensive, and is currently in clinical trials. In trying to establish whether six copies of PEG-K per tetramer is the minimum number of PEG chains needed to generate a nonhypertensive Hb molecule, it has been shown that Hb with two and four copies of PEG-chains are also nonhypertensive when tested in an extreme hemodilution model in hamsters.

Hb with six copies of PEG-5K chains, P5K6 prototype molecules, as the general PEG-Hb conjugate platform has been used extensively to correlate the vasoactivity of PEGylated Hb as a function of chemistry of PEGylation induced molecular, structural and functional properties of PEGylated Hbs. The extension arm facilitated maleimide chemistry-based PEGylation platform generated nonhypertensive molecules with six copies of PEG-5K. The $O_2$ affinity of (SP-PEG-5K)$_6$-Hb is high (P50 around of 8 mm Hg). In searching for alternate protocols for PEGylation that can produce hexaPEGylated Hbs with lower $O_2$ affinity as compared to (SP-PEG-5K)$_6$-Hb, it has become apparent that the influence of hexaPEGylation on the oxygen affinity of Hb is essentially independent of the chemistry of PEGylation. On the other hand, the PEGylation-induced colligative properties of Hb (viscosity and COP) appear to be dependent on the chemistry of PEGylation. Inter-dimeric (intra tetrameric) interactions are minimally perturbed in hexaPEGylated Hbs generated by the extension arm facilitated maleimide chemistry based PEGylation; the dissociation constant for the dimerization of the tetraPEGylated Hb is not very different from the unPEGylated Hb. Clinical trails with hexaPEGylated Hb produced using extension arm facilitated PEGylation has not shown any toxicity to be concerned about, and accordingly when the low oxygen affinity Hb selected for PEGylation does not carry an intramolecular crosslinking the extension arm facilitated maleimide chemistry based PEGylation is probably the only choice for PEGylation protocol for PEGylation of Hb for engineering the lower oxygen affinity.

If introducing an intramolecular crosslinking is the necessary step in lowering the oxygen affinity of Hb to the desired before selecting for PEGylation, one could use any one of three PEGylation platforms that has been developed: (1) extension arm facilitated maleimide chemistry based PEGylation, (2) reductive alkylation chemistry base PEGylation, and (3) thiocarbamoylation-mediated PEGylation. In selecting the reductive alkylation chemistry-based PEGylation and thiocarbamoylation-mediated PEGylation, a higher level of increase in viscosity and COP is endowed to the PEGylated Hb on the basis of the amount of PEG used for surface decoration.

Selection of Prototypes of PEGylated Hbs that could be used for engineering the lower oxygen affinity. So far three prototypes of PEGylated Hbs generated using maleimide-PEG has been found to be non-hypertensive. The first prototype is a diPEGylated Hb wherein the maleimide PEG is used to PEGylate Cys-93(β) of Hb. This PEGylated Hb molecule exhibits a functional capillary density better than unmodified Hb, but not as good as the hexaPEGylated Hb in 10% top load experiments in hamster. In extreme hemodilution studies in hamster, however, these exhibit acceptable level of functional capillary density to achieve a good level of tissue oxygenation, in fact even better than the hexaPEGylated Hb.

The second prototype molecule is the tetraPEGylated Hb, the one that has been studied in good detail is the tetraPEGylated canine Hb. These prototype molecules are nonhypertensive in both 10% top load experiments and also in extreme hemodilution models. In this tetraPEGylated Hb, the PEGylation is on Cys-112(α) and Cys-93(β). Besides the tetraPEGylated canine Hb, four other recombinant Hbs PEGylated with PEG-maleimide have also been studied in extreme hemodilution models. All these tetraPEGylated Hbs function well in the extreme hemodilution model suggesting that four copies of Hb could be more than adequate for neutralizing the vasoconstrictive activity of Hb. Given the fact that four species of tetraPEGylated Hbs have been investigated so far, and the site selectivity of PEGylation is distinct in each of these tetraPEGylated Hbs, one could conclude that the site selectivity of the PEGylation may not very critical in the neutralization of the pressor effect of acellular Hb. This makes the case for developing r-Hbs with additional Cys residues as potential sites for PEGylation and generating tetraPEGylated Hbs.

The third prototype molecule is the hexaPEGylated Hb. This is the only prototype molecule that is generated by the extension arm facilitated, maleimide chemistry based PEGylation. In this, two of the PEG-chains are on Cys-93(β) and the rest are on the ε-amino groups of surface Lys residues. This is the most extensively studies molecule, particularly in large animals and is under the phase three clinical trial.

New PEGylation Protocol for generation of TetraPEGylated Hb by Extension Arm Facilitated maleimide Chemistry Based PEGylation. A protocol has been developed for tetraPEGylation of human Hb. The following scheme outlines that protocol:

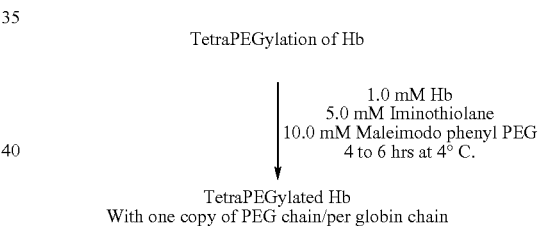

Incubation of Hb at a protein concentration of 1.0 mM, with 5 mM iminothiolane and 10 mM maleimido phenyl PEG for 4 to 6 hrs at 4° C. generates the tetraPEGylated Hb. Preliminary studies with a preparation of PEGylated Hb that carries around 4 to 5 PEG chains (when the PEGylation is carried out using a protein concentration of 1 mM, 10 mM iminothiolane and 10 mM maleimidophenyl PEG-5K) appears to be non-hypertensive in the extreme hemodilution hamster model and appears to be comparable to the hexaPEGylated Hb generated by the extension arm facilitated maleimide chemistry based PEGylation. Accordingly in view of the fact that all tetraPEGylated Hbs have been shown to be nonhypertensive (i.e. exhibiting a good functional capillary density) we expect this tetraPEGylated Hb to also exhibit good functional capillary density.

The tetraPEGylated Hb generated by this new PEGylation protocol (PEGylation carried out at a protein concentration of 1 mM) achieves the PEGylation of Hb at twice the concentration of Hb as compared to the protocol for the protein concentration used for the preparation of hexaPEGylated Hb. Further, the amount of maleimide used is only ten times that of Hb, whereas in the protocol for the generation of hexaPEGylated Hb, the maleimide PEG is used at a 20 fold molar excess. Thus, in generating the tetraPEGylated Hb, maleimide PEG used is nearly 50% lower as compared to that needed to generate hexaPEGylated Hb. Additionally, since the PEGylation is carried out at a higher concentration of Hb and a lower concentration of iminothiolane, a higher site selectivity is expected in the PEGylation. Of the four PEG-chains conjugated to Hb two are on the Cys-93($\beta$) and the other two are on the $\epsilon$-amino groups of surface Lys-residues.

Influence of PEGylation of low $O_2$ affinity Hbs using the thiolation mediated maleimide chemistry based PEGylation platform on their $O_2$ affinity. The high $O_2$ affinity of hexaPEGylated Hbs generated by various PEGylation platform demonstrates the influence of the PEG-shell on Hb generated on conjugation of multiple copies of PEG-chains on the $O_2$ dependent R-T conformational transition, establishing that the PEG-shell destabilizes the T-conformational state of Hb. This interpretation suggests that PEGylation of Hbs such as the r-Hbs or chemically modified Hbs with lower $O_2$ affinity (R→T conformational transition favored to T-state) as a possible approach to generate PEGylated Hbs with a lower $O_2$ affinity compared to the current versions of PEG-Hb conjugates. Two low $O_2$-affinity Hbs, namely Hb-Presbyterian and tetracarboxymethylated Hb (the carboxymethylation predominantly on the four amino terminal Val-residues), have been chosen to test this approach for generating low $O_2$ affinity PEGylated Hbs.

HexaPEGylation of Hb-Presbyterian as well as tetracarboxymethylated Hb using the thiolation mediated maleimide chemistry based PEGylation platform resulted in the generation of only high $O_2$ affinity PEG-Hb conjugates. Apparently, the PEG-shell induced R-state conformation favoring influence of hexaPEGylation is so strong that it neutralizes the low $O_2$ affinity inducing potential of the Presbyterian mutation as well as that of tetracarboxymethylation of the amino terminal Val-residues of Hb. Mixed disulfide forms of these, [Cys-93 ($\beta$) protected] have also been PEGylated using the same protocol, to establish whether the high $O_2$-affinity is a consequence of modification of Cys-93($\beta$). After the PEGylation, the mixed disulfides were reduced to regenerate the thiols on Cys-93($\beta$). Again the results are the same, generation of high $O_2$ affinity PEGylated fibs.

Influence of PEGylation of low oxygen affinity $\alpha\alpha$-fumaryl Hb (using the thiolation mediated maleimide chemistry based PEGylation platform) on its oxygen affinity: To overcome the influence of PEGylation on destabilizing the T-state of Hb and facilitating the generation of low oxygen affinity PEGylated Hbs, the low $O_2$ affinity intra-molecularly cross-linked Hb, $\alpha\alpha$-fumaryl Hb, has been subjected to hexaPEGylation using the same thiolation mediated maleimide chemistry-based PEGylation. Again as with the other two low oxygen affinity Hbs, the PEGylated product ended up as the high $O_2$ affinity material in spite of the fact this cross-linked Hb exhibited a lower $O_2$ affinity than Hb. As reported in Example 1, $\alpha\alpha$-fumary Hb PEGylated by using reductive alkylation chemistry-based PEGylation generated a hexaPEGylated Hb that exhibits an oxygen affinity comparable to that of unmodified Hb. In this hexaPEGylated $\alpha\alpha$-fumaryl Hb, thiols of Cys-93($\beta$) are not PEGylated, suggesting the need to keep the thiols of Cys-93($\beta$) free in the PEGylated Hb to keep the oxygen affinity oxygen affinity Hb lower (relative to that of PEGylated Hb) by PEGylating low oxygen affinity Hbs.

Influence of Reversible Blocking of Thiols of Cys-93($\beta$) of HbA during thiolation mediated maleimide chemistry based PEGylation. The significant difference in the oxygen affinity of hexaPEGylated $\alpha\alpha$-fumaryl Hb generated by thiolation-mediated PEGylation and reductive alkylation chemistry-based PEGylation has prompted the reversible protection of the thiols of Cys-93($\beta$) during thiolation mediated PEGylation and regeneration of the thiols of Cys-93($\beta$) after the completion of the PEGylation reaction. For this the thiols of Cys-93($\beta$) are protected as mixed disulfide with thiopyridine. HbA was first reacted with dithiopyridine, the resultant mixed disulfide of Hb with thiopyridine was isolated and subjected to thiolation mediated, maleimide chemistry-based PEGylation. After the completion of the PEGylation reaction, and excess of the maleimide PEG reagents were removed from the PEGylated bis Cys-93($\beta$) thiopyridyl Hb, the sulfhydryl groups of Cys-93($\beta$) were regenerated using a ten fold molar excess of Tris(2-carboxyethyl)phosphine (TCEP). After the release of the thiopyridine from the protein, the PEGylated protein was isolated by dialysis.

The oxygen affinity of the PEGylated Hb generated using thiopyridyl Hb (blocking the thiols of Cys-93($\beta$) as a mixed disulfide of thiopyridine) is shown in Table 11. The PEGylation of thiopyridyl Hb by the extension arm facilitated PEGylation has been carried out at two protein concentrations, 1.0 mM and 0.5 mM. Irrespective of whether the thiols of Cys-93($\beta$) has been modified as a mixed disulfide with thiopyridine, the PEGylated Hb exhibited high oxygen affinity as compared to the unmodified Hb. It may be noted that PEGylation has been carried out at two protein concentrations, namely at 1 mM and 0.5 mM. When the Hb concentration is 0.5 mm and 5 mM iminothiolane is used in the presence of 10 M Mal Phe PEG-5K, a hexaPEGylated Hb is formed as described previously. If the Hb concentration is increased to 1.0 mM without changing the concentration of iminothiolane and maleimido phenyl PEG, the PEGylation proceeds to a stage of only tetraPEGylation. The four PEG chains appear to be uniformly distributed on the four globin chains of the tetramer. On the other hand, if the Hb concentration is lowered to 0.25 mM, keeping the concentration of iminothiolane and of maleimidophenyl PEG-5K the same (5 mM and 10 mM) respectively, an octaPEGylated Hb is generated.

TABLE 11

Functional properties of (SP-PEG5K)-Hb

| Sample | $P_{50}$, mmHg (n) |
|---|---|
| HbA | 13.89 (2.89) |
|  | 14.44 (2.96) |
| PEGylated PDS-Hb | 6.76 (2.13) |
| (TP-Hb:IT:MalPhePEG::1:5:10) | 6.74 (2.10) |
| PEGylated-PDS-Hb(0.5:5:10) | 6.16 (2.00) |
| (TP-Hb:IT:MalPhePEG::O.5:5:10) | 6.03 (2.04) |
| PEGylated Hb-Hb | 6.51 (1.78) |
| (Hb:IT:Mal-Phe-PEG: 1:0.5:10) | 6.57 (1.80) |
| PEGylated-Hb | 6.53 (1.67) |
| (Hb:IT:MalPhePEG::0.5:5:10) | 6.55 (1.67) |

HbA concentration is about 0.025 mM in PBS.

It may be noted from Table 11 that the oxygen affinity of all samples are same even when the thiol groups of Cys-93($\beta$) of Hb is blocked as a mixed disulfide with thiopyridine. Thus the increase in the oxygen affinity of Hb is the same whether the thiol groups of Cys-93($\beta$) are PEGylated with maleimide PEG or as mixed disulfide with thiopyridine.

When the thiol group of Cys-93($\beta$) is reversibly blocked as mixed disulfide with thiopyridyl, the PEGylation of Cys-93 ($\beta$) can not take place. Thus PEGylation of thiopyridyl Hb at protein concentration of 1.0, 0.5 and 0.25 mM and maintaining the IT and the PEG-maleimide concentration at all three levels of protein concentrations at 5 mM and 10 mM respectively, will be expected to generate diPEGylated TP-Hb, tetraPEGylated-TP-Hb and hexaPEGylated TP-Hb respectively, wherein the thiols of Cys-93(β) are protected as mixed disulfide of thiopyridine.

The release of thiopyridine from these PEGylated samples can be achieved in principle using any thiol reagents like GSH, β-mercaptoethanol, and/or dithiothreotol, the PEGylated thiopyridyl Hb will undergo disulfide exchange reaction leading to the generation of free thiol groups on Cys-93(β). However these reactions, besides regenerating the thiols of Cys-93(β) also resulted in the formation of varying amounts of metHb. On the other hand, incubation of the PEGylated TP Hb in the presence TCEP has resulted in the regeneration of the thiol group of Cys-93(β) without the formation of met Hb.

The influence of regenerating the thiols group on Cys-93 (β) of PEGylated TP-Hb is shown in Table 12. It may be seen from the table that thiopyridylation of Hb increases the oxygen affinity of Hb slightly, and on releasing the thiopyridyl moieties from the protein, the influence on the oxygen affinity is also reversed. On the other hand the oxygen affinity of HbA is not influenced on incubation with TCEP. But the oxygen affinity of diPEGylated-TP-Hb is lower only very slightly on incubation with TCEP to generate diPEGylated-Hb. It should be noted that this diPEGylated Hb is not the same of the earlier diPEGylated Hb that was generated by incubating Hb with maleimido phenyl PEG-5K that results in the PEGylation of both Cys-93(β) residues of Hb. The diPEGylated Hb that is generated in this process has both of the Cys-93(β) residues free, and accordingly the higher oxygen affinity of this material is a direct consequence of the PEGylation of Hb at the ε-amino groups of Lys residues though the engineering of the extension arm, (δ-mercaptobutirimidyl-chains) on these residues. Similarly, the tetraPEGylated Hb generated by this modified version of the extension arm facilitated maleimide chemistry-based PEGylation has its Cys-93(β) underivatized and the PEGylation is on the ε-amino groups of surface Lys side chains through the extension arms. The oxygen affinity of this tetraPEGylated Hb is slightly higher than that of the diiPEGylated Hb, i.e., when the Cys-93(β) is not masked or PEGylated, the differences in the influence of PEGylation from going to di to tetraPEGylation can be noticed.

TABLE 12

Oxygen Affinity of PEGylated Hbs after the Regenration of Thiols of Cys-93(β)

| Sample | $P_{50}$, mmHg (n) |
|---|---|
| HbA | 14.62 (2.86) |
|  | 14.10 (2.98) |
| Bis TP-HbA | 10.16 (2.65) |
|  | 10.16 (2.65) |
| HbA + TCEP | 14.22 (3.00) |
|  | 14.48 (3.03) |
| Bis-TP-HbA + TCEP | 14.66 (2.90) |
|  | 14.60 (2.92) |
| DiPEGylated-TP-Hb + TCEP | 9.03 (1.93) |
|  | 8.79 (1.92) |
| TetraPEGylated-TP-Hb(0.5:5:10) + TCEP | 7.31 (1.84) |
|  | 7.40 (1.85) |

HbA concentration is about 0.025 mM in PBS. For regeneration of thiols of Cys-93(β) the PEGylated samples were incubated with 10 mM TCEP.

Influence of Reversible Blocking of the Thiols of Cys-93 (β) of αα-fumaryl Hb during Thiolation Mediated PEGylation. Interestingly, with αα-fumaryl Hb, when the Cys-93(β) is reversibly protected during PEGylation as a mixed disulfide with thiopyridine (regenerated at the end of PEGylation using TCEP) the resulting hexaPEGylated-αα-fumaryl Hb exhibited an $O_2$ affinity comparable to that of unmodified Hb, P50 around 16.5 mmHg (Table 13).

TABLE 13

Reversible protection of thiols of Cys-93(β) during thiolation mediated maleimide chemistry-based PEGylation: Functional Properties of PEGylated αα fumaryl-Hb

| Sample | $P_{50}$, mmHg (n) |
|---|---|
| HbA | 15.04 (3.05) |
|  | 15.01 (3.00) |
| αα-fumaryl HbA | 30.91 (2.16) |
|  | 30.73 (2.16) |
| Bis-Cys-93(β,β')-thiopyridyl-αα-fumaryl Hb | 21.14 (2.15) |
|  | 20.01 (2.09) |
| Bis-Cys-93(β,β') thiopyridyl PEGylated αα-fumaryl-Hb (1.0:5:10) | 13.90 (1.79) |
|  | 13.68 (1.80) |
| Bis-Cys-93(β,β')-thiopyridyl, PEGylated ααfumary-Hb (0.5:5:10) | 11.67 (1.77) |
|  | 11.70 (1.77) |
| PEGylated-αα-fumarylHb (1.0:5:10) | 10.74 (1.74) |
|  | 10.78 (1.75) |
| PEGylated αα-fumaryl-Hb (0.5:5:10) | 9.80 (1.66) |
|  | 9.97 (1.69) |
| Bis-Cys-93(β,β') thiopyridyl PEGylated αα-fumaryl-Hb (1.0:5:10) + TCEP (10 mM final) | 16.16 (1.68) |
|  | 16.60 (1.68) |
| Bis-Cys-93(β,β') thiopyridyl PEGylated αα-fumaryl-Hb (0.5:5:10) + TCEP (10 mM final) | 13.89 (1.64) |
|  | 13.73 (1.67) |

HbA concentration is about 0.025 mM in PBS.

Accordingly, for generating the lower oxygen affinity PEGylated Hbs using extension arm facilitated maleimide chemistry based PEGylation, the thiol groups of lower oxygen affinity Hbs are reversibly protected as mixed disulfides of thiopyridine during the PEGylation reaction. After PEGylation, the mixed disulfide linkage on the thiols of Cys-93(β) are released by treatment with TCEP (see scheme below). Thus the protocol for tetraPEGylated Hb, will result in the diP Hb, the protocol for hexaPEGylated Hb will yield tetraPEGylated and the protocol for octaPEGylayed Hb will yield the hexaPEGylated Hbs.

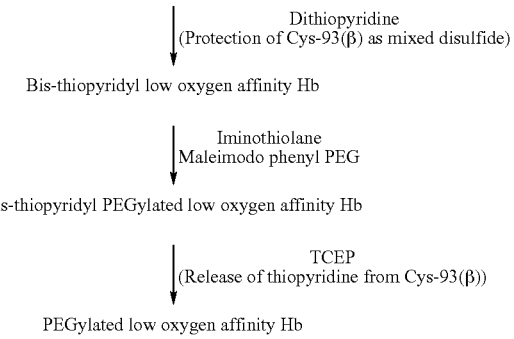

Example 4

Additional Designs for Generating Low $O_2$ Affinity PEGylated Hbs

One of the primary emphasis of the design of second generation PEGylated Hb is to have products with lower oxygen affinity compared to the hexaPEGylated Hb[SP-(PEG5K)$_6$ Hb] generated by Extension Arm Facilitated (EAF) PEGylation. In addition to the approach explained above as to how to use a combination of PEGylation platforms with αα-crosslinked Hb to generate molecular species with $O_2$ affinities in the range of 10 to 30 mm Hg, the following approaches can be used.

(A) Reaction of crosslinked Hbs with isothiocyanato phenyl PEG-5000: Studies of the PEGylation of αα-fumaryl Hb using isothiocyanato phenyl PEG 5000 PEG have exposed some unique aspects of such PEGylated Hb. A preparation of tetraPEGylated αα-fumaryl Hb (reaction carried out at room temperature using a ten fold molar excess of the reagent for six hours) generates a product, the four PEG-chains are on the four α-amino groups of the protein, and this PEGylated Hb exhibits an oxygen affinity in the region of 30 mm Hg.

The tetraPEGylated αα-fumaryl Hb generated by reductive alkylation chemistry exhibits an oxygen affinity around 16 mm of Hg, even though the pattern of PEGylation in the tetraPEGylated products generated using the two PEG-reagents is identical (site specifically modified at the four α-amino groups of the protein). Molecular modeling studies have suggested that the orientation of the PEG-chains from the site of PEGylation is very distinct between the two products, apparently a reflection of the high rigidity of the phenyl linker present in the isothiocyanato phenyl PEG-5000.

The reaction of isothiocyanato phenyl PEG-5000 with αα-fumaryl Hb can be used to control the oxygen affinity of the product by controlling the level of PEGylation. A preparation of diPEGylated Hb with PEGylation predominantly on the Val-1(β), the most reactive site for the PEGylation by this PEG reagent, exhibits a P50 in the region of 55 mm Hg. Thus, it is clear that one can modulate $O_2$ affinity of Hb over a wide range by carefully selecting the PEGylation strategy, extent of PEGylation, and the crosslinked Hb to customize the product with desired oxygen affinity for application as oxygen carrying plasma volume expander in very specific situation.

The fact that PEGylation of Cys-93(β) weakens the interdimeric interactions and increases the $O_2$ affinity, but at the same time this diPEGylated Hb, (SP-PEG5K)$_2$ Hb achieves a better tissue oxygenation than hexaPEGylated Hb generated by EAF-PEGylation, prompted the design of (SP-PEG-5K)2 Hb by EAF PEGylation wherein the two PEG chains are on the extension arms placed on the ε-amino groups of Lys resides and thiol group of Cys-93(β) remains unPEGylated. PDS Hb, wherein the thiol of Cys-93(β) is protected as a mixed disulfide with thiopyridine, is PEGylated at a protein concentration of 0.125 mM in the presence of 1.25 mm iminothiolane, and 6 mM maleimide PEG in PBS buffer at 40 C. Under these experimental conditions more than 50% of the PDS Hb is converted into diPEGylated PDS-Hb, wherein the PEGylation is only on ε-amino groups. This diPEGylated Hb after releasing the PDS using TCEP [with thiols of Cys-93(β) free] is a better product than the diPEGylated Hb with PEGylation on Cys-93(β) both in terms of its $O_2$ affinity (P50 around 12) and lower rate of autoxidation. DiPEGylated Hb with the PEGylation only on Cys-93(β) is a better material in terms of tissue oxygenation as compared to the hexaPEGylated Hb, the material that is currently in phase 3 clinical trial as a blood substitute. The new diPEGylated Hb with the ε-amino groups, is more resistant to autoxidation as Cys-93 (β) is free in this sample.

The reaction was also investigated of isothiocayanto phenyl PEG-5000 with ββ-sebacyl Hb, an intramolecularly crossbridged Hb with a sebacyl linkage between the ε-amino groups of Lys-82(β) that has a P50 around 28 mm Hg. TetraPEGylation lowers the P50 to 23 mm Hg, illustrating that PEGylation by isothiocynato phenyl PEG reagents minimally increases the $O_2$ affinity of intramolecularly crosslinked Hbs by the least amount as compared to the relatively larger increases caused by most other PEG regents.

(B) Design low and lower oxygen affinity PEGylated fibs without the use of intramolecular crosslinking: Modulation of PEGylation-induced weakening of interdimeric interactions: The choice of different forms of low O2 affinity intramolecularly crosslinked Hb is based on the general hypothesis that PEGylation induces either a global or a local structural/conformational modulation of Hb that destabilizes T quaternary state conformations and stabilizes the R quaternary state conformations of Hb through mechanisms that include the PEGylation-induced weakening of the interdimeric interactions of Hb. Recent results suggests that significant part of the structural and functional consequences of individual PEGylation protocols could be mapped to site specific modification/PEGylation. These findings raise the possibility that avoiding these specific modification sites, the conformational and functional consequences of PEGylation will be minimized thus leading to better products in terms of functionality, stability and autoxidation.

(1) EAF-PEGylation of Hb targeted only to the ε-amino groups of Hb: The dimer-tetramer dissociation constant for Hb is ~2 µM, and that of (SP-PEG5K)-2-Hb [Cys-93(β)PEGylated)] is 36 µM. On the other hand, hexaPEGylated Hb (SP-PEG5K)6-Hb, product generated by EAF-PEGylation has a dissociation constant of ~18 µM. Thus it is clear that PEGylation by itself does not induce weakening of the interdimeric interactions. The modification of Cys-93(β) appears to weaken the interdimeric interaction. Seemingly, EAF PEGylation at the ε-amino groups appears to provide sufficient stabilization to compensate for the weakening of the inter dimeric interactions induced by the PEGylation of Cys-93(β). HexaPEGylated Hb was generated by EAF PEGylation using PDS-Hb (Hb with the thiol Cys-93(β) reversibly protected during EAF-PEGylation as mixed disulfide with thiopyridine). This product exhibits a dissociation constant of 4.7 µM.

(2) Identification of the site of PEGylation that dictates the weakening of interdimeric interactions in the hexaPEGylated Hb generated by reductive alkylation chemistry based PEGylation: In the case of reductive alkylation mediated PEGylation of Hb generates molecules that are essentially dimeric even at a concentration of 0.5 mM, studies have now established that the weakening of the interdimeric interaction is essentially a site specific event of a PEGylation of Val-1(a). Interestingly, if uncrosslinked Hb is reductively alkylated with propionaldehyde site selectively at Val-1(a), the interdimeric interactions is increased (reduced dissociation). Propyl chain is the linker between the amino groups of Hb and PEG chains in the PEGylated Hb generated by reductive alkylation chemistry mediated PEGylation. Apparently, the PEG chain at the distal end of the propyl chain on Val-1(α) induces the dissociation effect to the PEGylated protein.

HexaPEGylated Hb propylated Val-1(α) was prepared by reductive alkylation chemistry based PEGylation. The resultant molecule is very stable and its dissociation constant is around 20 µM, close to that of a molecule where two copies of PEG chains are conjugated site specifically at Val-1(β) by reductive alkylation. Thus, one can effectively negate the weakening of the interdimeric interactions by avoiding PEGylation at Val-1(α) and Val-1(β), the critical sites in the molecule wherein the PEGylation influences the inter dimeric stability of the molecule. Thus crosslinks may not be needed to generate the low $O_2$ affinity Hbs.

(C) Design of improved versions of Extension Arm Facilitated PEGylation platforms: The observation that acylation chemistry based PEGylation of aa-fumaryl Hb generates a hexaPEGylated Hb that is more viscogenic than the materials generated by other PEGylation platforms prompted the development of nonconservative EAF PEGylation protocols, and this aspect has also been extended to manipulate the length of the extension arm, to increase the accessibility of the larger PEG reagents to the amino groups which are not readily accessible to direct PEGylation in spite of their chemical reactivity towards small molecular weight reagents.

A modified version of the nonconservative extension arm facilitated PEGylation has been now developed. This approach introduces maleimide at the distal end of the extension arm and the extension arms are linked to the e-amino group by isopetide linkage. To start with the caproic acid side chain was used, but the length of the extension arm could be manipulated as and when desired. The protein that carries multiple copies of maleimide at the distal end of the extension arms is reacted with thioPEG to get the desired PEGylated protein. In the case of Hb, PDS-Hb [dithiopyridyl Hb)] was used to reversibly protect the thiol of Cys-93($\beta$) during PEGylation. This approach is also cost effective as the original EAF-thiol maleimide chemistry based PEGylation, and the new approach, which is referred to as EAF-maleimide-thiol chemistry based PEGylation, to distinguish it from the earlier approach. The approach is presented below in a schematic fashion.

Adult human hemoglobin initially purified by DE52 ion exchange was treated with 4-PDS to block $\beta$93 cysteine. Hemoglobin (0.5 mM) was reacted with 20 fold molar excess of 4-PDS for overnight in cold, and excessive 4-PDS is removed by dialysis. This mixed disulfide of Hb (or of crosslinked Hb) is further concentrated and reacted (1 mM) with 10 fold molar excess of bifunctional linker sulfo-EMCS for 2 hours in cold. Reaction mixture is dialyzed extensively for the removal of excessive and leaving group of bifunctional reagent. Now $\epsilon$-amino groups of hemoglobin are modified by the sulfosuccinimidyl ester and an extension arm with a free maleimide group is bound to the protein. The dialyzed sample (modified Hb) is concentrated to 1 mM and reacted with equal amount of 10 mM thiol PEG5000 for overnight in cold to generate a PEGylated HbA. Unbound PEG5K is removed by dialysis. Under these reaction conditions a HexaPEGylation of the protein is achieved and this is confirmed by HPLC, FPLC and SDS-PAGE analysis.

The molecular and functional properties of the new hexaPEGylated product are shown in Table 14. The colloidal osmotic pressure (COP) was measured for 4% solution at room temperature and the viscosity of the solution was measured at 4% at 37° C. Hydrodynamic radius is measured at 25° C. using a 1 mg/ml solution. Oxygen equilibrium curve have been obtained using Hemox analyzer at 37° C. in PBS 7.4.

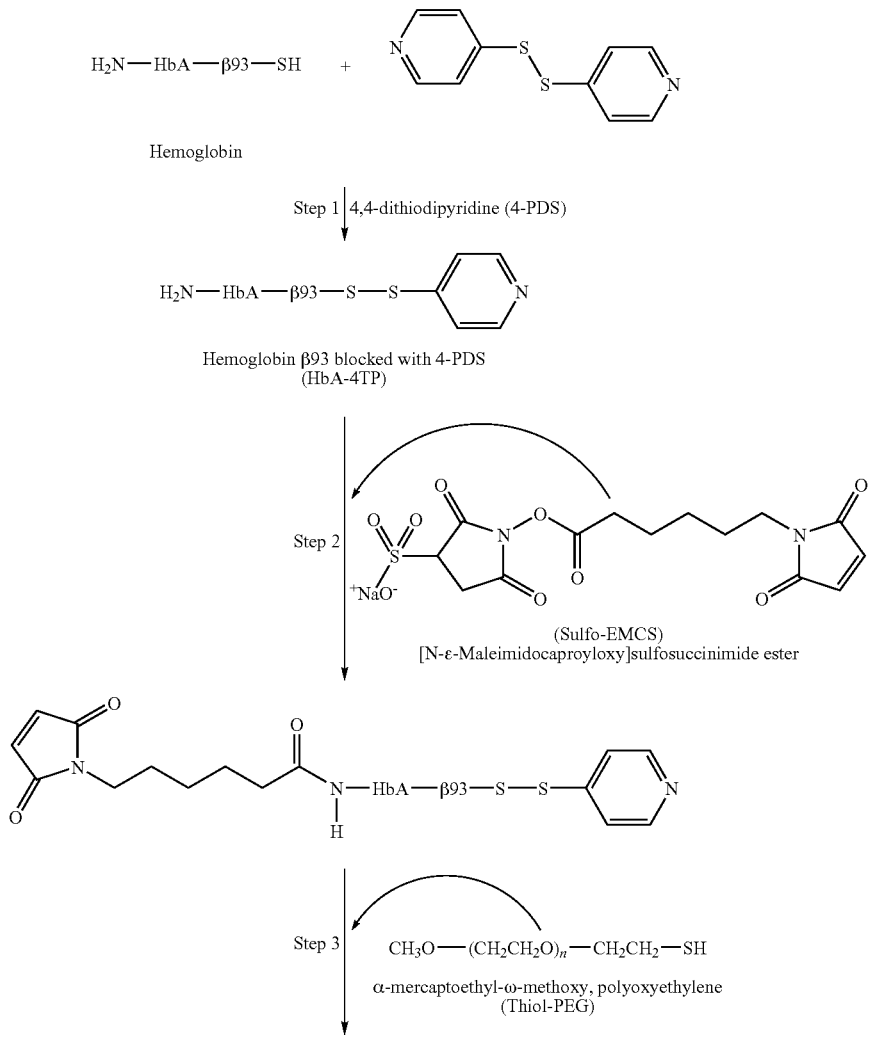

Schematic Representation of the Extension Arm Facilitated Maleimide Thiol Chemistry Based PEGylation

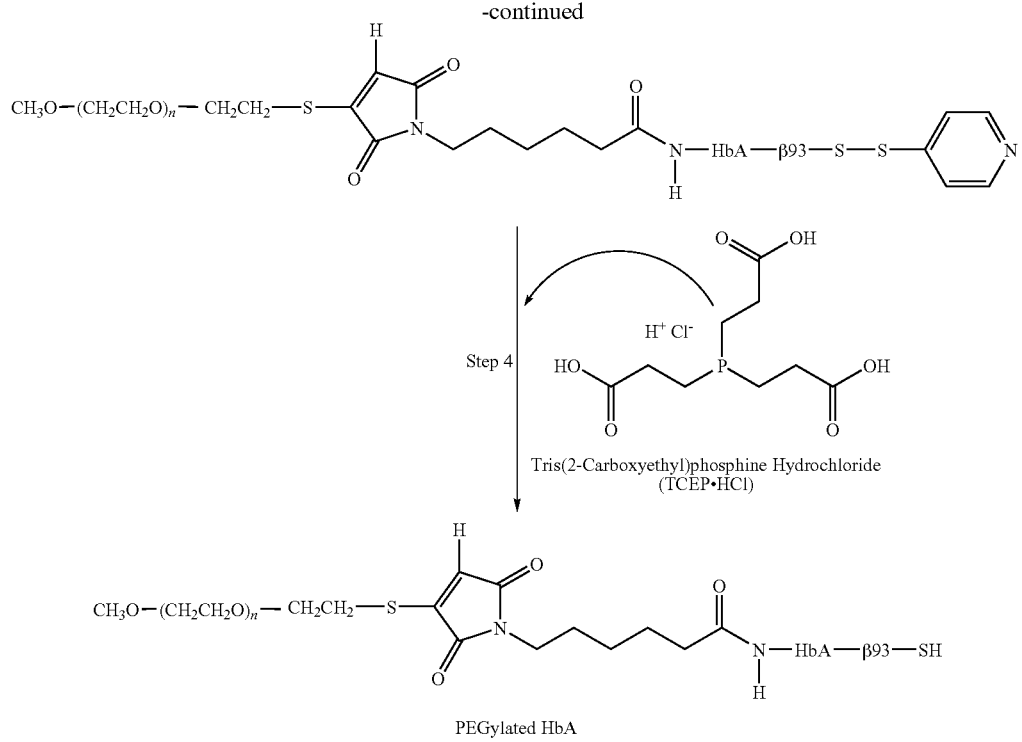

Step 4

Tris(2-Carboxyethyl)phosphine Hydrochloride (TCEP·HCl)

PEGylated HbA

TABLE 14

Comparative properties of different hexaPEGylated Hb.

| Sample | COP (mmHg) | Viscosity (cP) | Radius (nm) | DSC Tm °C. | $P_{50}$ (mmHg) | | Hill Coefficient (h) | |
|---|---|---|---|---|---|---|---|---|
| HbA | 14.3 | 1.01 | 2.98 | 70.0 | 15.26 | Cys-93 (free) | 3.09 | Cys-93 (free) |
| HbA-4PDS | 13.7 | 1.07 | — | — | 10.47 | 13.82 | 2.5 | 2.5 |
| (SH-PEG5K)6-HbA | 58.0 | 1.98 | 5.35 | 70.0 | 8.9 | 9.48 | 1.63 | 1.58 |
| (SH-PEG5K)6-ααHbA | 76.4 | 2.27 | 5.67 | 70.5 | 11.46 | 11.45 | 1.39 | 1.37 |

What is interesting in this case is that though the extension arm is linked to the protein by acylation chemistry, the material does not dissociate into PEGylated dimers as the with hexa propionyl PEG-5K Hb, and the material is not much more viscogenic than the hexaPEGylated Hb generated by EAF-PEGylation using iminothiolane. Apparently, the presence of extension arm between the PEG chains and the protein (that facilitates the spacing of the PEG chain away from the protein hydration layer), minimizes the impact of the PEG-shell on the structure of the protein.

REFERENCES

Acharya, A. S., Bobelis, D. J., and White, S. P. (1994) Electrostatic modification at the amino termini of hemoglobin A, J. Biol. Chem. 269, 2796-2804.

Acharya, A. S., Intaglietta, M., Tsai, A. G., Malavalli, A., Vandegriff, K., Winslow, R. M., Smith, P. K., Friedman, J. M. and Manjula, B. N. (2005) Enhanced molecular volume of conservatively pegylated Hb: (SP-PEG5K)$_6$-HbA is non-hypertensive. Artificial Cells, Blood Subs. Biotechnol. 33, 239-255.

Ampulski, R. S., Ayers, V. E., and Morell, S. A. (1969) Determination of the reactive sulfhydryl groups in heme proteins with 4,4'-dipyridinedisulfide, Anal. Biochem. 32, 163-169.

Arnone, A., Benesch, R. E., and Benesch, R. (1977) Structure of human deoxyhemoglobin specifically modified with pyridoxal compounds, J. Mol. Biol. 115, 627-642.

Baldwin, J. and Chothia, C. (1979) Haemoglobin: the structural changes related to ligand binding and its allosteric mechanism. J. Mol. Biol. 129, 175-220.

Benesch, R. and Benesch, R. E. (1981) Preparation and properties of hemoglobin modified with derivatives of pyridoxal, Methods Enzymol. 76, 147-159.

Benesch, R. E, Yung, S., Suzuki, T., Bauer, C., and Benesch, R. (1973) Pyridoxal compounds as specific reagents for the alpha and beta N-termini of hemoglobin, Proc Natl Acad Sci USA. 70, 2595-2599.

Bonaventura, C., Tesh, S., Faulkner, K. M., Kraiter, D., and Crumbliss, A. L. (1998) Conformational fluctuations in deoxy hemoglobin revealed as a major contributor to anionic modulation of function through studies of the oxygenation and oxidation of hemoglobins A0 and Deer Lodge beta2(NA2)His→Arg, Biochemistry 37, 496-506.

Chang, T. M. S. (1999) Future prospects for artificial blood. Trends Biotechnol. 17, 61-67.

Chatterjee, R., Walder, R. Y., Arnone, A. and Walder, J. A. (1982) Mechanism for the increase in solubility of deoxyhemoglobin S due to cross-linking the beta chains between lysine-82 beta 1 and lysine-82 beta 2, Biochemistry 21, 5901-5909.

Chatterjee, R., Welty, E. V., Walder, R. Y., Pruitt, S. L., Rogers, P. L., Arnone, A. and Walder, J. A. (1986) Isolation and characterization of a new hemoglobin derivative cross-linked between the alpha chains (lysine 99 alpha 1-lysine 99 alpha 2). J. Biol. Chem. 261, 9929-9937.

Conover, C. D., Linberg, R., Shum, K. L. and Shorr, R. G. (1999) The ability of polyethylene glycol conjugated bovine hemoglobin (PEG-Hb) to adequately deliver oxygen in both exchange transfusion and top-loaded rat models. Artif. Cells Blood Substit. Immobil. Biotechnol. 27, 93-107.

Dhalluin, C., Ross, A., Leuthold, L. A., Foser, S., Gsell, B., Muller, F. and Senn, H. (2005) Structural and biophysical characterization of the 40 kDa PEG-interferon-alpha2a and its individual positional isomers. Bioconjugate Chem. 16, 504-517.

DiDonato, A., Fantl, W. J., Acharya, A. S., and Manning, J. M. (1983) Selective carboxymethylation of the alpha-amino groups of hemoglobin. Effect on functional properties, J. Biol. Chem. 258, 11890-11895.

Doyle, M. P., Apostol, I. and Kerwin B. A. (1999) Glutaraldehyde modification of recombinant human hemoglobin alters its hemodynamic propertie. J. Biol. Chem. 274, 2583-2591.

Fantl, W. J., Manning, L. R., Ueno, H., Di Donato, A., and Manning, J. M. (1987) Properties of carboxymethylated cross-linked hemoglobin A, Biochemistry 26, 5755-5761.

Fronticelli C, Bucci E, Razynska A, Sznajder J, Urbaitis B, Gryczynski Z. (1990) Bovine hemoglobin pseudo-crosslinked with mono(3,5-dibromosalicyl)-fumarate, Eur. J. Biochem. 193, 331-336.

Gulati, A., Barve, A. and Sen, A. P. (1999) Pharmacology of hemoglobin therapeutics. J. Lab. Clin. Med. 133, 112-119.

Haney, D. N., and Bunn, H. F. (1976) Glycosylation of hemoglobin in vitro: affinity labeling of hemoglobin by glucose-6-phosphate. Proc Natl Acad Sci USA. 73, 3534-3538.

Hess, J. R., Macdonald, V. W., and Brinkley, W. W. (1993) Systemic and pulmonary hypertension after resuscitation with cell-free hemoglobin, J. Appl. Physiol. 74, 1769-1778.

Hirsch, R. E. (2003) Hemoglobin fluorescence. Methods Mol. Med. 82, 133-154

Hsu, M. C. and Woody, R. W. (1971) The origin of the heme Cotton effects in myoglobin and hemoglobin. J. Am. Chem. Soc. 93, 3515-3525.

Cabrales, P., Nacharaju, P., Manjula, B. N., Tsai, A. G., Acharya, S. A. and Intaglietta, M. (2005) Early difference in tissue pH and microvascular hemodynamics in hemorrhagic shock resuscitation using polyethylene glycol-albumin- and hydroxyethyl starch-based plasma expanders. Shock 24, 66-73.

Conover, C. D., Malatesta, P., Lejeune, L., Chang, C. L., and Shorr, R. G. (1996) The effects of hemodilution with polyethylene glycol bovine hemoglobin (PEG-Hb) in a conscious porcine model, J. Investig. Med. 44, 238-246.

Conover, C. D., Lejeune, L., Shum, K., Gilbert, C., and Shorr, R. G. (1997) Physiological effect of polyethylene glycol conjugation on stroma-free bovine hemoglobin in the conscious dog after partial exchange transfusion, Artif. Organs. 21, 369-378.

Doherty, D. H., Doyle, M. P., Curry, S. R., Vali, R. J., Fattor, T. J., Olson, J. S., and Lemon, D. D. (1998) Rate of reaction with nitric oxide determines the hypertensive effect of cell-free hemoglobin, Nat Biotechnol. 16, 672-676.

Dou, Y., Maillett, D. H., Eich, R. F., and Olson, J. S. (2002) Myoglobin as a model system for designing heme protein based blood substitutes, Biophys. Chem. 98, 127-148.

Eich, R. F., Li, T., Lemon, D. D., Doherty, D. H., Curry, S. R., Aitken, J. F., Mathews, A. J., Johnson, K. A., Smith, R. D., Phillips, G. N. Jr., Olson, J. S., and Lemon, D. D. (1996) Mechanism of NO-induced oxidation of myoglobin and hemoglobin, Biochemistry 35, 6976-6983.

Fermi, G., Perutz, M. F., Shaanan, B., and Fourme, R. (1984) The crystal structure of human deoxyhaemoglobin at 1.74 Å resolution J. Mol. Biol. 175, 159-174.

Friedman, J. M. (1985) Structure, dynamics, and reactivity in hemoglobin, Science 228, 1273-1280.

Friedman, J. M. (1994) Time-resolved resonance Raman spectroscopy as probe of structure, dynamics, and reactivity in hemoglobin, Methods Enzymol. 232, 205-231.

Friedman, J. M., Scott, T. W., Stepnoski, R. A., Ikeda-Saito, M., and Yonetani, T. (1983) The iron-proximal histidine linkage and protein control of oxygen binding in hemoglobin. A transient Raman study, J. Biol. Chem. 258, 10564-10572.

Friedman, J. M., Scott, T. W., Fisanick, G. J., Simon, S. R., Findsen, E. W., Ondrias, M. R., and MacDonald, V. W. (1985) Localized control of ligand binding in hemoglobin: effect of tertiary structure on picosecond geminate recombination, Science 229, 187-190.

Fernandez, E. J., Abad-Zapatero, C., and Olsen, K. W. (2000) Crystal structure of Lysbeta(1)82-Lysbeta(2)82 crosslinked hemoglobin: a possible allosteric intermediate, J. Mol. Biol. 296, 1245-1256.

Hu, T., Prabhakaran, M., Acharya, S. A. and Manjula, B. N. (2005) Influence of the chemistry of conjugation of poly (ethylene glycol) to Hb on the oxygen-binding and solution properties of the PEG-Hb conjugate. Biochem. J. 392, 555-564.

Hu, T., Manjula, B. N., Li, D., Brenowitz, M., and Acharya, S. A. (2007) Influence of intramolecular cross-links on the molecular, structural and functional properties of PEGylated hemoglobin, Biochem. J. 402, 143-151.

Huang, J., Juszczak, L. J., Peterson, E. S., Shannon, C., Yang, M., Huang, S., Vidugiris G. V., and Friedman J. M. (1999) The conformational and dynamic basis for ligand binding reactivity in hemoglobin Ypsilanti (beta 99 asp→Tyr): origin of the quaternary enhancement effect, Biochemistry 38, 4514-4525.

Imai, K., Hamilton, H. B., Miyaji, T., and Shibata, S. (1972) Physicochemical studies of the relation between structure and function in hemoglobin Hiroshima (HC3, histidine leads to aspartate), Biochemistry 11, 114-121.

Imai, K., Tsuneshige, A., Harano, T., and Harano, K. (1989) Structure-function relationships in hemoglobin Kariya, Lys-40(C5) alpha-Glu, with high oxygen affinity. Functional role of the salt bridge between Lys-40 alpha and the beta chain COOH terminus, J. Biol. Chem. 264, 11174-11180.

Intaglietta, M. (1997) Whitaker Lecture 1996: microcirculation, biomedical engineering, and artificial blood. Ann. Biomed. Eng. 25, 593-603.

Khan, I., Dantsker, D., Samuni, U., Friedman, A. J., Bonaventura, C., Manjula, B., Acharya, S. A., and Friedman, J. M. (2001) Beta 93 modified hemoglobin: kinetic and conformational consequences, Biochemistry 40, 7581-7592.

Kellett, G. L. (1971) Dissociation of hemoglobin into subunits. Ligand-linked dissociation at neutral pH. J. Mol. Biol. 59, 401-424.

Kilmartin, J. V., Hewitt, J. A., and Wootton, J. F. (1975) Alteration of functional properties associated with the change in quaternary structure in unliganded haemoglobin, J. Mol. Biol. 93, 203-218.

Kim, H. W., and Greenburg, A. G., (1997) Ferrous hemoglobin scavenging of endothelium derived nitric oxide is a principal mechanism for hemoglobin mediated vasoactivities in isolated rat thoracic aorta, Artif. Cells Blood Substit. Immobil. Biotechnol. 25, 121-133.

Kim, H. W., and Greenburg, A. G. (2005) Mechanisms for vasoconstriction and decreased blood flow following intravenous administration of cell-free native hemoglobin solutions, Adv. Exp. Med. Biol. 566, 397-401.

Klein, H. G. (2000) The prospects for red-cell substitutes. New Engl. J. Med. 342, 1666-1668.

Kramer, G. C. (2003) Counterintuitive red blood cell substitute—polyethylene glycol-modified human hemoglobin. Crit. Care. Med. 31, 1882-1883.

Kwiatkowski, L. D., Hui, H. L, Wierzba, A., Noble, R. W., Walder, R. Y., Peterson, E. S., Sligar, S. G., and Sanders, K. E. (1998) Preparation and kinetic characterization of a series of betaW37 variants of human hemoglobin A: evidence for high-affinity T quaternary structures, Biochemistry 37, 4325-4335.

Lalezari, I., Lalezari, P., Poyart, C. Marden, M., Kister, J., Bohn, B., Fermi, G., and Perutz, M. F. (1990) New effectors of human hemoglobin: structure and function, Biochemistry 29, 1515-1523.

Li, D., Manjula, B. N. and Acharya A. S. (2006) Extension Arm Facilitated PEGylation of Hemoglobin: Correlation of the Properties with the Extent of PEGylation. Protein J. In press.

Li, D., Ho, N. T., Simplaceanu, V., Ho, C., Acharya, A. S, and Manjula, B. N. (2007) Molecular aspects of the high oxygen affinity of nonhypertensive PEGylated hemoglobin, [(SP-PEG5K)6-Hb]. Artif. Cells Blood Substit. Biotechnol. In press.

Lieberthal, W., Fuhro, R., Alam, H., Rhee, P., Szebeni, J., Hechtman, H. B., Favuzza, J., Veech, R. L., and Valeri, C. R. (2002) Comparison of the effects of a 50% exchange-transfusion with albumin, hetastarch, and modified hemoglobin solutions, Shock 17, 61-69.

Lippincott, J., Hess, E. and Apostol, I. (1997) Mapping of recombinant hemoglobin using immobilized trypsin cartridges. Anal. Biochem. 252, 314-325.

Manjula, B. N. and Acharya, A. S. (2003) Purification and molecular analysis of hemoglobin by high-performance liquid chromatography. Methods Mol Med. 82, 31-47.

Manjula, B. N., Malavalli, A., Smith, P. K., Chan, N. L., Arnone, A., Friedman, J. M. and Acharya, A. S. (2000) Cys-93-betabeta-succinimidophenyl polyethylene glycol 2000 hemoglobin A. Intramolecular cross-bridging of hemoglobin outside the central cavity. J. Biol. Chem. 275, 5527-5534.

Manjula, B. N., Malavalli, A., Prabhakaran, M., Friedman, J. M., and Acharya, A. S. (2001) Activation of the low oxygen affinity-inducing potential of the Asn108(beta)→Lys mutation of Hb-Presbyterian on intramolecular alpha alpha-fumaryl cross-bridging, Protein Eng. 14, 359-366.

Manjula, B. N., Tsai, A., Upadhya, R., Perumalsamy, K., Smith, P. K., Malavalli, A., Vandegriff, K. D., Winslow, R. M., Intaglietta, M., Prabhakaran, M., Friedman, J. M. and Acharya, A. S. (2003) Site-specific PEGylation of hemoglobin at Cys-93(beta): correlation between the colligative properties of the PEGylated protein and the length of the conjugated PEG chain. Bioconjugate Chem. 14, 464-472.

Manjula, B. N., Tsai, A. G., Intaglietta, M., Tsai, C-H., Ho, C., Smith, P. K., Perumalsamy, K., Kanika, N. D., Friedman, J. M. and Acharya, A. S. (2005) Conjugation of multiple copies of polyethylene glycol to hemoglobin facilitated through thiolation: influence on hemoglobin structure and function. Protein J. 42, 133-146.

Marden, M. C., Hazard, E. S., Kimble, C., and Gibson, Q. H. (1987) Geminate ligand recombination as a probe of the R, T equilibrium in hemoglobin, Eur. J. Biochem. 169, 611-615.

Mathews, A. J., Rohlfs, R. J., Olson, J. S., Tame, J., Renaud, J. P., and Nagai, K. (1989) The effects of E7 and E11 mutations on the kinetics of ligand binding to R state human hemoglobin, J. Biol. Chem. 264, 16573-16583.

Mawjood, A. H., Miyazaki, G., Kaneko, R., Wada, Y., and Imai K. (2000) Site-directed mutagenesis in hemoglobin: test of functional homology of the F9 amino acid residues of hemoglobin alpha and beta chains, Protein Eng. 13, 113-120.

Moh, P. P., Fiamingo, F. G., and Alben, J. O., (1987) Conformational sensitivity of beta-93 cysteine SH to ligation of hemoglobin observed by FT-IR spectroscopy, Biochemistry 26, 6243-6249.

Moo-Penn et al. (1981), Am. J. Hematol. 11, 137-145.

Murray, L. P., Hofrichter, J., Henry, E. R., Ikeda-Saito, M., Kitagishi, K., Yonetani, T., and Eaton, W. A. (1988) The effect of quaternary structure on the kinetics of conformational changes and nanosecond geminate rebinding of carbon monoxide to hemoglobin, Proc. Natl. Acad. Sci. U.S.A. 85, 2151-2155.

Olson, J. S., Eich, R. F., Smith, L. P., Warren, J. J., and Knowles, B. C. (1997) Protein engineering strategies for designing more stable hemoglobin-based blood substitutes, Artif Cells Blood Substit. Immobil. Biotechnol. 25, 227-241.

Perutz, M. F. (1970) Stereochemistry of cooperative effects in haemoglobin. Nature 228, 726-738.

Perutz, M. F. (1989) Mechanisms regulating the reactions of human hemoglobin with oxygen and carbon monoxide. Q. Rev. Biophys. 22, 139-237.

Perutz, M. F., Ladner, J. E., Simon, S. R. and Ho, C. (1974) Influence of globin structure on the state of the heme. I. Human deoxyhemoglobin. Biochemistry 13, 2163-2173.

Perutz, M. F., Shih, D. T-b., and Williamson, D. (1994) The chloride effect in human haemoglobin. A new kind of allosteric mechanism, J. Mol. Biol. 239, 555-560.

Peterson, E. S., and Friedman, J. M. (1998) A possible allosteric communication pathway identified through a resonance Raman study of four beta37 mutants of human hemoglobin A, Biochemistry 37, 4346-4357.

Rao, M. J., Schneider, K., Chait, B. C., Chao, T. L., Keller, H. L., Anderson, S. M., Manjula, B. N., Kumar, R. A. and Acharya, A. S. (1994) Recombinant hemoglobin A produced in transgenic swine: structural equivalence with human hemoglobin A. Artif. Cells Blood Substit. Immobil. Biotechnol. 22, 695-700.

Rao et al. (2000) J. Mol. Biol. 300, 1389-1406.

Razynska, A., Matheson-Urbaitis, B., Fronticelli, C., Collins, J. H., and Bucci, E. (1996) Stabilization of the tetrameric structure of human and bovine hemoglobins by pseudocrosslinking with muconic acid, Arch. Biochem. Biophys. 326, 119-125.

Richard, V., Dodson, G. G., and Mauguen, Y. (1993) Human deoxyhaemoglobin-2,3-diphosphoglycerate complex low-salt structure at 2.5 Å resolution. J. Mol. Biol. 233, 270-274.

Rohlfs, R. J., Bruner, E., Chiu, A., Gonzales, A., Gonzales, M. L., Magde, M. D., Vandegriff, K. D. and Winslow, R. M. (1998) Arterial blood pressure responses to cell-free hemoglobin solutions and the reaction with nitric oxide. J. Biol. Chem. 273, 12128-12134.

Roy, R. P., and Acharya, A. S. (1994) Semisynthesis of hemoglobin, Methods Enzymol., 231, 194-215.

Saxena, R., Wijnhoud, A. D., and Carton, H. (1999) Controlled safety study of a hemoglobin-based oxygen carrier, DCLHb, in acute ischemic stroke, Stroke 30, 993-996.

Schneider et al. (1975) Biochim. Biophys. Acta 400, 365-373.

Taketa, F., Antholine, W. E., Mauk, A. G., and Libnoch, J. A. (1975) Nitrosylhemoglobin Wood: effects of inositol hexaphosphate on thiol reactivity and electron paramagnetic resonance spectrum, Biochemistry 14, 3229-3233.

Tsai, A. G., Vandegriff, K. D., Intaglietta, M., and Winslow, R. M. (2003) Targeted O2 delivery by low-P50 hemoglobin: a new basis for O2 therapeutics, Am. J. Physiol. Heart Circ. Physiol. 285, 1411-1419.

Tsai, A. G., Cabrales, P., and Intaglietta, M. (2004a) Increased tissue $PO_2$ and decreased $O_2$ delivery and consumption after 80% exchange transfusion with polymerized hemoglobin. Am. J. Physiol. Heart Circ. Physiol. 287, H320-H330.

Tsai, A. G., Cabrales, P., and Intaglietta, M. (2004b) Oxygen-carrying blood substitutes: a microvascular perspective, Expert Opin. Biol. Ther. 4, 1147-1157.

Yu, Z., Friso, G., Miranda, J. J., Patel, M. J., Lo-Tseng, T., Moore, E. G., and Burlingame, A. L. (1997) Structural characterization of human hemoglobin crosslinked by bis (3,5-dibromosalicyl) fumarate using mass spectrometric techniques, Protein Sci. 6, 2568-2577.

Vandegriff, K. D., Medina, F., Marini, M. A., and Winslow, R. M. (1989) Equilibrium oxygen binding to human hemoglobin cross-linked between the alpha chains by bis(3,5-dibromosalicyl) fumarate, J. Biol. Chem. 264, 17824-17833.

Vandegriff, K. D., Malavalli, A., Wooldridge, J., Lohman, J. and Winslow, R. M. (2003) MP4, a new nonvasoactive PEG-Hb conjugate. Transfusion 43, 509-516.

Walder, J. A., Walder, R. Y., and Arnone, A. (1980) Development of antisickling compounds that chemically modify hemoglobin S specifically within the 2,3-diphosphoglycerate binding site, J. Mol. Biol. 141, 195-216.

Winslow, R. M. (2000a) Blood substitutes. Adv. Drug Del. Rev. 40, 131-142.

Winslow, R. M. (2000b) αα-crosslinked hemoglobin: was failure predicted by preclinical testing? Vox. Sang. 79, 1-20.

Winslow, R. M. (2003) Current status of blood substitute research: towards a new paradigm. J. Intern. Med. 253, 508-517.

Winslow, R. M., Gonzales, A., Gonzales, M. L., Magde, M., McCarthy, M., Rohlfs, R. J. and Vandegriff, K. D. (1998) Vascular resistance and the efficacy of red cell substitutes in a rat hemorrhage model. J. Appl. Physiol. 85, 993-1003.

Zentz, C., Pin, S, and Alpert, B. (1994) Stationary and time-resolved circular dichroism of hemoglobins. Methods Enzymol. 232, 247-266.

U.S. Pat. No. 5,585,484.
U.S. Pat. No. 5,843,888.
U.S. Pat. No. 6,486,123.
U.S. Pat. No. 7,144,989 B2.

In view of the above, it will be seen that the several advantages of the invention are achieved and other advantages attained.

As various changes could be made in the above methods and compositions without departing from the scope of the invention, it is intended that all matter contained in the above description and shown in the accompanying drawings shall be interpreted as illustrative and not in a limiting sense.

All references cited in this specification are hereby incorporated by reference. The discussion of the references herein is intended merely to summarize the assertions made by the authors and no admission is made that any reference constitutes prior art. Applicants reserve the right to challenge the accuracy and pertinence of the cited references.

What is claimed is:

1. A method of modifying a hemoglobin, the method comprising introducing at least two chemical modifications to the hemoglobin, wherein each chemical modification by itself results in a hemoglobin with lower oxygen affinity than the same hemoglobin that is unmodified, wherein one of the chemical modifications comprises PEGylating the hemoglobin, wherein the hemoglobin comprises at least one thiol at a Cys-92(β) or a Cys-93(β), wherein the Cys-92(β) or the Cys-93(β) is protected before PEGylation, then deprotected after PEGylation, and wherein the Cys-92(β) or the Cys-93(β) is protected with dithiopyridine and deprotected with Tris(2-carboxyethyl)phosphine (TCEP).

2. The method of claim 1, wherein one of the chemical modifications is an intramolecular crosslink.

3. The method of claim 2, wherein the intramolecular crosslink is an α-fumaryl crosslink at Lys-99(α).

4. The method of claim 1, wherein one of the chemical modifications is an affinity labeling of an effector binding domain.

5. The method of claim 1, wherein one of the chemical modifications is the introduction of a negative charge at the amino terminal of a β-chain.

6. The method of claim 5, wherein the introduction of a negative charge is by the addition of glyceraldehyde-3-phosphate in the presence of sodium cyanoborohydride.

7. The method of claim 5, wherein the introduction of a negative charge is by 2-hydroxy, 3-phospho propylation (HPPr).

8. The method of claim 1, wherein one chemical modification is by HPPr and another chemical modification is an αα-fumaryl crosslink at Lys-99(α).

9. The method of claim 8, wherein the αα-fumaryl crosslink is introduced into an HPPr-Hb.

10. A method of modifying a hemoglobin, the method comprising adding glyceraldehyde-3-phosphate to the hemoglobin in the presence of sodium cyanoborohydride, and PEGylating the hemoglobin, wherein the hemoglobin comprises at least one thiol at a Cys-92(β) or a Cys-93(β), wherein the Cys-92(β) or the Cys-93(β) is protected before PEGylation, then deprotected after PEGylation, and wherein the Cys-92(β) or the Cys-93(β) is protected with dithiopyridine and deprotected with Tris(2-carboxyethyl)phosphine (TCEP).

11. A method of modifying a hemoglobin, the method comprising introducing at least two chemical modifications to the hemoglobin, wherein each chemical modification is independently an intramolecular crosslink, an affinity labeling of an effector binding domain, or an introduction of a negative charge at the amino terminal of a β-chain, and PEGylating the hemoglobin, wherein the hemoglobin comprises at least one thiol at a Cys-92(β) or a Cys-93(β), wherein the Cys-92(β) or the Cys-93(β) is protected before PEGylation, then deprotected after PEGylation, and wherein the Cys-92

(β) or the Cys-93(β) is protected with dithiopyridine and deprotected with Tris(2-carboxyethyl)phosphine (TCEP).

12. The method of claim 1, wherein the PEGylation is by reductive alkylation.

13. The method of claim 1, wherein the PEGylation is by extension arm facilitated maleimide chemistry.

14. The method of claim 12, wherein the hemoglobin is diPEGylated or tetraPEGylated or hexaPEGylated.

15. A method of making a hemoglobin, the method comprising tetraPEGylating the hemoglobin by extension arm facilitated maleimide chemistry or diPEGylating the hemoglobin by extension arm facilitated maleimide chemistry or hexaPEGylating the hemoglobin by extension arm facilitated maleimide chemistry, wherein the hemoglobin comprises at least one thiol at a Cys-92(β) or Cys-93(β), wherein the Cys-92(β) or the Cys-93(β) is protected before PEGylation, then deprotected after PEGylation, and wherein the Cys-92 (β) or the Cys-93(β) is protected with dithiopyridine and deprotected with Tris(2-carboxyethyl)phosphine (TCEP).

16. The method of claim 10, wherein the PEGylation is by extension arm facilitated maleimide chemistry.

17. The method of claim 11, wherein the PEGylation is by extension arm facilitated maleimide chemistry.

18. The method of claim 1, wherein the PEG is maleimido phenyl PEG.

19. The method of claim 1, wherein the PEG has a molecular weight of 5,000 daltons.

* * * * *